United States Patent
John et al.

(10) Patent No.: US 9,534,016 B2
(45) Date of Patent: Jan. 3, 2017

(54) NETRIN LOOP PEPTIDE MIMETICS AND USES THEREOF

(71) Applicant: Buck Institute for Research on Aging, Novato, CA (US)

(72) Inventors: Varghese John, San Francisco, CA (US); Clare Peters-Libeu, Sebastopol, CA (US); Dale E. Bredesen, Novato, CA (US)

(73) Assignee: BUCK INSTITUTE FOR RESEARCH ON AGING, Novato, CA (US)

( * ) Notice: Subject to any disclaimer, the term of this patent is extended or adjusted under 35 U.S.C. 154(b) by 0 days.

(21) Appl. No.: 14/360,859

(22) PCT Filed: Nov. 27, 2012

(86) PCT No.: PCT/US2012/066676
§ 371 (c)(1),
(2) Date: May 27, 2014

(87) PCT Pub. No.: WO2013/082045
PCT Pub. Date: Jun. 6, 2013

(65) Prior Publication Data
US 2015/0017148 A1  Jan. 15, 2015

Related U.S. Application Data

(60) Provisional application No. 61/563,914, filed on Nov. 28, 2011.

(51) Int. Cl.
| | |
|---|---|
| *C07K 7/06* | (2006.01) |
| *C07K 14/775* | (2006.01) |
| *A61K 38/08* | (2006.01) |
| *C07K 14/62* | (2006.01) |
| *A61K 38/30* | (2006.01) |
| *A61K 38/28* | (2006.01) |
| *A61K 38/17* | (2006.01) |
| *C07K 14/65* | (2006.01) |
| *A61K 47/48* | (2006.01) |
| *A61K 38/46* | (2006.01) |
| *A61K 38/04* | (2006.01) |
| *A61K 38/12* | (2006.01) |

(52) U.S. Cl.
CPC ............. *C07K 7/06* (2013.01); *A61K 38/04* (2013.01); *A61K 38/08* (2013.01); *A61K 38/12* (2013.01); *A61K 38/1716* (2013.01); *A61K 38/28* (2013.01); *A61K 38/30* (2013.01); *A61K 38/465* (2013.01); *A61K 47/48215* (2013.01); *C07K 14/62* (2013.01); *C07K 14/65* (2013.01); *C07K 14/775* (2013.01); *C07K 2319/01* (2013.01); *C12Y 301/01034* (2013.01)

(58) Field of Classification Search
None
See application file for complete search history.

(56) References Cited

U.S. PATENT DOCUMENTS

| | | | |
|---|---|---|---|
| 6,242,416 B1 * | 6/2001 | Gilchrest et al. | 514/8.4 |
| 2009/0181881 A1 * | 7/2009 | Mehlen et al. | 514/8 |
| 2010/0099609 A1 | 4/2010 | John et al. | |
| 2012/0178690 A1 | 7/2012 | Kennedy | |
| 2012/0190626 A1 | 7/2012 | Sugimura | |

FOREIGN PATENT DOCUMENTS

| | | |
|---|---|---|
| WO | WO 2006/087550 | 8/2006 |
| WO | WO 2013/082045 | 6/2013 |

OTHER PUBLICATIONS

Kaden et al., The Journal of Biological Chemistry (2008) 283, 7271-7279.*
PCT International Search Report and Written Opinion dated May 1, 2013 issued in PCT/US2012/066676 [WO 2013/082045].
PCT International Preliminary Report on Patentability and Written Opinion dated Jun. 12, 2014 issued in PCT/US2012/066676 [WO 2013/082045].
Lourenco et al. (May 2009) "Netrin-1 interacts with amyloid precursor protein and regulates amyloid-beta production" *Cell Death Differ* 16(5): 655-663.
Stanco et al. (May 5, 2009) "Netrin-1-alpha3beta1 integrin interactions regulate the migration of interneurons through the cortical marginal zone" *PNAS* 106(18): 7595-7600.

* cited by examiner

*Primary Examiner* — Karlheinz R Skowronek
*Assistant Examiner* — Catherine Mader
(74) *Attorney, Agent, or Firm* — Tom Hunter; Weaver Austin Villeneuve & Sampson LLP

(57) ABSTRACT

In certain embodiments compositions are provided that comprise a pentapeptide comprising the formula: $C^1$-$X^2$-$X^3$-$X^4$-$C^5$ where $C^1$ and $C^5$ are independently selected cysteines or cysteine analogues, or other amino acids with sidechains suitable for cyclization, where the cysteines or cysteine analogs are attached to each other by a linkage that does not comprise $X^2$, $X^3$, and $X^4$; where $X^2$, $X^3$, and $X^4$ are independently selected amino acids; and the peptide, when administered to a cell alters APP signaling and/or switches APP processing from aberrant to normal. The compositions mitigate amyloid plaque formation.

7 Claims, 6 Drawing Sheets

SEQUENCE LISTING

```
<160> NUMBER OF SEQ ID NOS: 7

<210> SEQ ID NO 1
<211> LENGTH: 5
<212> TYPE: PRT
```

```
<213> ORGANISM: Artificial
<220> FEATURE:
<223> OTHER INFORMATION: Synthetic peptide

<400> SEQUENCE: 1

Cys Ile Asp Pro Cys
1               5

<210> SEQ ID NO 2
<211> LENGTH: 6
<212> TYPE: PRT
<213> ORGANISM: Artificial
<220> FEATURE:
<223> OTHER INFORMATION: Synthetic peptide

<400> SEQUENCE: 2

Cys Ile Pro His Phe Cys
1               5

<210> SEQ ID NO 3
<211> LENGTH: 5
<212> TYPE: PRT
<213> ORGANISM: Artificial
<220> FEATURE:
<223> OTHER INFORMATION: Synthetic peptide

<400> SEQUENCE: 3

Cys Val Ala Gly Cys
1               5

<210> SEQ ID NO 4
<211> LENGTH: 42
<212> TYPE: PRT
<213> ORGANISM: Homo sapiens

<400> SEQUENCE: 4

Pro Ser Ser Val Ile Asp Ala Leu Gln Tyr Lys Leu Glu Gly Thr Thr
1               5                   10                  15

Arg Leu Thr Arg Lys Arg Gly Leu Lys Leu Ala Thr Ala Leu Ser Leu
            20                  25                  30

Ser Asn Lys Phe Val Glu Gly Ser Pro Ser
            35                  40

<210> SEQ ID NO 5
<211> LENGTH: 19
<212> TYPE: PRT
<213> ORGANISM: Homo sapiens

<400> SEQUENCE: 5

Val Asp Arg Val Arg Leu Ala Ser His Leu Arg Lys Leu Arg Lys Arg
1               5                   10                  15

Leu Leu Arg

<210> SEQ ID NO 6
<211> LENGTH: 59
<212> TYPE: PRT
<213> ORGANISM: Homo sapiens

<400> SEQUENCE: 6

Arg Arg Pro Asp Phe Cys Leu Glu Pro Pro Tyr Thr Gly Pro Cys Lys
1               5                   10                  15

Ala Arg Ile Ile Arg Tyr Phe Tyr Asn Ala Lys Ala Gly Leu Cys Gln
            20                  25                  30
```

```
Thr Phe Val Tyr Gly Gly Cys Arg Ala Lys Arg Asn Asn Phe Lys Ser
        35                  40                  45

Ala Glu Asp Cys Met Arg Thr Cys Gly Gly Ala
    50                  55

<210> SEQ ID NO 7
<211> LENGTH: 4
<212> TYPE: PRT
<213> ORGANISM: Artificial
<220> FEATURE:
<223> OTHER INFORMATION: Synthetic peptide

<400> SEQUENCE: 7

Lys Lys Gln Asn
1
```

US 9,534,016 B2

NETRIN LOOP PEPTIDE MIMETICS AND USES THEREOF

CROSS-REFERENCE TO RELATED APPLICATIONS

This application is a 371 National Phase of PCT/US2012/066676, filed on Nov. 27, 2012, which claims benefit of and priority to U.S. Ser. No. 61/563,914, filed Nov. 28, 2011, which is incorporated herein by reference in its entirety for all purposes.

STATEMENT AS TO RIGHTS TO INVENTIONS MADE UNDER FEDERALLY SPONSORED RESEARCH AND DEVELOPMENT

[Not Applicable]

BACKGROUND

Alzheimer's disease (AD), the most common form of dementia, is a progressive neurodegenerative disorder characterized by extracellular deposits of A peptide in senile plaques, intraneuronal neurofibrillary tangles, synapse loss, and cognitive decline (Hansen and Terry (1997) *Neurobiol. Aging,* 18: S71-73). It is widely believed that the accumulation of Aβ, a small peptide with a high propensity to form oligomers and aggregates, is central to the pathogenesis of AD. Aβ derives from the proteolytic cleavage of the transmembrane protein, APP (Koo (2002) *Traffic* 3(11): 763-770). Although a considerable amount is known about interacting proteins and processing events for APP, the physiological role(s) of APP and its related family members, APLP1 and APLP2 (amyloid precursor-like proteins 1 and 2), is still poorly understood (Koo (2002) *Traffic* 3(11): 763-770; Williamson et al. (1996) *J. Biol. Chem.,* 271: 31215-31221). APP has been proposed to function in cell adhesion and motility, as well as synaptic transmission and plasticity (for a review, see Turner et al. (2003) *Prog. Neurobiol.* 70: 1-32).

The cloning and characterization of APP revealed that it possesses many features reminiscent of a membrane-anchored receptor. However, to date, no clear candidate has emerged as the major ligand triggering APP-mediated signal transduction at least in part because the signal transduction mediated by APP has remained incompletely understood.

SUMMARY

In certain embodiments peptides are identified of peptides based on the loop structures of netrin-1. These "loop interaction peptides" have the ability to effect APP signaling based on their effect on sAPPα, the sAPPα/Aβ$_{42}$ ratio, and/or intracellular ERK phosphorylation. In various embodiments the peptides are also able to switch APP processing from aberrant to normal. Accordingly it is believed that the peptides disclosed herein are useful in the treatment and prophylaxis of various pathologies associated with Aβ formation and/or with APP processing.

In certain embodiments cyclic peptides are provided where the peptide is a pentapeptide comprising the formula: $C^1$-$X^2$-$X^3$-$X^4$-$C^5$, where $C^1$ and $C^5$ are independently selected cysteines or cysteine analogues, where the cysteines or cysteine analogs are attached to each other by a linkage that does not comprise $X^2$, $X^3$, and $X^4$; $X^2$, $X^3$, and $X^4$ are independently selected amino acids; and the peptide, when administered to a cell alters APP signaling and/or switches APP processing from aberrant to normal. In certain embodiments the cysteines or cysteine analogs are selected from the group consisting of cysteine, homocysteine, norcysteine, glutathione, acetylcysteine, cysteamine, D-penicillamine, and L-cysteine ethyl ester. In certain embodiments the cysteines or cysteine analogs are selected from the group consisting of cysteine, homocysteine, and norcysteine. In certain embodiments $X^2$-$X^3$ and/or $X^3$-$X^4$ are independently selected from the amino acid pairs listed in Table 5. In various embodiments $X^4$ is selected from the amino acids listed in Table 1. In certain embodiments, one or more, two or more, or all of $X^2$, $X^3$, and $X^4$ are naturally occurring amino acids. In certain embodiments $X^2$ is I or P or V, or conservative substitutions thereof, or $X^2$ is I or P, and/or $X^3$ is D or H or A, or conservative substitutions thereof, or $X^3$ is D or H, and/or $X^4$ is P or F or G, or conservative substitutions thereof, or $X^4$ is P or F. In certain embodiments -$X^2$-$X^3$-$X^4$- is -I-P-D- or -P-F-H-, or -V-A-G-. In certain embodiments $X^1$ and $X^5$ both have a side chain bearing an SH group (prior to cyclization). In certain embodiments $X^1$ and/or $X^5$ are cysteine. In certain embodiments the linkage comprises a disulfide bond. In certain embodiments the linkage comprises a polyethylene glycol (PEG). In certain embodiments the peptides described herein exclude an Arg-Gly-Asp motif. In certain embodiments the peptides described herein further comprises one or more protecting groups. In certain embodiments the protecting group(s) are independently selected from the group consisting of dansyl, acetyl, amide, and 3 to 20 carbon alkyl groups, Fmoc, Tboc, 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene) ethyl (Dde), 2,6-dichlorobenzyl (2,6-DiCl-Bzl), 2-chlorobenzyloxycarbonyl (2-Cl-Z), 2-bromobenzyloxycarbonyl (2-Br-Z), Benzyloxymethyl (Bom), t-butoxycarbonyl (Boc), cyclohexyloxy (cHxO), t-butoxymethyl (Bum), t-butoxy (tBuO), t-Butyl (tBu), Acetyl (Ac), and Trifluoroacetyl (TFA). In certain embodiments the protecting group is an N-terminal protecting group selected from the group consisting of acetyl, dansyl, propionyl, and a 3 to 20 carbon alkyl.

In certain embodiments the peptide is attached (e.g., chemically conjugated or provided as a fusion protein) to a "targeting/delivery" moiety that targets or facilitates transport across the blood brain barrier thereby forming a chimeric construct. In certain embodiments the "targeting/delivery" moiety is a receptor binding domain of a moiety selected from the group consisting ApoB, ApoE, aprotinin, lipoprotein lipase, PAI-1, pseudomonas exotoxin A, transferrin, α2-macroglobulin, insulin-like growth factor, insulin, a positively charged poly-peptides (e.g., polyargine). In certain embodiments the moiety is a peptide selected from the group consisting of PSSVIDALQYKLEGTTRLTRKRG LKLATALS LSNKFVEGSPS (SEQ ID NO:4), VDRVR-LASHLRKLRKRLLR (SEQ ID NO:5), and RRPDFCLEP-PYTGPCKARIIRYFYN AKAGLCQTFVYGGCRA KRNNF KSAED CMRTCGG A (SEQ ID NO:6).

In certain embodiments the peptide or chimeric construct is formulated for administration to a mammal via a route selected from the group consisting of oral administration, nasal administration, administration by inhalation, intracerberalvetricular administration (ICV), intrparenchymal administration, rectal administration, intraperitoneal injection, intravascular injection, subcutaneous injection, transcutaneous administration, and intramuscular injection.

In certain embodiments methods of increasing sAPPα or increasing the ratio of sAPPα/Aβ42 in a mammal are provided where the method comprises administering to the mammal a netrin loop peptide and/or peptide formulation as described herein in an amount sufficient to increase sAPPα and/or increase the ratio of sAPPα/Aβ42 in the mammal. In certain embodiments methods of mitigating in a mammal one or more symptoms associated with a disease characterized by amyloid deposits in the brain, or delaying or preventing the onset of the symptoms are provided where the methods comprise administering to the mammal a netrin loop peptide and/or peptide formulation in an amount sufficient to mitigate one or more symptoms associated with a disease characterized by amyloid deposits in the brain. Methods of reducing the risk, lessening the severity, or delaying the progression or onset of a disease characterized by beta-amyloid deposits in the brain of a mammal are also provided where the methods comprise administering to the mammal a netrin loop peptide and/or peptide formulation in an amount sufficient to lessen the severity, or delaying the progression or onset of a disease characterized by beta-amyloid deposits in the brain. In certain embodiments the disease is a disease selected from the group consisting of Alzheimer's disease, age-related macular degeneration (AMD), Cerebrovascular dementia, Parkinson's disease, Huntington's disease, and Cerebral amyloid angiopathy. Also provided are methods of preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease in a mammal where the method comprises administering to the mammal a netrin loop peptide and/or peptide formulation in an amount sufficient to prevent or delay the onset of a pre-Alzheimer's condition and/or cognitive dysfunction, and/or to ameliorate one or more symptoms of a pre-Alzheimer's condition and/or cognitive dysfunction, or to prevent or delay the progression of a pre-Alzheimer's condition or cognitive dysfunction to Alzheimer's disease. In various embodiments methods are provided for promoting the processing of amyloid precursor protein (APP) by the non-amyloidogenic pathway as characterized by increasing sAPPα and/or the sAPPα/Aβ42 ratio in a mammal, where the methods comprise administering to the mammal a netrin loop peptide and/or peptide formulation in an amount sufficient to promote the processing of amyloid precursor protein (APP) by the non-amyloidogenic pathway as characterized by increasing sAPPα and/or the sAPPα/Aβ42 ratio in a mammal. In certain embodiments methods are provided for inducing ERK phosphorylation in a cell and/or switching APP processing from aberrant to normal where the methods comprise administering to the cell a mammal a netrin loop peptide and/or peptide formulation in an amount sufficient to induce ERK phosphorylation in the cell and/or to switching APP processing from aberrant to normal. In certain embodiments methods are provided for mitigating one or more symptoms of a disease characterized by amyloid plaque formation and/or slowing the onset or progression of the disease where the methods comprise administering to a subject in need thereof a netrin loop peptide and/or peptide formulation, in an amount sufficient to mitigate one or more symptoms and/or to slow the onset or progression of the disease. In various embodiments of these methods the mammal is a human (e.g., a human diagnosed as having or at risk for MCI or Alzheimer's disease). In various embodiments of these methods the administering inhibits the onset or progression of one or more symptoms of Alzheimer's disease. In various embodiments of these methods the administering results in an increase in sAPPα level. In various embodiments of these methods the administering results in an increase in the ratio of sAPPα/Aβ42. In various embodiments of these methods the administering comprises administering the peptide to a mammal via a route selected from the group consisting of oral administration, nasal administration, administration by inhalation, intracerberalvetricular (ICV) administration, intrparenchymal administration, rectal administration, intraperitoneal injection, intravascular injection, subcutaneous injection, transcutaneous administration, intramuscular injection, and intracranial cannulation. In various embodiments of these methods the administering to a cell comprises administering to a cell in vitro. In various embodiments of these methods the administering to a cell comprises administering to a cell in vivo. In various embodiments of these methods the cell is a neural cell. In various embodiments of these methods the mammal is a human diagnosed as having or at risk for Alzheimer's disease. In various embodiments of these methods the administering inhibits the onset or progression of one or more symptoms of MIC or Alzheimer's disease. In various embodiments of these methods the administering results in an increase in sAPPα level. In various embodiments of these methods the administering results in an increase in the ratio of sAPPα/Aβ42. In various embodiments of these methods the administering comprises administering the peptide to a mammal via a route selected from the group consisting of oral administration, nasal administration, administration by inhalation, intracerberalvetricular (ICV) administration, intrparenchymal administration, rectal administration, intraperitoneal injection, intravascular injection, subcutaneous injection, transcutaneous administration, intramuscular injection, and intracranial cannulation In various embodiments of these methods administration of the compound delays or prevents the progression of MCI to Alzheimer's disease. In various embodiments of these methods the mammal is diagnosed as having Alzheimer's disease. In various embodiments of these methods the mammal is at risk of developing Alzheimer's disease. In various embodiments of these methods the mammal has a familial risk for having Alzheimer's disease. In various embodiments of these methods the mammal has a familial Alzheimer's disease (FAD) mutation. In various embodiments of these methods the mammal has the APOE ε4 allele. In various embodiments of these methods the mammal is free of and does not have genetic risk factors of for a neurological disorder not associated with or characterized by the formation of beta-amyloid plaques. In various embodiments of these methods the mammal is not diagnosed as having or at risk schizophrenia or other neuropsychiatric disorders. In various embodiments of these methods the mammal does not have a neurological disease or disorder other than Alzheimer's disease. In various embodiments of these methods the mammal is not diagnosed as having or at risk for a neurological disease or disorder other than Alzheimer's disease. In various embodiments of these methods the mitigation comprises a reduction in the CSF of levels of one or more components selected from the group consisting of Tau, phospho-Tau (pTau), APPneo, soluble Aβ40 and soluble Aβ42. In various embodiments of these methods the mitigation comprises a reduction of the plaque load in the brain of the mammal. In various embodiments of these methods the mitigation comprises a reduction in the rate of plaque formation in the brain of the mammal. In various embodiments of these methods the mitigation comprises an improvement in the cognitive abilities of the mammal. In various embodiments of these methods the mammal is a human and the mitigation comprises a perceived improvement in quality of life by the human. In various embodiments of these methods the composition is administered orally. In various embodiments of these methods the administering is over a period of at least three weeks or over a period of at least 6 weeks, or over a period of at least 3 months, or over a period of at least 6 months, or over a period of at least 1 year, or at least 2 years, or at least 3 years, or at least 5 years. In various embodiments of these methods the netrin peptide(s) are formulated for administration via a route selected from the group consisting of isophoretic delivery, transdermal delivery, aerosol administration, administration via inhalation, oral administration, intravenous administration, and rectal administration. In various embodiments of these methods the peptide is administered via a route selected from the group consisting of isophoretic delivery, transdermal delivery, aerosol administration, administration via inhalation, oral administration, intravenous administration, and rectal administration. In various embodiments of these methods the peptide(s) are administered in conjunction with an agent selected from the group consisting of a tropinol ester, tropisetron, a tropisetron analog, disulfiram, a disulfiram analog, honokiol, a honokiol analog, nimetazepam, a nimetazepam analog, donepezil, rivastigmine, galantamine, tacrine, memantine, solanezumab, bapineuzmab, alzemed, flurizan, ELND005, valproate, semagacestat, rosiglitazone, phenserine, cernezumab, dimebon, egcg, gammagard, PBT2, PF04360365, NIC5-15, bryostatin-1, AL-108, nicotinamide, EHT-0202, BMS708163, NP12, lithium, ACC001, AN1792, ABT089, NGF, CAD106, AZD3480, SB742457, AD02, huperzine-A, EVP6124, PRX03140, PUFA, HF02, MEM3454, TTP448, PF-04447943, GSK933776, MABT5102A, talsaclidine, UB311, begacestat, R1450, PF3084014, V950, E2609, MK0752, CTS21166, AZD-3839, LY2886721, CHF5074, an anti-inflammatory, dapsone, an anti-TNF antibody, and a statin.

Definitions

The term "peptide" as used herein refers to a polymer of amino acid residues. In certain embodiments the peptide ranges in length from 2 to about 500, 300, 100, or 50 residues. In certain embodiments the peptide ranges in length from about 2, 3, 4, 5, 7, 9, 10, or 11 residues to about 50, 45, 40, 45, 30, 25, 20, or 15 residues. In certain embodiments the peptide ranges in length from about 5 residues to about 15, 12, 8, 10, or 7 residues. In certain embodiments the amino acid residues comprising the peptide are "L-form" amino acid residues, however, it is recognized that in various embodiments, "D" amino acids can be incorporated into the peptide. Peptides also include amino acid polymers in which one or more amino acid residues is an artificial chemical analogue of a corresponding naturally occurring amino acid, as well as naturally occurring amino acid polymers. In addition, the term applies to amino acids joined by a peptide linkage or by other, "modified linkages" (e.g., where the peptide bond is replaced by an α-ester, a β-ester, a thioamide, phosphonamide, carbomate, hydroxylate, and the like (see, e.g., Spatola, (1983) *Chem. Biochem. Amino Acids and Proteins* 7: 267-357), where the amide is replaced with a saturated amine (see, e.g., U.S. Pat. No. 4,496,542, and Kaltenbronn et al., (1990) Pp. 969-970 in Proc. 11th American Peptide Symposium, ESCOM Science Publishers, The Netherlands, and the like)).

The term "residue" as used herein refers to natural, synthetic, or modified amino acids. Various amino acid analogues include, but are not limited to 2-aminoadipic acid, 3-aminoadipic acid, beta-alanine (beta-aminopropionic acid), 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4 diaminobutyric acid, desmosine, 2,2'-diaminopimelic acid, 2,3-diaminopropionic acid, n-ethylglycine, n-ethylasparagine, hydroxylysine, allo-hydroxylysine, 3-hydroxyproline, 4-hydroxyproline, isodesmosine, allo-isoleucine, n-methylglycine, sarcosine, n-methylisoleucine, 6-n-methyllysine, n-methylvaline, norvaline, norleucine, ornithine, and the like. A number of illustrative amino acids are shown in Table 1. These modified amino acids are illustrative and not intended to be limiting.

TABLE 1

Illustrative amino acids and abbreviations.

| Amino acid name | Abbreviation | Single letter |
| --- | --- | --- |
| 4-aminobutanoic acid (Piperidinic acid) | GABA | |
| Epsilon-aminocaproic acid | EACA | |
| Lys(N(epsilon))-trifluoroacetyl) | K[TFA] | |
| tetrahydroisoquinoline-3-carboxylic acid | D-TIC | O |
| 3-(1-naphthyl)alanine | 1-Nal | |
| 3-(2-naphthyl)alanine | 2-Nal | |
| 3-hydroxyproline | 3Hyp | |
| 3-(pyridyl)alanine | 3-Pal | |
| 4-aminobutyric acid, piperidinic acid | 4Abu | |
| 4-hydroxyproline | 4Hyp | |
| 2,4-diaminobutyric acid | A2bu | |
| 2,3-diaminopropionic acid | A2pr | |
| 2-aminoadipic acid | Aad | |
| 6-aminohexanoic acid | aAhx | |
| 2-azabicyclo[2.2.2]octane-3-carboxylic acid | Abo | |
| α-aminobutyric acid | Abu | |
| 4-aminocyclohexanecarboxylic acid | ACCA | |
| 6-aminocaproic acid | Acp | |
| 2-aminoheptanoic acid | Ahe | |
| ($NH_2$—$(CH_2)_5$—COOH) | Ahx | J |
| allo-Hydroxylysine | aHyl | |
| 2-Aminoisobutfyric acid | Aib | |
| α-aminoisobutyric acid | Aib | |
| 2-aminoindan-2-carboxylic acid | Aic | |
| allo-isoleucine | aIle | |
| alanine | Ala | A |
| 2-aminopimelic acid | Apm | |
| arginine | Arg | R |
| asparagine | Asn | N |
| aspartic acid | Asp | D |
| 2-aminotetralin-2-carboxylic acid | Atc | |
| 5-aminopentanoic acid | Ava | |
| azetidine-2-carboxylic acid | Aze | |
| 3-aminoadipic acid | bAad | |
| 3-aminoisobutyric acid | bAib | |
| beta-alanine, beta-aminoproprionic acid | bAla | |
| 3-cyclohexylalanine | Cha | |
| α-cyclopentylglycine | Cpg | |
| 1-mercaptocyclohexaneacetic acid, or β-mercapto-β,β-cyclopenta-methylene propionic acid, or Pmp (below) | Cpp | |
| cis-3-(4-pyrazinylcarbonylaminocyclohexyl)alanine | cPzACAla | |
| Cysteine | Cys | C |
| 2,3-diaminopropionic acid | Dap | |
| 3-(2-dibenzofuranyl)alanine | Dbf | |

TABLE 1-continued

Illustrative amino acids and abbreviations.

| Amino acid name | Abbreviation | Single letter |
|---|---|---|
| 2,4-Diaminobutyric acid | Dbu | |
| Desmosine | Des | |
| 3,3-diphenylalanine | Dip | |
| a,a-diphenylglycine | Dph | |
| 2,2'-Diaminopimelic acid | Dpm | |
| 2,3-Diaminoproprionic acid | Dpr | |
| N-Ethylasparagine | EtAsn | |
| N-Ethylglycine | EtGly | |
| (NH$_2$—(CH$_2$)$_3$—COOH) | gAbu | |
| glutamine | Gln | Q |
| glutamic acid | Glu | E |
| glycine | Gly | G |
| phenylglycine | Gly(Ph) | |
| homoarginine | Har | |
| homocysteine | Hcy | |
| α-hydroxyisobutyric acid | Hib | |
| histidine | His | H |
| homoserine | Hse | — |
| hydroxylysine | Hyl | |
| trans-4-hydroxyproline | Hyp | |
| isodesmosine | Ide | |
| isoleucine | Ile | I |
| isovaline | Iva | |
| leucine | Leu | L |
| lysine | Lys | K |
| N-methylglycine, sarcosine | MeGly | |
| N-methylisoleucine | MeIle | |
| 6-N-methyllysine | MeLys | |
| methionine | Met | M |
| methionine sulfoxide | Met (O) | — |
| methionine methylsulfonium | Met (S—Me) | — |
| N-methylvaline | MeVal | |
| trans-4-mercaptoproline | Mpt | |
| β-(1'-naphthyl)alanine | Nap | |
| norleucine | Nle | — |
| norvaline | Nva | |
| octahydroindolecarboxylic acid | Oic | |
| D-phenyltyrosine | Opt | |
| ornithine | Orn | |
| penicillamine | Pen | |
| phenylalanine | Phe | F |
| phenylglycine | Phg | |
| pipecolic acid | Pip | |
| 3,3-pentamethylene-(3-mercaptopropionic acid, or Cpp (above) | Pmp | |
| proline | Pro | P |
| 3-(3-quinolyl)alanine | Qal | |
| quinoline-2-carboxamide | Qua | |
| sarcosine | Sar | |
| serine | Ser | S |
| β-thienylalanine | Thi | |
| threonine | Thr | T |
| 1,2,3,4-tetrahydroisoquinoline-3-carboxylic acid | Tic | |
| tryptophan | Trp | W |
| tyrosine | Tyr | Y |
| valine | Val | V |
| β-Alanine (NH$_2$—CH$_2$—CH$_2$—COOH) | βAla | |

In addition, specific examples of amino acid analogs and mimetics can be found described in, for example, Roberts and Vellaccio, *The Peptides: Analysis, Synthesis, Biology*, Eds. Gross and Meinhofer, Vol. 5, p. 341, Academic Press, Inc., New York, N.Y. (1983). Other examples include per-alkylated amino acids, particularly permethylated amino acids. See, for example, *Combinatorial Chemistry*, Eds. Wilson and Czarnik, Ch. 11, p. 235, John Wiley & Sons Inc., New York, N.Y. (1997). Yet other examples include amino acids whose amide portion (and, therefore, the amide backbone of the resulting peptide) has been replaced, for example, by a sugar ring, steroid, benzodiazepine or carbo cycle (see, e.g., *Burger's Medicinal Chemistry and Drug Discovery*, Ed. Manfred E. Wolff, Ch. 15, pp. 619-620, John Wiley & Sons Inc., New York, N.Y. (1995), and the like). Methods for synthesizing peptides, polypeptides, peptidomimetics and polypeptides are well known in the art (see, for example, U.S. Pat. No. 5,420,109; M. Bodanzsky, *Principles of Peptide Synthesis* (1st ed. & 2d rev. ed.), Springer-Verlag, New York, N.Y. (1984 & 1993), see Chapter 7; Stewart and Young, *Solid Phase Peptide Synthesis*, (2d ed.), Pierce Chemical Co., Rockford, Ill. (1984).

"β-peptides" comprise of "β amino acids", which have their amino group bonded to the β carbon rather than the α-carbon as in the 20 standard biological amino acids. The only commonly naturally occurring β amino acid is β-alanine.

Peptoids, or N-substituted glycines, are a specific subclass of peptidomimetics. They are closely related to their natural peptide counterparts, but differ chemically in that their side chains are appended to nitrogen atoms along the molecule's backbone, rather than to the α-carbons (as they are in natural amino acids).

The terms "conventional" and "natural" as applied to peptides herein refer to peptides, constructed only from the naturally-occurring amino acids: Ala, Cys, Asp, Glu, Glu, Phe, Gly, His, Ile, Lys, Leu, Met, Asn, Pro, Gln, Arg, Ser, Thr, Val, Tip, and Tyr. A compound of the invention "corresponds" to a natural peptide if it elicits a biological activity related to the biological activity and/or specificity of the naturally occurring peptide. The elicited activity may be the same as, greater than or less than that of the natural peptide. In various embodiments, such a peptoid will have an essentially corresponding monomer sequence, where a natural amino acid is replaced by an N-substituted glycine derivative, if the N-substituted glycine derivative resembles the original amino acid in hydrophilicity, hydrophobicity, polarity, etc. The correspondence need not be exact: for example, N-(2-hydroxyethyl)glycine may substitute for Ser, Thr, Cys, and Met; N-(2-methylprop-1-yl)glycine may substitute for Val, Leu, and Ile. In general, one may use an N-hydroxyalkyl-substituted glycine to substitute for any polar amino acid, an N-benzyl- or N-aralkyl-substituted glycine to replace any aromatic amino acid (e.g., Phe, Trp, etc.), an N-alkyl-substituted glycine such as N-butylglycine to replace any nonpolar amino acid (e.g., Leu, Val, Ile, etc.), and an N-(aminoalkyl)glycine derivative to replace any basic polar amino acid (e.g., Lys and Arg).

Where an amino acid sequence is provided herein, L-, D-, or beta amino acid versions of the sequence are also contemplated as well as retro, inversion, and retro-inversion isoforms. Non-protein backbones, such as PEG and other backbones are also contemplated.

In certain embodiments, conservative substitutions of the amino acids comprising any of the sequences described herein are contemplated. In various embodiments one, two, three, four, or five different residues are substituted. The term "conservative substitution" is used to reflect amino acid substitutions that do not substantially alter the activity (e.g., antimicrobial activity and/or specificity) of the molecule. Typically conservative amino acid substitutions involve substitution one amino acid for another amino acid with similar chemical properties (e.g. charge or hydrophobicity). Certain conservative substitutions include "analog substitutions" where a standard amino acid is replaced by a non-standard (e.g., rare, synthetic, etc) amino acid differing minimally from the parental residue. Amino acid analogs are considered to be derived synthetically from the standard amino acids without sufficient change to the structure of the parent, are isomers, or are metabolite precursors. Examples of such "analog substitutions" include, but are not limited to, 1) Lys-Orn, 2) Leu-Norleucine, 3) Lys-Lys[TFA], 4) Phe-Phe[Gly], and 5) δ-amino butylglycine-ξ-amino hexylglycine, where Phe[gly] refers to phenylglycine (a Phe derivative with a H rather than $CH_3$ component in the R group), and Lys[TFA] refers to a Lys where a negatively charged ion (e.g., TFA) is attached to the amine R group. Other conservative substitutions include "functional substitutions" where the general chemistries of the two residues are similar, and can be sufficient to mimic or partially recover the function of the native peptide. Strong functional substitutions include, but are not limited to 1) Gly/Ala, 2) Arg/Lys, 3) Ser/Tyr/Thr, 4) Leu/Ile/Val, 5) Asp/Glu, 6) Gln/Asn, and 7) Phe/Trp/Tyr, while other functional substitutions include, but are not limited to 8) Gly/Ala/Pro, 9) Tyr/His, 10) Arg/Lys/His, 11) Ser/Thr/Cys, 12) Leu/Ile/Val/Met, and 13) Met/Lys (special case under hydrophobic conditions). Various "broad conservative substations" include substitutions where amino acids replace other amino acids from the same biochemical or biophysical grouping. This is similarity at a basic level and stems from efforts to classify the original 20 natural amino acids. Such substitutions include 1) nonpolar side chains: Gly/Ala/Val/Leu/Ile/Met/Pro/Phe/Trp, and/or 2) uncharged polar side chains Ser/Thr/Asn/Gln/Tyr/Cys. In certain embodiments broad-level substitutions can also occur as paired substitutions. For example, Any hydrophilic neutral pair [Ser, Thr, Gln, Asn, Tyr, Cys]+[Ser, Thr, Gln, Asn, Tyr, Cys] can may be replaced by a charge-neutral charged pair [Arg, Lys, His]+[Asp, Glu]. The following six groups each contain amino acids that, in certain embodiments, are typical conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K), Histidine (H); 5) Isoleucine (I), Leucine (L), Methionine (M), Valine (V); and 6) Phenylalanine (F), Tyrosine (Y), Tryptophan (W). Where amino acid sequences are disclosed herein, amino acid sequences comprising, one or more of the above-identified conservative substitutions are also contemplated.

As used herein, the phrase "a subject in need thereof" refers to a subject, as described infra, that suffers or is at a risk of suffering (e.g., pre-disposed such as genetically pre-disposed) from the diseases or conditions listed herein.

The terms "subject," "individual," and "patient" may be used interchangeably and refer to a mammal, preferably a human or a non-human primate, but also domesticated mammals (e.g., canine or feline), laboratory mammals (e.g., mouse, rat, rabbit, hamster, guinea pig), and agricultural mammals (e.g., equine, bovine, porcine, ovine). In various embodiments, the subject can be a human (e.g., adult male, adult female, adolescent male, adolescent female, male child, female child) under the care of a physician or other health worker in a hospital, psychiatric care facility, as an outpatient, or other clinical context. In certain embodiments, the subject may not be under the care or prescription of a physician or other health worker.

An "effective amount" refers to an amount effective, at dosages and for periods of time necessary, to achieve the desired therapeutic or prophylactic result. A "therapeutically effective amount" of a multi-component formulation, optionally in combination with one or more pharmaceuticals, may vary according to factors such as the disease state, age, sex, and weight of the individual, the pharmaceutical (and dose thereof) when used in combination with pharmaceutical, and the ability of the treatment to elicit a desired response in the individual. A therapeutically effective amount is also one in which any toxic or detrimental effects of a treatment are substantially absent or are outweighed by the therapeutically beneficial effects. The term "therapeutically effective amount" refers to an amount of an active agent or composition comprising the same that is effective to "treat" a disease or disorder in a mammal (e.g., a patient). In one embodiment, a therapeutically effective amount is an amount sufficient to improve at least one symptom associated with a neurological disorder, improve neurological function, improve cognition, or one or more markers of a neurological disease, or to enhance the efficacy of one or more pharmaceuticals administered for the treatment or prophylaxis of a neurodegenerative pathology. In certain embodiments, an effective amount is an amount sufficient alone, or in combination with a pharmaceutical agent to prevent advancement or the disease, delay progression, or to cause regression of a disease, or which is capable of reducing symptoms caused by the disease, A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount is less than the therapeutically effective amount.

The terms "treatment," "treating," or "treat" as used herein, refer to actions that produce a desirable effect on the symptoms or pathology of a disease or condition, particularly those that can be effected utilizing the multi-component formulation(s) described herein, and may include, but are not limited to, even minimal changes or improvements in one or more measurable markers of the disease or condition being treated. Treatments also refers to delaying the onset of, retarding or reversing the progress of, reducing the severity of, or alleviating or preventing either the disease or condition to which the term applies, or one or more symptoms of such disease or condition. "Treatment," "treating," or "treat" does not necessarily indicate complete eradication or cure of the disease or condition, or associated symptoms thereof. In one embodiment, treatment comprises improvement of at least one symptom of a disease being treated. The improvement may be partial or complete. The subject receiving this treatment is any subject in need thereof. Exemplary markers of clinical improvement will be apparent to persons skilled in the art.

The term "mitigating" refers to reduction or elimination of one or more symptoms of that pathology or disease, and/or a reduction in the rate or delay of onset or severity of one or more symptoms of that pathology or disease, and/or the prevention of that pathology or disease.

As used herein, the phrases "improve at least one symptom" or "improve one or more symptoms" or equivalents thereof, refer to the reduction, elimination, or prevention of one or more symptoms of pathology or disease. Illustrative symptoms of pathologies treated, ameliorated, or prevented by the compositions described herein (e.g., tropinol esters and related esters) include, but are not limited to, reduction, elimination, or prevention of one or more markers that are characteristic of the pathology or disease (e.g., of total-Tau (tTau), phospho-Tau (pTau), APPneo, soluble Aβ40, pTau/Ap42 ratio and tTau/Ap42 ratio, and/or an increase in the CSF of levels of one or more components selected from the group consisting of Aβ42/Aβ40 ratio, Aβ42/Aβ38 ratio, sAPPα,βAPPα/βAPPβ ratio, βAPPα/Aβ40 ratio, βAPPα/Aβ42 ratio, etc.) and/or reduction, stabilization or reversal of one or more diagnostic criteria (e.g., clinical dementia rating (CDR)). Illustrative measures for improved neurological function include, but are not limited to the use of the mini-mental state examination (MMSE) or Folstein test (a questionnaire test that is used to screen for cognitive impairment), the General Practitioner Assessment of Cognition (GPCOG), a brief screening test for cognitive impairment described by Brodaty et al., (2002) *Geriatrics Society* 50(3): 530-534, and the like.

The phrase "cause to be administered" refers to the actions taken by a medical professional (e.g., a physician), or a person prescribing and/or controlling medical care of a subject, that control and/or determine, and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like. It will be recognized that in methods involving administration, "causing to be administered" is also contemplated. Thus, for example, where " . . . administering compound X . . . " is recited " . . . administering compound X or causing compound X to be administered . . . " may be contemplated.

BRIEF DESCRIPTION OF THE DRAWINGS

FIG. 1A illustrates netrin-1 structure based on a computational model, while

DETAILED DESCRIPTION

Figure 1A:
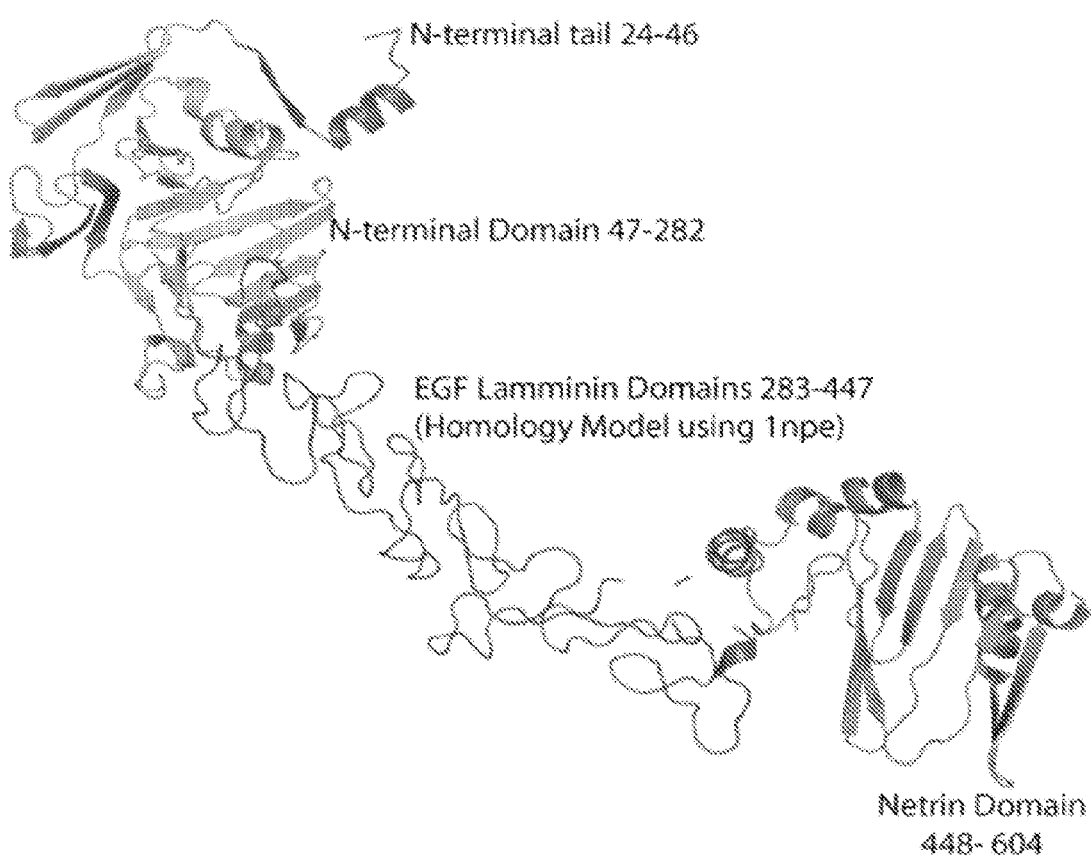

In certain embodiments this invention pertains to the identification of peptides based on the loop structures of netrin-1 that are referred to herein as loop-interaction peptides or simply "loop peptides". In certain embodiments the peptides are cyclic (cyclized) peptides. These loop interaction peptides have the ability to effect APP signaling based on their effect on sAPPα, the sAPPα/Aβ$_{42}$ ratio, and/or intracellular ERK phosphorylation. In various embodiments the peptides are also able to switch APP processing from aberrant to normal. Accordingly it is believed that the peptides disclosed herein are useful in the treatment and prophylaxis of various pathologies associated with Aβ formation and/or with APP processing.

Thus, in certain embodiments, methods are provided for reducing or inhibiting the onset and/or degree of beta amyloid peptide production and amyloid plaque formation associated with Alzheimer's Disease by administering to a subject (e.g., a subject diagnosed as having or at risk for a pathology characterized by abnormal APP processing, and/or Aβ formation, and/or amyloid plaque formation) one or more loop peptides as described herein.

The methods described herein are based, in part, on the discovery that the peptides described herein show efficacy in promoting processing of amyloid beta (Aβ) precursor protein ("APP") by the nonamyloidogenic ("anti-AD") pathway and/or in reducing or inhibiting processing of APP by the amyloidogenic ("pro-AD") pathway. Without being bound to a particular theory, this is believed to result in reduced production of Aβ, that may be deposited in amyloid plaques in the brain and the other pro-AD fragments known to result in neurotoxicity.

Accordingly, in various embodiments, the use of the peptides described herein alone, or in combination with other therapeutic agents, is contemplated in the modulation, and in particular in the reduction of amyloidogenic pathologies (e.g., Alzheimer's disease, age-related macular degeneration (AMD), Cerebrovascular dementia, Parkinson's disease, and the like). In certain embodiments, the peptides described herein are used to prevent or delay the onset of a pre-Alzheimer's condition and/or cognitive dysfunction, and/or to ameliorate one or more symptoms of a pre-Alzheimer's condition and/or cognitive dysfunction, and/or to prevent or delay the progression of a pre-Alzheimer's condition or cognitive dysfunction to Alzheimer's disease. In certain embodiments, the peptides described herein are used in a method of mitigating in a mammal one or more symptoms associated with a disease characterized by amyloid deposits in the brain, or delaying or preventing the onset of said symptoms. In certain embodiments, methods of reducing the risk, lessening the severity, or delaying the progression or onset of a disease characterized by beta-amyloid deposits in the brain of a mammal are also provided. In addition, methods of promoting the processing of amyloid precursor protein (APP) by the non-amyloidogenic pathway in a mammal are provided. In certain embodiments, methods of directly or indirectly inhibiting the C-terminal cleavage of APP resulting in the formation of APP-C31 peptide and APPneo (APP$_{664}$) in a mammal are provided.

Although the description provided herein references mainly Alzheimer's Disease, or pre-Alzheimer's conditions (e.g., MCI, and the like) any neurodegenerative condition and associated with beta amyloid plaque formation or Aβ peptide production is a candidate for prophylaxis and/or therapy that encompasses the compositions and methods described herein. In addition, conditions that known to overlap with Alzheimer's disease such that symptoms associated with Alzheimer's disease are present, for example, Lewy body dementia, can be targeted with the treatment and/or prophylactic methods described herein. Lewy bodies refer to abnormal structures within nerve cells of the brain and it is estimated that up to 40 percent of people with Alzheimer's have Lewy bodies in the neocortex. Cerebral amyloid angiopathy (CAA) refers to the deposition of β-amyloid in the media and adventitia of small- and mid-sized arteries (and less frequently, veins) of the cerebral cortex and the leptomeninges. It is a component of any disorder in which amyloid is deposited in the brain, and it is not associated with systemic amyloidosis. In addition it could be used in other diseases characterized by amyloidogenic proteins such as huntingtin of Huntingtin's disease (HD), alpha-synuclein of Parkinson's Disease, tau proteins of AD or frontal temporal lobe (FTD) disorder.

Typically each of these methods involve administering one or more peptides described herein, in an amount sufficient to produce the desired activity (e.g., mitigating one or more symptoms associated with a disease characterized by amyloid deposits in the brain, or delaying or preventing the onset of said symptoms, and/or reducing the risk, lessening the severity, or delaying the progression or onset of a disease characterized by beta-amyloid deposits in the brain of a mammal, and/or promoting the processing of amyloid precursor protein (APP) by the non-amyloidogenic pathway).

As indicated above, while the methods described herein are detailed primarily in the context of mild cognitive impairment (MCI) and Alzheimer's disease (AD) it is believed they can apply equally to other pathologies characterized by amyloidosis. Illustrative, but non-limiting list of conditions characterized by amyloid plaque formation are shown in Table 2.

Prophylaxis

In certain embodiments the peptides described herein are utilized in various prophylactic contexts. Thus, for example, ion certain embodiments, the active agent(s) (e.g., netrin loop peptides) can be used to prevent or delay the onset of a pre-Alzheimer's cognitive dysfunction, and/or to ameliorate one more symptoms of a pre-Alzheimer's condition and/or cognitive dysfunction, and/or to prevent or delay the progression of a pre-Alzheimer's condition and/or cognitive dysfunction to Alzheimer's disease.

Accordingly in certain embodiments, the prophylactic methods described herein are contemplated for subjects identified as "at risk" and/or as having evidence of early Alzheimer's Disease (AD) pathological changes, but who do not meet clinical criteria for MCI or dementia. Without being bound to a particular theory, it is believed that even this "preclinical" stage of the disease represents a continuum from completely asymptomatic individuals with biomarker evidence suggestive of AD-pathophysiological process(es)

TABLE 2

Illustrative, but non-limiting pathologies characterized by amyloid formation/deposition.

| Disease | Characteristic Protein | Abbreviation |
| --- | --- | --- |
| Alzheimer's disease | Beta amyloid | Aβ |
| Diabetes mellitus type 2 | IAPP (Amylin) | AIAPP |
| Parkinson's disease | Alpha-synuclein | |
| Transmissible spongiform encephalopathy e.g. Bovine spongiform encephalopathy | Prion | APrP |
| Huntington's Disease | Huntingtin | |
| Medullary carcinoma of the thyroid | Calcitonin | ACal |
| Cardiac arrhythmias, Isolated atrial amyloidosis | Atrial natriuretic factor | AANF |
| Atherosclerosis | Apolipoprotein AI | AApoA1 |
| Rheumatoid arthritis | Serum amyloid A | AA |
| Aortic medial amyloid | Medin | AMed |
| Prolactinomas | Prolactin | APro |
| Familial amyloid polyneuropathy | Transthyretin | ATTR |
| Hereditary non-neuropathic systemic amyloidosis | Lysozyme | ALys |
| Dialysis related amyloidosis | Beta 2 microglobulin | Aβ2M |
| Finnish amyloidosis | Gelsolin | AGel |
| Lattice corneal dystrophy | Keratoepithelin | AKer |
| Cerebral amyloid angiopathy | Beta amyloid[15] | Aβ |
| Cerebral amyloid angiopathy (Icelandic type) | Cystatin | ACys |
| systemic AL amyloidosis | Immunoglobulin light chain AL[14] | AL |
| Sporadic Inclusion Body Myositis Age-related macular degeneration (AMD) Cerebrovascular dementia | S-IBM | none |

Subjects who can Benefit from the Present Methods

Subjects/patients amenable to treatment using the methods described herein include individuals at risk of disease (e.g., a pathology characterized by amyloid plaque formation) but not showing symptoms, as well as subjects presently showing symptoms. Accordingly, certain subjects include subjects at increased risk for the onset of a pre-Alzheimer's condition and/or cognitive dysfunction (e.g., MCI) and/or subjects diagnosed as having a pre-Alzheimer's condition and/or cognitive dysfunction (e.g., MCI).

Accordingly, in various embodiments, therapeutic and/or prophylactic methods are provided that utilize the active agent(s) (e.g., the peptides described herein) are provided. Typically the methods involve administering one or more netrin loop peptides to a subject (e.g., to a human in need thereof) in an amount sufficient to realize the desired therapeutic or prophylactic result.

(abbreviated as AD-P, see, e.g., Sperling et al., (2011) *Alzheimer's & Dementia,* 1-13) at risk for progression to AD dementia to biomarker-positive individuals who are already demonstrating very subtle decline but not yet meeting standardized criteria for MCI (see, e.g., Albert et al., (2011) *Alzheimer's and Dementia,* 1-10 (doi: 10.1016/j.jalz.2011.03.008)).

This latter group of individuals might be classified as "not normal, not MCI" but can be designated "pre-symptomatic" or "pre-clinical" or "asymptomatic" or "premanifest"). In various embodiments, this continuum of pre-symptomatic AD can also encompass (1) individuals who carry one or more apolipoprotein E (APOE) ε4 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

Figure 3:
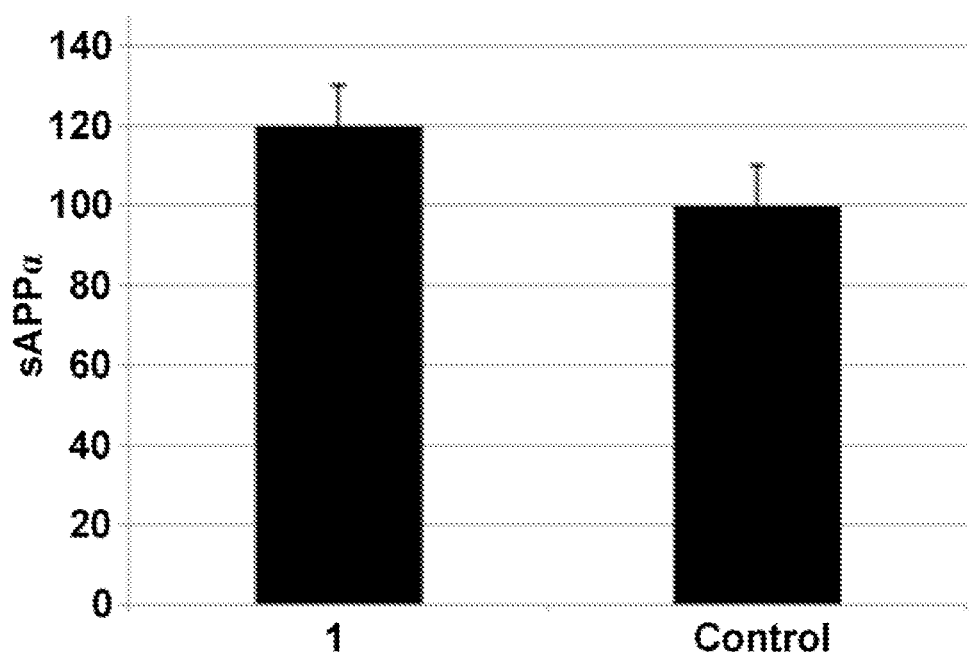
FIG. 3 illustrates the effect of the C-I-D-P-C peptide (SEQ ID NO:1, Formula 1) in increasing sAPPα levels as measured by ALPHALISA assay.

A biomarker model has been proposed in which the most widely validated biomarkers of AD-P become abnormal and likewise reach a ceiling in an ordered manner (see, e.g., Jack et al., (2010) *Lancet Neurol.*, 9: 119-128). This biomarker model parallels proposed pathophysiological sequence of (pre-AD/AD), and is relevant to tracking the preclinical (asymptomatic) stages of AD (see, e.g., FIG. 3 in Sperling et al., (2011) *Alzheimer's & Dementia*, 1-13). Biomarkers of brain amyloidosis include, but are not limited to reductions in CSF $A\beta_{42}$ and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (MRI) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al., (2009) *Neurology*, 73: 294-301; Yaffe et al., (2011) *JAMA* 305: 261-266).

In certain embodiments, the subjects suitable for the prophylactic methods contemplated herein include, but are not limited to subject characterized as having asymptomatic cerebral amyloidosis. In various embodiments, these individuals have biomarker evidence of Aβ accumulation with elevated tracer retention on PET amyloid imaging and/or low Aβ42 in CSF assay, but typically no detectable evidence of additional brain alterations suggestive of neurodegeneration or subtle cognitive and/or behavioral symptomatology.

It is noted that currently available CSF and PET imaging biomarkers of Aβ primarily provide evidence of amyloid accumulation and deposition of fibrillar forms of amyloid. Data suggest that soluble or oligomeric forms of Aβ are likely in equilibrium with plaques, which may serve as reservoirs. In certain embodiments, it is contemplated that there is an identifiable preplaque stage in which only soluble forms of Aβ are present. In certain embodiments, it is contemplated that oligomeric forms of amyloid may be critical in the pathological cascade, and provide useful markers. In addition, early synaptic changes may be present before evidence of amyloid accumulation.

In certain embodiments, the subjects suitable for the prophylactic methods contemplated herein include, but are not limited to, subjects characterized as amyloid positive with evidence of synaptic dysfunction and/or early neurodegeneration. In various embodiments, these subjects have evidence of amyloid positivity and presence of one or more markers of "downstream" AD-P-related neuronal injury. Illustrative, but non-limiting markers of neuronal injury include, but are not limited to (1) elevated CSF tau or phospho-tau, (2) hypometabolism in an AD-like pattern (e.g., posterior cingulate, precuneus, and/or temporoparietal cortices) on FDG-PET, and (3) cortical thinning/gray matter loss in a specific anatomic distribution (e.g., lateral and medial parietal, posterior cingulate, and lateral temporal cortices) and/or hippocampal atrophy on volumetric MRI. Other markers include, but are not limited to fMRI measures of default network connectivity. In certain embodiments, early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (e.g., in later stages of preclinical (asymptomatic) AD).

In certain embodiments, the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD, and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments, criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein present methods are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see, e.g., Hardy (1997) *Trends. Neurosci.*, 20: 154-159). Other markers of risk include mutations in the presenilin genes (PS1 and PS2), family history of AD, having the familial Alzheimer's disease (FAD) mutation, the APOE ∊4 allele, hypercholesterolemia or atherosclerosis. Further susceptibility genes for the development of Alzheimer's disease are reviewed, e.g., in Sleegers et al. (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., 20, 30, 40, 50 years of age).

Usually, however, it is not necessary to begin treatment until a patient reaches at least about 40, 50, 60 or 70 years of age.

In some embodiments, the subject is exhibiting symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al. (2010) *Int. J. Alzheimer's Dis.* 2010:606802).

In certain embodiments, subjects amenable to treatment may have age-associated memory impairment (AAMI), or mild cognitive impairment (MCI). The methods described herein are particularly well-suited to the prophylaxis and/or treatment of MCI. In such instances, the methods can delay or prevent the onset of MCI, and or reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

In various embodiments, the peptides described herein are contemplated in the treatment and/or prophylaxis of age-related cognitive decline and/or in the treatment and/or prophylaxis of mild cognitive impairment (MCI). Mild cognitive impairment, also known as incipient dementia, or isolated memory impairment) is a diagnosis given to individuals who have cognitive impairments beyond that expected for their age and education, but that typically do not interfere significantly with their daily activities (see, e.g., Petersen et al., (1999) *Arch. Neurol.* 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al., (2004) *Arch. Neurol.* 61(1): 59-66; and on the internet at en.wikipedia.org/wiki/Mild_cognitive_impairment-cite_note-Grundman-1). When individuals have impairments in domains other than memory it is often classified as non-amnestic single- or multiple-domain MCI and these individuals are believed to be more likely to convert to other dementias (e.g. dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al., (2006) *Arch. Neurol.*, 63(5): 665-72).

The diagnosis of MCI typically involves a comprehensive clinical assessment including clinical observation, neuroimaging, blood tests and neuropsychological testing. In certain embodiments, diagnostic criteria for MCI include, but are not limited to those described by Albert et al., (2011) *Alzheimer's & Dementia.* 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments, clinical evaluation/diagnosis of MCI involves: (1) Concern reflecting a change in cognition reported by patient or informant or clinician (e.g., historical or observed evidence of decline over time); (2) Objective evidence of Impairment in one or more cognitive domains, typically including memory (e.g., formal or bedside testing to establish level of cognitive function in multiple domains); (3) Preservation of independence in functional abilities; (4) Not demented; and in certain embodiments, (5) An etiology of MCI consistent with AD pathophysiological processes. Typically vascular, traumatic, medical causes of cognitive decline are ruled out where possible. In certain embodiments, evidence of longitudinal decline in cognition is identified, when feasible. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (e.g., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (e.g., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include, but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), figure copying (spatial skills), and digit span forward (attention).

As indicated above, genetic factors can be incorporated into the diagnosis of MCI. If an autosomal dominant form of AD is known to be present (e.g., mutation in APP, PS1, PS2), then the development of MCI is most likely the precursor to AD dementia. The large majority of these cases develop early onset AD (e.g., onset below 65 years of age).

In addition, there are genetic influences on the development of late onset AD dementia. For example, the presence of one or two ϵ4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE ϵ4 positive, is more likely to progress to AD dementia within a few years than an individual without this genetic characteristic. It is believed that additional genes play an important, but smaller role than APOE and also confer changes in risk for progression to AD dementia (see, e.g., Bertram et al., (2010) *Neuron*, 21: 270-281).

In certain embodiments, subjects suitable for the prophylactic methods described herein (e.g., administration of the netrin loop peptides described herein) include, but need not be limited to subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "Aβ" (which includes CSF Aβ$_{42}$ and/or PET amyloid imaging) and "biomarkers of neuronal injury" (which include, but are not limited to CSF tau/p-tau, hippocampal, or medial temporal lobe atrophy on MRI, and temporoparietal/precuneus hypometabolism or hypoperfusion on PET or SPECT).

Without being bound to a particular theory, it is believed that evidence of both Aβ, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Ab accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein.

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be is well suited for the methods described herein.

Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al., (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al., (2008) *Brain* 131 (Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments, MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 3.

TABLE 3

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home | |
| | | | | Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores | Only simple chores preserved; very restricted interests, poorly maintained | No significant function in home |

TABLE 3-continued

Illustrative clinical dementia rating (CDR) table.

| | Impairment: | | | |
|---|---|---|---|---|
| None | Questionable | Mild | Moderate | Severe |
| | | CDR: | | |
| 0 | 0.5 | 1 | 2 | 3 |
| Personal Care | Fully capable of self-care | abandoned; more complicated hobbies and interests abandoned Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments, administration of one or more peptides described herein is deemed effective when there is a reduction in the CSF of levels of one or more components selected from the group consisting of Tau, phospho-Tau (pTau), APPneo, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al., (2004) *Arch. Neurol.*, 61: 59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemory cognitive measures included in the battery. Tests of learning, attention, perceptual speed, category fluency, and executive function may be impaired in patients with MCI, but these are far less prominent than the memory deficit.

Alzheimer's Disease (AD).

In certain embodiments, the active agent(s) (e.g., netrin loop peptides described herein) and/or formulations thereof are contemplated for the treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments, subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al., (1984) *Neurology* 34(7): 939-944. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al., (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al., (1984) *Am. J. Psychiatr.*, 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al., supra). Any score greater than or equal to 25 points (out of 30) is effectively normal (intact). Below this, scores can indicate severe (≤9 points), moderate (10-20 points) or mild (21-24 points) Alzheimer's disease.

Alzheimer's disease can be broken down into various stages including: 1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 4.

TABLE 4

Illustrative stages of Alzheimer's disease.

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.
Decreased capacity to perform complex tasks, such as marketing, planning dinner for guests, or paying bills and managing finances.
Reduced memory of personal history.
The affected individual may seem subdued and withdrawn, especially in socially or mentally challenging situations.
Moderately severe cognitive decline
(Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.
Severe cognitive decline (Moderately
severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).
Have increasing episodes of urinary or fecal incontinence.
Experience significant personality changes and behavioral symptoms, including suspiciousness and delusions (for example, believing that their caregiver is an impostor); hallucinations (seeing or hearing things that are not really there); or compulsive, repetitive behaviors TABLE 4-continued Illustrative stages of Alzheimer's disease.

such as hand-wringing or tissue shredding.
Tend to wander and become lost.
Very severe cognitive decline (Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up. Reflexes become abnormal and muscles grow rigid.
Swallowing is impaired.

In various embodiments, administration of one or more agents described herein to subjects diagnosed with Alzheimer's disease is deemed effective when the there is a reduction in the CSF of levels of one or more components selected from the group consisting of Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 4 is slowed or stopped).

In certain embodiments, subjects amenable to the present methods generally are free of a neurological disease or disorder other than Alzheimer's disease. For example, in certain embodiments, the subject does not have and is not at risk of developing a neurological disease or disorder such as Huntington's Disease, and/or Parkinson's disease, and/or schizophrenia, and/or psychosis.

In various embodiments, the effectiveness of treatment can be determined by comparing a baseline measure of a parameter of disease before administration of the active agent(s) (e.g., netrin loop peptides described herein) is commenced to the same parameter one or more time points after the formulation has been administered. One illustrative parameter that can be measured is a biomarker (e.g., a peptide oligomer) of APP processing. Such biomarkers include, but are not limited to increased levels of sAPPα, p3 (Aβ 17-42 or Aβ 17-40), βAPPβ, soluble Aβ40, and/or soluble Aβ42 in the blood, plasma, serum, urine, mucous or cerebrospinal fluid (CSF). Detection of increased levels of sAPPα and/or p3, and decreased levels of βAPPβ and/or APPneo is an indicator that the treatment is effective. Conversely, detection of decreased levels of sAPPα and/or p3, and/or increased levels of βAPPβ, APPneo, Tau or phospho-Tau (pTau) is an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MRI.

In various embodiments, administration of the active agent(s) described herein can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating (CDR), the mini-mental state examination (MMSE) or Folstein test, evaluative criteria listed in the DSM-IV (Diagnostic and Statistical Manual of Mental Disorders, Fourth Edition) or DSM-V, and the like.

In certain embodiments, the monitoring methods can entail determining a baseline value of a measurable biomarker or parameter (e.g., amyloid plaque load or cognitive abilities) in a subject before administering a dosage of the multi-component formulation and optionally one or more pharmaceuticals, and comparing this biomarker or parameter with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

In various embodiments, the tissue sample for analysis is typically blood, plasma, serum, urine, mucous or cerebrospinal fluid from the subject.

Therapeutic/Prophylactic Loop Peptides.

We have used a computational program called COOT to generate a Rosetta model of the human Netrin-1. We then identified loops on the N-terminal, C-terminal and laminin domain of netrin-1 to identify interaction loops (see Example 1). These cyclic peptides have the ability to affect APP signaling based on their effect on sAPPα and intracellular ERK phosphorylation and also are able to switch APP processing from aberrant to normal.

Two peptides shown to modulate ERK phosphorylation and/or to switch APP processing from aberrant to normal are C-I-D-P-C(SEQ ID NO:1) and C-P-H-F-C (SEQ ID NO:2). Cyclized versions of these "loop peptides" were prepared and tested and are shown below as Formula I (peptide 1) (SEQ ID NO:1) and Formula II (peptide 2) (SEQ ID NO:2):

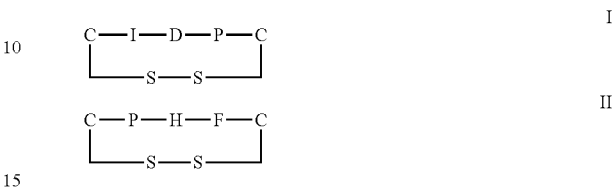

A third peptide also believed to be effective is shown below as Formula III (peptide 3) (SEQ ID NO:3):

It is noted that peptide is derived from the N-terminal domain of Netrin, peptide 2 is derived from the middle (EGF) domain and peptide 3 derived from a region near the C-terminal domain.

While the cyclized peptides shown in Formulas I. II, and III are illustrated as 5 amino acid peptides (5 mer peptides) it is recognized that these and related structures described herein can be presented as one or more domains in a larger peptide and still maintain efficacy. In certain embodiments the larger peptide is a peptide ranging in length from about 5 amino acids up to about 600 amino acids, or from about 5 amino acids up to about 400 amino acids, or up to about 300 amino acids, or up to about 200 amino acids, or up to about 150 amino acids, or up to about 100 amino acids, or up to about 75 amino acids, or up to about 50 amino acids, or up to about 30 amino acids, or up to about 25 amino acids, or up to or about 20 amino acids, or up to about 10 amino acids, or up to about 9 amino acids. In various embodiments the peptides expressly exclude non-loop domains that correspond in amino acid sequence to regions of a netrin-1 peptide.

In certain embodiments the peptide comprises an amino acid sequence of the formula:

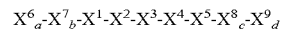

where $X^1$, $X^2$, $X^3$, $X^4$, $X^5$, $X^6$, $X^7$, $X^8$, and $X^9$ are independently selected amino acids and a, b, c, and d are independently 0 or 1, and the peptide binds APP or a fragment thereof, and/or, when administered to a cell, alters APP signaling and/or switches APP processing from aberrant to normal. In certain embodiments $X^1$, $X^2$, $X^3$, $X^4$, $X^5$, $X^6$, $X^7$, $X^8$, and $X^9$ are independently selected from the amino acids listed in Table 1. In certain embodiments $X^1$, $X^2$, $X^3$, $X^4$, $X^5$, $X^6$, $X^7$, $X^8$, and $X^9$ are independently selected naturally-occurring amino acids. In certain embodiments any one of $X^6$, $X^7$, or $X^1$ are attached to $X^5$, $X^8$, or $X^9$ to form a cyclic peptide.

In certain embodiments the peptide is a pentapeptide comprising the formula:

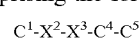

where $C^1$ and/or $C^5$ are independently selected amino acids capable of forming a cyclic linkage through their side chain, embodiments $X^2$, $X^3$, and $X^4$ are independently selected amino acids, and the peptide, when administered to a cell, alters APP signaling and/or switches APP processing from aberrant to normal. In certain embodiments $C^1$ and $C^5$ are independently selected cysteines or cysteine analogues, wherein said cysteines or cysteine analogs are attached to each other by a linkage that does not comprise $X^2$, $X^3$, and $X^4$.

In certain embodiments $X^2$ is selected from the group consisting of I or conservative substitutions thereof, P or conservative substitutions thereof, and V or conservative substitutions thereof. In certain embodiments $X^2$ is selected from the group consisting of I, P, and V.

In certain embodiments $X^3$ is selected from the group consisting of D or conservative substitutions thereof, H or conservative substitutions thereof, and A or conservative substitutions thereof. In certain embodiments $X^2$ is selected from the group consisting of D, H, and A.

In certain embodiments $X^4$ is selected from the group consisting of P or conservative substitutions thereof, F or conservative substitutions thereof, and H or conservative substitutions thereof. In certain embodiments $X^2$ is selected from the group consisting of P, F, and H.

In certain embodiments $X^2$-$X^3$-$X^4$ is given by the formula (I/P/V)-(D/H/A)-(P/F/G). In certain embodiments $X^2$-$X^3$-$X^4$ is I-D-P, or P-H-F, or V-A-G.

In certain embodiments $X^2$, $X^3$, and $X^4$ are independently selected from the amino acids listed in Table 1. In certain embodiments $X^2$, $X^3$, and $X^4$ are independently selected naturally occurring amino acids.

In various embodiments amino acids. In certain embodiments $X^2$-$X^3$ and/or $X^3$-$X^4$ is an amino acid pair listed in Table 5. In certain embodiments $X^2$-$X^3$ is an amino acid pair listed in Table 5 and $X^4$ is an amino acid listed in Table 1 and/or is a naturally occurring amino acid. In certain embodiments $X^3$-$X^4$ is an amino acid pair listed in Table 5 and $X^2$ is an amino acid listed in Table 1 and/or is a naturally occurring amino acid.

In certain embodiments $X^2$-$X^3$ is an amino acid pair listed in Table 5 comprising only naturally-occurring amino acids and $X^4$ is an amino acid listed in Table 1 and/or is a naturally occurring amino acid. In certain embodiments $X^2$-$X^3$ is an amino acid pair listed in Table 5 comprising only naturally-occurring amino acids and $X^4$ is P, F, or G, or conservative substitutions thereof. In certain embodiments $X^3$-$X^4$ is an amino acid pair listed in Table 5 comprising only naturally-occurring amino acids and $X^2$ is an amino acid listed in Table 1 and/or is a naturally occurring amino acid. In certain embodiments $X^3$-$X^4$ is an amino acid pair listed in Table 5 comprising only naturally-occurring amino acids and $X^2$ is I, or P, or V or conservative substitutions thereof. In various embodiments $X^2$ is I or P. In various embodiments $X^3$ is D or H. In various embodiments $X^4$ is P or F. In various embodiments $X^2$ is I. In various embodiments $X^3$ is D. In various embodiments $X^4$ is P.

In certain embodiments $X^2$-$X^3$-$X^4$ is -I-P-D- or -P-F-H-, or V-A-G. In certain embodiments the cyclizing linkage comprises a disulfide bond, or a polyethylene glycol (PEG). In various embodiments the peptide excludes an Arg-Gly-Asp motif.

TABLE 5

Illustrative combinations for $X^2$ - $X^3$ and/or $X^3$ - $X^4$.

| I-P | P-D | P-F | F-H | V-A | A-G |
|---|---|---|---|---|---|
| D-TIC - D-TIC | D-TIC - GABA | D-TIC - EACA | D-TIC - K[TFA] | D-TIC - 1-Nal | D-TIC - 2-Nal |
| GABA - D-TIC | GABA - GABA | GABA - EACA | GABA - K[TFA] | GABA - 1-Nal | GABA - 2-Nal |
| EACA - D-TIC | EACA - GABA | EACA - EACA | EACA - K[TFA] | EACA - 1-Nal | EACA - 2-Nal |
| K[TFA] - D-TIC | K[TFA] - GABA | K[TFA] - EACA | K[TFA] - K[TFA] | K[TFA] - 1-Nal | K[TFA] - 2-Nal |
| 1-Nal - D-TIC | 1-Nal - GABA | 1-Nal - EACA | 1-Nal - K[TFA] | 1-Nal - 1-Nal | 1-Nal - 2-Nal |
| 2-Nal - D-TIC | 2-Nal - GABA | 2-Nal - EACA | 2-Nal - K[TFA] | 2-Nal - 1-Nal | 2-Nal - 2-Nal |
| 3Hyp - D-TIC | 3Hyp - GABA | 3Hyp - EACA | 3Hyp - K[TFA] | 3Hyp - 1-Nal | 3Hyp - 2-Nal |
| 3-Pal - D-TIC | 3-Pal - GABA | 3-Pal - EACA | 3-Pal - K[TFA] | 3-Pal - 1-Nal | 3-Pal - 2-Nal |
| 4Abu - D-TIC | 4Abu - GABA | 4Abu - EACA | 4Abu - K[TFA] | 4 Abu - 1-Nal | 4Abu - 2-Nal |
| 4Hyp - D-TIC | 4Hyp - GABA | 4Hyp - EACA | 4Hyp - K[TFA] | 4Hyp - 1-Nal | 4Hyp - 2-Nal |
| A2bu - D-TIC | A2bu - GABA | A2bu - EACA | A2bu - K[TFA] | A2bu - 1-Nal | A2bu - 2-Nal |
| A2pr - D-TIC | A2pr - GABA | A2pr - EACA | A2pr - K[TFA] | A2pr - 1-Nal | A2pr - 2-Nal |
| Aad - D-TIC | Aad - GABA | Aad - EACA | Aad - K[TFA] | Aad - 1-Nal | Aad - 2-Nal |
| aAhx - D-TIC | aAhx - GABA | aAhx - EACA | aAhx - K[TFA] | aAhx - 1-Nal | aAhx - 2-Nal |
| Abo - D-TIC | Abo - GABA | Abo - EACA | Abo - K[TFA] | Abo - 1-Nal | Abo - 2-Nal |
| Abu - D-TIC | Abu - GABA | Abu - EACA | Abu - K[TFA] | Abu - 1-Nal | Abu - 2-Nal |
| ACCA - D-TIC | ACCA - GABA | ACCA - EACA | ACCA - K[TFA] | ACCA - 1-Nal | ACCA - 2-Nal |
| Acp - D-TIC | Acp - GABA | Acp - EACA | Acp - K[TFA] | Acp - 1-Nal | Acp - 2-Nal |
| Ahe - D-TIC | Ahe - GABA | Ahe - EACA | Ahe - K[TFA] | Ahe - 1-Nal | Ahe - 2-Nal |
| Ahx - D-TIC | Ahx - GABA | Ahx - EACA | Ahx - K[TFA] | Ahx - 1-Nal | Ahx - 2-Nal |
| aHyl - D-TIC | aHyl - GABA | aHyl - EACA | aHyl - K[TFA] | aHyl - 1-Nal | aHyl - 2-Nal |
| Aib - D-TIC | Aib - GABA | Aib - EACA | Aib - K[TFA] | Aib - 1-Nal | Aib - 2-Nal |
| Aib - D-TIC | Aib - GABA | Aib - EACA | Aib - K[TFA] | Aib - 1-Nal | Aib - 2-Nal |
| Aic - D-TIC | Aic - GABA | Aic - EACA | Aic - K[TFA] | Aic - 1-Nal | Aic - 2-Nal |
| aIle - D-TIC | aIle - GABA | aIle - EACA | aIle - K[TFA] | aIle - 1-Nal | aIle - 2-Nal |
| Ala - D-TIC | Ala - GABA | Ala - EACA | Ala - K[TFA] | Ala - 1-Nal | Ala - 2-Nal |
| Apm - D-TIC | Apm - GABA | Apm - EACA | Apm - K[TFA] | Apm - 1-Nal | Apm - 2-Nal |
| Arg - D-TIC | Arg - GABA | Arg - EACA | Arg - K[TFA] | Arg - 1-Nal | Arg - 2-Nal |
| Asn - D-TIC | Asn - GABA | Asn - EACA | Asn - K[TFA] | Asn - 1-Nal | Asn - 2-Nal |
| Asp - D-TIC | Asp - GABA | Asp - EACA | Asp - K[TFA] | Asp - 1-Nal | Asp - 2-Nal |
| Atc - D-TIC | Atc - GABA | Atc - EACA | Atc - K[TFA] | Atc - 1-Nal | Atc - 2-Nal |
| Ava - D-TIC | Ava - GABA | Ava - EACA | Ava - K[TFA] | Ava - 1-Nal | Ava - 2-Nal |
| Aze - D-TIC | Aze - GABA | Aze - EACA | Aze - K[TFA] | Aze - 1-Nal | Aze - 2-Nal |
| bAad - D-TIC | bAad - GABA | bAad - EACA | bAad - K[TFA] | bAad - 1-Nal | bAad - 2-Nal |
| bAib - D-TIC | bAib - GABA | bAib - EACA | bAib - K[TFA] | bAib - 1-Nal | bAib - 2-Nal |
| bAla - D-TIC | bAla - GABA | bAla - EACA | bAla - K[TFA] | bAla - 1-Nal | bAla - 2-Nal |
| Cha - D-TIC | Cha - GABA | Cha - EACA | Cha - K[TFA] | Cha - 1-Nal | Cha - 2-Nal |
| Cpg - D-TIC | Cpg - GABA | Cpg - EACA | Cpg - K[TFA] | Cpg - 1-Nal | Cpg - 2-Nal |

TABLE 5-continued

Illustrative combinations for $X^2 - X^3$ and/or $X^3 - X^4$.

| I-P | P-D | P-F | F-H | V-A | A-G |
|---|---|---|---|---|---|
| Cpp - D-TIC | Cpp - GABA | Cpp - EACA | Cpp - K[TFA] | Cpp - 1-Nal | Cpp - 2-Nal |
| cPzACAla - D-TIC | cPzACAla - GABA | cPzACAla - EACA | cPzACAla - K[TFA] | cPzACAla - 1-Nal | cPzACAla - 2-Nal |
| Cys - D-TIC | Cys - GABA | Cys - EACA | Cys - K[TFA] | Cys - 1-Nal | Cys - 2-Nal |
| Dap - D-TIC | Dap - GABA | Dap - EACA | Dap - K[TFA] | Dap - 1-Nal | Dap - 2-Nal |
| Dbf - D-TIC | Dbf - GABA | Dbf - EACA | Dbf - K[TFA] | Dbf - 1-Nal | Dbf - 2-Nal |
| Dbu - D-TIC | Dbu - GABA | Dbu - EACA | Dbu - K[TFA] | Dbu - 1-Nal | Dbu - 2-Nal |
| Des - D-TIC | Des - GABA | Des - EACA | Des - K[TFA] | Des - 1-Nal | Des - 2-Nal |
| Dip - D-TIC | Dip - GABA | Dip - EACA | Dip - K[TFA] | Dip - 1-Nal | Dip - 2-Nal |
| Dph - D-TIC | Dph - GABA | Dph - EACA | Dph - K[TFA] | Dph - 1-Nal | Dph - 2-Nal |
| Dpm - D-TIC | Dpm - GABA | Dpm - EACA | Dpm - K[TFA] | Dpm - 1-Nal | Dpm - 2-Nal |
| Dpr - D-TIC | Dpr - GABA | Dpr - EACA | Dpr - K[TFA] | Dpr - 1-Nal | Dpr - 2-Nal |
| EtAsn - D-TIC | EtAsn - GABA | EtAsn - EACA | EtAsn - K[TFA] | EtAsn - 1-Nal | EtAsn - 2-Nal |
| EtGly - D-TIC | EtGly - GABA | EtGly - EACA | EtGly - K[TFA] | EtGly - 1-Nal | EtGly - 2-Nal |
| gAbu - D-TIC | gAbu - GABA | gAbu - EACA | gAbu - K[TFA] | gAbu - 1-Nal | gAbu - 2-Nal |
| Gln - D-TIC | Gln - GABA | Gln - EACA | Gln - K[TFA] | Gln - 1-Nal | Gln - 2-Nal |
| Glu - D-TIC | Glu - GABA | Glu - EACA | Glu - K[TFA] | Glu - 1-Nal | Glu - 2-Nal |
| Gly - D-TIC | Gly - GABA | Gly - EACA | Gly - K[TFA] | Gly - 1-Nal | Gly - 2-Nal |
| Gly(Ph) - D-TIC | Gly(Ph) - GABA | Gly(Ph) - EACA | Gly(Ph) - K[TFA] | Gly(Ph) - 1-Nal | Gly(Ph) - 2-Nal |
| Har - D-TIC | Har - GABA | Har - EACA | Har - K[TFA] | Har - 1-Nal | Har - 2-Nal |
| Hcy - D-TIC | Hcy - GABA | Hcy - EACA | Hcy - K[TFA] | Hcy - 1-Nal | Hcy - 2-Nal |
| Hib - D-TIC | Hib - GABA | Hib - EACA | Hib - K[TFA] | Hib - 1-Nal | Hib - 2-Nal |
| His - D-TIC | His - GABA | His - EACA | His - K[TFA] | His - 1-Nal | His - 2-Nal |
| Hse - D-TIC | Hse - GABA | Hse - EACA | Hse - K[TFA] | Hse - 1-Nal | Hse - 2-Nal |
| Hyl - D-TIC | Hyl - GABA | Hyl - EACA | Hyl - K[TFA] | Hyl - 1-Nal | Hyl - 2-Nal |
| Hyp - D-TIC | Hyp - GABA | Hyp - EACA | Hyp - K[TFA] | Hyp - 1-Nal | Hyp - 2-Nal |
| Ide - D-TIC | Ide - GABA | Ide - EACA | Ide - K[TFA] | Ide - 1-Nal | Ide - 2-Nal |
| Ile - D-TIC | Ile - GABA | Ile - EACA | Ile - K[TFA] | Ile - 1-Nal | Ile - 2-Nal |
| Iva - D-TIC | Iva - GABA | Iva - EACA | Iva - K[TFA] | Iva - 1-Nal | Iva - 2-Nal |
| Leu - D-TIC | Leu - GABA | Leu - EACA | Leu - K[TFA] | Leu - 1-Nal | Leu - 2-Nal |
| Lys - D-TIC | Lys - GABA | Lys - EACA | Lys - K[TFA] | Lys - 1-Nal | Lys - 2-Nal |
| MeGly - D-TIC | MeGly - GABA | MeGly - EACA | MeGly - K[TFA] | MeGly - 1-Nal | MeGly - 2-Nal |
| MeIle - D-TIC | MeIle - GABA | MeIle - EACA | MeIle - K[TFA] | MeIle - 1-Nal | MeIle - 2-Nal |
| MeLys - D-TIC | MeLys - GABA | MeLys - EACA | MeLys - K[TFA] | MeLys - 1-Nal | MeLys - 2-Nal |
| Met - D-TIC | Met - GABA | Met - EACA | Met - K[TFA] | Met - 1-Nal | Met - 2-Nal |
| Met (O) - D-TIC | Met (O) - GABA | Met (O) - EACA | Met (O) - K[TFA] | Met(O) - 1-Nal | Met (O) - 2-Nal |
| Met (S—Me) - D-TIC | Met (S—Me) - GABA | Met (S—Me) - EACA | Met (S—Me) - K[TFA] | Met (S—Me) - 1-Nal | Met (S—Me) - 2-Nal |
| MeVal - D-TIC | MeVal - GABA | MeVal - EACA | MeVal - K[TFA] | MeVal - 1-Nal | MeVal - 2-Nal |
| Mpt - D-TIC | Mpt - GABA | Mpt - EACA | Mpt - K[TFA] | Mpt - 1-Nal | Mpt - 2-Nal |
| Nap - D-TIC | Nap - GABA | Nap - EACA | Nap - K[TFA] | Nap - 1-Nal | Nap - 2-Nal |
| Nle - D-TIC | Nle - GABA | Nle - EACA | Nle - K[TFA] | Nle - 1-Nal | Nle - 2-Nal |
| Nva - D-TIC | Nva - GABA | Nva - EACA | Nva - K[TFA] | Nva - 1-Nal | Nva - 2-Nal |
| Oic - D-TIC | Oic - GABA | Oic - EACA | Oic - K[TFA] | Oic - 1-Nal | Oic - 2-Nal |
| Opt - D-TIC | Opt - GABA | Opt - EACA | Opt - K[TFA] | Opt - 1-Nal | Opt - 2-Nal |
| Orn - D-TIC | Orn - GABA | Orn - EACA | Orn - K[TFA] | Orn - 1-Nal | Orn - 2-Nal |
| Pen - D-TIC | Pen - GABA | Pen - EACA | Pen - K[TFA] | Pen - 1-Nal | Pen - 2-Nal |
| Phe - D-TIC | Phe - GABA | Phe - EACA | Phe - K[TFA] | Phe - 1-Nal | Phe - 2-Nal |
| Phg - D-TIC | Phg - GABA | Phg - EACA | Phg - K[TFA] | Phg - 1-Nal | Phg - 2-Nal |
| Pip - D-TIC | Pip - GABA | Pip - EACA | Pip - K[TFA] | Pip - 1-Nal | Pip - 2-Nal |
| Pmp - D-TIC | Pmp - GABA | Pmp - EACA | Pmp - K[TFA] | Pmp - 1-Nal | Pmp - 2-Nal |
| Pro - D-TIC | Pro - GABA | Pro - EACA | Pro - K[TFA] | Pro - 1-Nal | Pro - 2-Nal |
| Qal - D-TIC | Qal - GABA | Qal - EACA | Qal - K[TFA] | Qal - 1-Nal | Qal - 2-Nal |
| Qua - D-TIC | Qua - GABA | Qua - EACA | Qua - K[TFA] | Qua - 1-Nal | Qua - 2-Nal |
| Sar - D-TIC | Sar - GABA | Sar - EACA | Sar - K[TFA] | Sar - 1-Nal | Sar - 2-Nal |
| Ser - D-TIC | Ser - GABA | Ser - EACA | Ser - K[TFA] | Ser - 1-Nal | Ser - 2-Nal |
| Thi - D-TIC | Thi - GABA | Thi - EACA | Thi - K[TFA] | Thi - 1-Nal | Thi - 2-Nal |
| Thr - D-TIC | Thr - GABA | Thr - EACA | Thr - K[TFA] | Thr - 1-Nal | Thr - 2-Nal |
| Tic - D-TIC | Tic - GABA | Tic - EACA | Tic - K[TFA] | Tic - 1-Nal | Tic - 2-Nal |
| Trp - D-TIC | Trp - GABA | Trp - EACA | Trp - K[TFA] | Trp - 1-Nal | Trp - 2-Nal |
| Tyr - D-TIC | Tyr - GABA | Tyr - EACA | Tyr - K[TFA] | Tyr - 1-Nal | Tyr - 2-Nal |
| Val - D-TIC | Val - GABA | Val - EACA | Val - K[TFA] | Val - 1-Nal | Val - 2-Nal |
| βAla - D-TIC | βAla - GABA | βAla - EACA | βAla - K[TFA] | βAla - 1-Nal | βAla - 2-Nal |
| D-TIC - 3Hyp | D-TIC - 3-Pal | D-TIC - 4Abu | D-TIC - 4Hyp | D-TIC - A2bu | D-TIC - A2pr |
| GABA - 3Hyp | GABA - 3-Pal | GABA - 4Abu | GABA - 4Hyp | GABA - A2bu | GABA - A2pr |
| EACA - 3Hyp | EACA - 3-Pal | EACA - 4Abu | EACA - 4Hyp | EACA - A2bu | EACA - A2pr |
| K[TFA] - 3Hyp | K[TFA] - 3-Pal | K[TFA] - 4Abu | K[TFA] - 4Hyp | K[TFA] - A2bu | K[TFA] - A2pr |
| 1-Nal - 3Hyp | 1-Nal - 3-Pal | 1-Nal - 4Abu | 1-Nal - 4Hyp | 1-Nal - A2bu | 1-Nal - A2pr |
| 2-Nal - 3Hyp | 2-Nal - 3-Pal | 2-Nal - 4Abu | 2-Nal - 4Hyp | 2-Nal - A2bu | 2-Nal - A2pr |
| 3Hyp - 3Hyp | 3Hyp - 3-Pal | 3Hyp - 4Abu | 3Hyp - 4Hyp | 3Hyp - A2bu | 3Hyp - A2pr |
| 3-Pal - 3Hyp | 3-Pal - 3-Pal | 3-Pal - 4 Abu | 3-Pal - 4Hyp | 3-Pal - A2bu | 3-Pal - A2pr |
| 4Abu - 3Hyp | 4Abu - 3-Pal | 4Abu - 4Abu | 4Abu - 4Hyp | 4Abu - A2bu | 4Abu - A2pr |
| 4Hyp - 3Hyp | 4Hyp - 3-Pal | 4Hyp - 4Abu | 4Hyp - 4Hyp | 4Hyp - A2bu | 4Hyp - A2pr |
| A2bu - 3Hyp | A2bu - 3-Pal | A2bu - 4Abu | A2bu - 4Hyp | A2bu - A2bu | A2bu - A2pr |
| A2pr - 3Hyp | A2pr - 3-Pal | A2pr - 4Abu | A2pr - 4Hyp | A2pr - A2bu | A2pr - A2pr |
| Aad - 3Hyp | Aad - 3-Pal | Aad - 4Abu | Aad - 4Hyp | Aad - A2bu | Aad - A2pr |
| aAhx - 3Hyp | aAhx - 3-Pal | aAhx - 4Abu | aAhx - 4Hyp | aAhx - A2bu | aAhx - A2pr |

TABLE 5-continued

Illustrative combinations for $X^2 - X^3$ and/or $X^3 - X^4$.

| I-P | P-D | P-F | F-H | V-A | A-G |
|---|---|---|---|---|---|
| Abo - 3Hyp | Abo - 3-Pal | Abo - 4Abu | Abo - 4Hyp | Abo - A2bu | Abo - A2pr |
| Abu - 3Hyp | Abu - 3-Pal | Abu - 4Abu | Abu - 4Hyp | Abu - A2bu | Abu - A2pr |
| ACCA - 3Hyp | ACCA - 3-Pal | ACCA - 4Abu | ACCA - 4Hyp | ACCA - A2bu | ACCA - A2pr |
| Acp - 3Hyp | Acp - 3-Pal | Acp - 4Abu | Acp - 4Hyp | Acp - A2bu | Acp - A2pr |
| Ahe - 3Hyp | Ahe - 3-Pal | Ahe - 4Abu | Ahe - 4Hyp | Ahe - A2bu | Ahe - A2pr |
| Ahx - 3Hyp | Ahx - 3-Pal | Ahx - 4Abu | Ahx - 4Hyp | Ahx - A2bu | Ahx - A2pr |
| aHyl - 3Hyp | aHyl - 3-Pal | aHyl - 4Abu | aHyl - 4Hyp | aHyl - A2bu | aHyl - A2pr |
| Aib - 3Hyp | Aib - 3-Pal | Aib - 4Abu | Aib - 4Hyp | Aib - A2bu | Aib - A2pr |
| Aib - 3Hyp | Aib - 3-Pal | Aib - 4Abu | Aib - 4Hyp | Aib - A2bu | Aib - A2pr |
| Aic - 3Hyp | Aic - 3-Pal | Aic - 4Abu | Aic - 4Hyp | Aic - A2bu | Aic - A2pr |
| aIle - 3Hyp | aIle - 3-Pal | aIle - 4Abu | aIle - 4Hyp | aIle - A2bu | aIle - A2pr |
| Ala - 3Hyp | Ala - 3-Pal | Ala - 4Abu | Ala - 4Hyp | Ala - A2bu | Ala - A2pr |
| Apm - 3Hyp | Apm - 3-Pal | Apm - 4Abu | Apm - 4Hyp | Apm - A2bu | Apm - A2pr |
| Arg - 3Hyp | Arg - 3-Pal | Arg - 4Abu | Arg - 4Hyp | Arg - A2bu | Arg - A2pr |
| Asn - 3Hyp | Asn - 3-Pal | Asn - 4Abu | Asn - 4Hyp | Asn - A2bu | Asn - A2pr |
| Asp - 3Hyp | Asp - 3-Pal | Asp - 4Abu | Asp - 4Hyp | Asp - A2bu | Asp - A2pr |
| Atc - 3Hyp | Atc - 3-Pal | Atc - 4Abu | Atc - 4Hyp | Atc - A2bu | Atc - A2pr |
| Ava - 3Hyp | Ava - 3-Pal | Ava - 4Abu | Ava - 4Hyp | Ava - A2bu | Ava - A2pr |
| Aze - 3Hyp | Aze - 3-Pal | Aze - 4Abu | Aze - 4Hyp | Aze - A2bu | Aze - A2pr |
| bAad - 3Hyp | bAad - 3-Pal | bAad - 4Abu | bAad - 4Hyp | bAad - A2bu | bAad - A2pr |
| bAib - 3Hyp | bAib - 3-Pal | bAib - 4Abu | bAib - 4Hyp | bAib - A2bu | bAib - A2pr |
| bAla - 3Hyp | bAla - 3-Pal | bAla - 4Abu | bAla - 4Hyp | bAla - A2bu | bAla - A2pr |
| Cha - 3Hyp | Cha - 3-Pal | Cha - 4Abu | Cha - 4Hyp | Cha - A2bu | Cha - A2pr |
| Cpg - 3Hyp | Cpg - 3-Pal | Cpg - 4Abu | Cpg - 4Hyp | Cpg - A2bu | Cpg - A2pr |
| Cpp - 3Hyp | Cpp - 3-Pal | Cpp - 4Abu | Cpp - 4Hyp | Cpp - A2bu | Cpp - A2pr |
| cPzACAla - 3Hyp | cPzACAla - 3-Pal | cPzACAla - 4Abu | cPzACAla - 4Hyp | cPzACAla - A2bu | cPzACAla - A2pr |
| Cys - 3Hyp | Cys - 3-Pal | Cys - 4Abu | Cys - 4Hyp | Cys - A2bu | Cys - A2pr |
| Dap - 3Hyp | Dap - 3-Pal | Dap - 4Abu | Dap - 4Hyp | Dap - A2bu | Dap - A2pr |
| Dbf - 3Hyp | Dbf - 3-Pal | Dbf - 4Abu | Dbf - 4Hyp | Dbf - A2bu | Dbf - A2pr |
| Dbu - 3Hyp | Dbu - 3-Pal | Dbu - 4Abu | Dbu - 4Hyp | Dbu - A2bu | Dbu - A2pr |
| Des - 3Hyp | Des - 3-Pal | Des - 4Abu | Des - 4Hyp | Des - A2bu | Des - A2pr |
| Dip - 3Hyp | Dip - 3-Pal | Dip - 4Abu | Dip - 4Hyp | Dip - A2bu | Dip - A2pr |
| Dph - 3Hyp | Dph - 3-Pal | Dph - 4Abu | Dph - 4Hyp | Dph - A2bu | Dph - A2pr |
| Dpm - 3Hyp | Dpm - 3-Pal | Dpm - 4Abu | Dpm - 4Hyp | Dpm - A2bu | Dpm - A2pr |
| Dpr - 3Hyp | Dpr - 3-Pal | Dpr - 4Abu | Dpr - 4Hyp | Dpr - A2bu | Dpr - A2pr |
| EtAsn - 3Hyp | EtAsn - 3-Pal | EtAsn - 4Abu | EtAsn - 4Hyp | EtAsn - A2bu | EtAsn - A2pr |
| EtGly - 3Hyp | EtGly - 3-Pal | EtGly - 4Abu | EtGly - 4Hyp | EtGly - A2bu | EtGly - A2pr |
| gAbu - 3Hyp | gAbu - 3-Pal | gAbu - 4Abu | gAbu - 4Hyp | gAbu - A2bu | gAbu - A2pr |
| Gln - 3Hyp | Gln - 3-Pal | Gln - 4Abu | Gln - 4Hyp | Gln - A2bu | Gln - A2pr |
| Glu - 3Hyp | Glu - 3-Pal | Glu - 4Abu | Glu - 4Hyp | Glu - A2bu | Glu - A2pr |
| Gly - 3Hyp | Gly - 3-Pal | Gly - 4Abu | Gly - 4Hyp | Gly - A2bu | Gly - A2pr |
| Gly(Ph) - 3Hyp | Gly(Ph) - 3-Pal | Gly(Ph) - 4Abu | Gly(Ph) - 4Hyp | Gly(Ph) - A2bu | Gly(Ph) - A2pr |
| Har - 3Hyp | Har - 3-Pal | Har - 4Abu | Har - 4Hyp | Har - A2bu | Har - A2pr |
| Hcy - 3Hyp | Hcy - 3-Pal | Hcy - 4Abu | Hcy - 4Hyp | Hcy - A2bu | Hcy - A2pr |
| Hib - 3Hyp | Hib - 3-Pal | Hib - 4Abu | Hib - 4Hyp | Hib - A2bu | Hib - A2pr |
| His - 3Hyp | His - 3-Pal | His - 4Abu | His - 4Hyp | His - A2bu | His - A2pr |
| Hse - 3Hyp | Hse - 3-Pal | Hse - 4Abu | Hse - 4Hyp | Hse - A2bu | Hse - A2pr |
| Hyl - 3Hyp | Hyl - 3-Pal | Hyl - 4Abu | Hyl - 4Hyp | Hyl - A2bu | Hyl - A2pr |
| Hyp - 3Hyp | Hyp - 3-Pal | Hyp - 4Abu | Hyp - 4Hyp | Hyp - A2bu | Hyp - A2pr |
| Ide - 3Hyp | Ide - 3-Pal | Ide - 4Abu | Ide - 4Hyp | Ide - A2bu | Ide - A2pr |
| Ile - 3Hyp | Ile - 3-Pal | Ile - 4Abu | Ile - 4Hyp | Ile - A2bu | Ile - A2pr |
| Iva - 3Hyp | Iva - 3-Pal | Iva - 4Abu | Iva - 4Hyp | Iva - A2bu | Iva - A2pr |
| Leu - 3Hyp | Leu - 3-Pal | Leu - 4Abu | Leu - 4Hyp | Leu - A2bu | Leu - A2pr |
| Lys - 3Hyp | Lys - 3-Pal | Lys - 4Abu | Lys - 4Hyp | Lys - A2bu | Lys - A2pr |
| MeGly - 3Hyp | MeGly - 3-Pal | MeGly - 4Abu | MeGly - 4Hyp | MeGly - A2bu | MeGly - A2pr |
| MeIle - 3Hyp | MeIle - 3-Pal | MeIle - 4Abu | MeIle - 4Hyp | MeIle - A2bu | MeIle - A2pr |
| MeLys - 3Hyp | MeLys - 3-Pal | MeLys - 4Abu | MeLys - 4Hyp | MeLys - A2bu | MeLys - A2pr |
| Met - 3Hyp | Met - 3-Pal | Met - 4Abu | Met - 4Hyp | Met - A2bu | Met - A2pr |
| Met (O) - 3Hyp | Met (O) - 3-Pal | Met (O) - 4Abu | Met (O) - 4Hyp | Met (O) - A2bu | Met (O) - A2pr |
| Met (S—Me) - 3Hyp | Met (S—Me) - 3-Pal | Met (S—Me) - 4Abu | Met (S—Me) - 4Hyp | Met (S—Me) - A2bu | Met (S—Me) - A2pr |
| MeVal - 3Hyp | MeVal - 3-Pal | MeVal - 4Abu | MeVal - 4Hyp | MeVal - A2bu | MeVal - A2pr |
| Mpt - 3Hyp | Mpt - 3-Pal | Mpt - 4Abu | Mpt - 4Hyp | Mpt - A2bu | Mpt - A2pr |
| Nap - 3Hyp | Nap - 3-Pal | Nap - 4Abu | Nap - 4Hyp | Nap - A2bu | Nap - A2pr |
| Nle - 3Hyp | Nle - 3-Pal | Nle - 4Abu | Nle - 4Hyp | Nle - A2bu | Nle - A2pr |
| Nva - 3Hyp | Nva - 3-Pal | Nva - 4Abu | Nva - 4Hyp | Nva - A2bu | Nva - A2pr |
| Oic - 3Hyp | Oic - 3-Pal | Oic - 4Abu | Oic - 4Hyp | Oic - A2bu | Oic - A2pr |
| Opt - 3Hyp | Opt - 3-Pal | Opt - 4Abu | Opt - 4Hyp | Opt - A2bu | Opt - A2pr |
| Orn - 3Hyp | Orn - 3-Pal | Orn - 4Abu | Orn - 4Hyp | Orn - A2bu | Orn - A2pr |
| Pen - 3Hyp | Pen - 3-Pal | Pen - 4Abu | Pen - 4Hyp | Pen - A2bu | Pen - A2pr |
| Phe - 3Hyp | Phe - 3-Pal | Phe - 4Abu | Phe - 4Hyp | Phe - A2bu | Phe - A2pr |
| Phg - 3Hyp | Phg - 3-Pal | Phg - 4Abu | Phg - 4Hyp | Phg - A2bu | Phg - A2pr |
| Pip - 3Hyp | Pip - 3-Pal | Pip - 4Abu | Pip - 4Hyp | Pip - A2bu | Pip - A2pr |
| Pmp - 3Hyp | Pmp - 3-Pal | Pmp - 4Abu | Pmp - 4Hyp | Pmp - A2bu | Pmp - A2pr |
| Pro - 3Hyp | Pro - 3-Pal | Pro - 4Abu | Pro - 4Hyp | Pro - A2bu | Pro - A2pr |
| Qal - 3Hyp | Qal - 3-Pal | Qal - 4Abu | Qal - 4Hyp | Qal - A2bu | Qal - A2pr |

TABLE 5-continued

Illustrative combinations for $X^2 - X^3$ and/or $X^3 - X^4$.

| I-P | P-D | P-F | F-H | V-A | A-G |
|---|---|---|---|---|---|
| Qua - 3Hyp | Qua - 3-Pal | Qua - 4Abu | Qua - 4Hyp | Qua - A2bu | Qua - A2pr |
| Sar - 3Hyp | Sar - 3-Pal | Sar - 4Abu | Sar - 4Hyp | Sar - A2bu | Sar - A2pr |
| Ser - 3Hyp | Ser - 3-Pal | Ser - 4Abu | Ser - 4Hyp | Ser - A2bu | Ser - A2pr |
| Thi - 3Hyp | Thi - 3-Pal | Thi - 4Abu | Thi - 4Hyp | Thi - A2bu | Thi - A2pr |
| Thr - 3Hyp | Thr - 3-Pal | Thr - 4Abu | Thr - 4Hyp | Thr - A2bu | Thr - A2pr |
| Tic - 3Hyp | Tic - 3-Pal | Tic - 4Abu | Tic - 4Hyp | Tic - A2bu | Tic - A2pr |
| Trp - 3Hyp | Trp - 3-Pal | Trp - 4Abu | Trp - 4Hyp | Trp - A2bu | Trp - A2pr |
| Tyr - 3Hyp | Tyr - 3-Pal | Tyr - 4Abu | Tyr - 4Hyp | Tyr - A2bu | Tyr - A2pr |
| Val - 3Hyp | Val - 3-Pal | Val - 4Abu | Val - 4Hyp | Val - A2bu | Val - A2pr |
| βAla - 3Hyp | βAla - 3-Pal | βAla - 4Abu | βAla - 4Hyp | βAla - A2bu | βAla - A2pr |
| D-TIC - Aad | D-TIC - aAhx | D-TIC - Abo | D-TIC - Abu | D-TIC - ACCA | D-TIC - Acp |
| GABA - Aad | GABA - aAhx | GABA - Abo | GABA - Abu | GABA - ACCA | GABA - Acp |
| EACA - Aad | EACA - aAhx | EACA - Abo | EACA - Abu | EACA - ACCA | EACA - Acp |
| K[TFA] - Aad | K[TFA] - aAhx | K[TFA] - Abo | K[TFA] - Abu | K[TFA] - ACCA | K[TFA] - Acp |
| 1-Nal - Aad | 1-Nal - aAhx | 1-Nal - Abo | 1-Nal - Abu | 1-Nal - ACCA | 1-Nal - Acp |
| 2-Nal - Aad | 2-Nal - aAhx | 2-Nal - Abo | 2-Nal - Abu | 2-Nal - ACCA | 2-Nal - Acp |
| 3Hyp - Aad | 3Hyp - aAhx | 3Hyp - Abo | 3Hyp - Abu | 3Hyp - ACCA | 3Hyp - Acp |
| 3-Pal - Aad | 3-Pal - aAhx | 3-Pal - Abo | 3-Pal - Abu | 3-Pal - ACCA | 3-Pal - Acp |
| 4Abu - Aad | 4Abu - aAhx | 4Abu - Abo | 4Abu - Abu | 4Abu - ACCA | 4Abu - Acp |
| 4Hyp - Aad | 4Hyp - aAhx | 4Hyp - Abo | 4Hyp - Abu | 4Hyp - ACCA | 4Hyp - Acp |
| A2bu - Aad | A2bu - aAhx | A2bu - Abo | A2bu - Abu | A2bu - ACCA | A2bu - Acp |
| A2pr - Aad | A2pr - aAhx | A2pr - Abo | A2pr - Abu | A2pr - ACCA | A2pr - Acp |
| Aad - Aad | Aad - aAhx | Aad - Abo | Aad - Abu | Aad - ACCA | Aad - Acp |
| aAhx - Aad | aAhx - aAhx | aAhx - Abo | aAhx - Abu | aAhx - ACCA | aAhx - Acp |
| Abo - Aad | Abo - aAhx | Abo - Abo | Abo - Abu | Abo - ACCA | Abo - Acp |
| Abu - Aad | Abu - aAhx | Abu - Abo | Abu - Abu | Abu - ACCA | Abu - Acp |
| ACCA - Aad | ACCA - aAhx | ACCA - Abo | ACCA - Abu | ACCA - ACCA | ACCA - Acp |
| Acp - Aad | Acp - aAhx | Acp - Abo | Acp - Abu | Acp - ACCA | Acp - Acp |
| Ahe - Aad | Ahe - aAhx | Ahe - Abo | Ahe - Abu | Ahe - ACCA | Ahe - Acp |
| Ahx - Aad | Ahx - aAhx | Ahx - Abo | Ahx - Abu | Ahx - ACCA | Ahx - Acp |
| aHyl - Aad | aHyl - aAhx | aHyl - Abo | aHyl - Abu | aHyl - ACCA | aHyl - Acp |
| Aib - Aad | Aib - aAhx | Aib - Abo | Aib - Abu | Aib - ACCA | Aib - Acp |
| Aib - Aad | Aib - aAhx | Aib - Abo | Aib - Abu | Aib - ACCA | Aib - Acp |
| Aic - Aad | Aic - aAhx | Aic - Abo | Aic - Abu | Aic - ACCA | Aic - Acp |
| aIle - Aad | aIle - aAhx | aIle - Abo | aIle - Abu | aIle - ACCA | aIle - Acp |
| Ala - Aad | Ala - aAhx | Ala - Abo | Ala - Abu | Ala - ACCA | Ala - Acp |
| Apm - Aad | Apm - aAhx | Apm - Abo | Apm - Abu | Apm - ACCA | Apm - Acp |
| Arg - Aad | Arg - aAhx | Arg - Abo | Arg - Abu | Arg - ACCA | Arg - Acp |
| Asn - Aad | Asn - aAhx | Asn - Abo | Asn - Abu | Asn - ACCA | Asn - Acp |
| Asp - Aad | Asp - aAhx | Asp - Abo | Asp - Abu | Asp - ACCA | Asp - Acp |
| Atc - Aad | Atc - aAhx | Atc - Abo | Atc - Abu | Atc - ACCA | Atc - Acp |
| Ava - Aad | Ava - aAhx | Ava - Abo | Ava - Abu | Ava - ACCA | Ava - Acp |
| Aze - Aad | Aze - aAhx | Aze - Abo | Aze - Abu | Aze - ACCA | Aze - Acp |
| bAad - Aad | bAad - aAhx | bAad - Abo | bAad - Abu | bAad - ACCA | bAad - Acp |
| bAib - Aad | bAib - aAhx | bAib - Abo | bAib - Abu | bAib - ACCA | bAib - Acp |
| bAla - Aad | bAla - aAhx | bAla - Abo | bAla - Abu | bAla - ACCA | bAla - Acp |
| Cha - Aad | Cha - aAhx | Cha - Abo | Cha - Abu | Cha - ACCA | Cha - Acp |
| Cpg - Aad | Cpg - aAhx | Cpg - Abo | Cpg - Abu | Cpg - ACCA | Cpg - Acp |
| Cpp - Aad | Cpp - aAhx | Cpp - Abo | Cpp - Abu | Cpp - ACCA | Cpp - Acp |
| cPzACAla - Aad | cPzACAla - aAhx | cPzACAla - Abo | cPzACAla - Abu | cPzACAla - ACCA | cPzACAla - Acp |
| Cys - Aad | Cys - aAhx | Cys - Abo | Cys - Abu | Cys - ACCA | Cys - Acp |
| Dap - Aad | Dap - aAhx | Dap - Abo | Dap - Abu | Dap - ACCA | Dap - Acp |
| Dbf - Aad | Dbf - aAhx | Dbf - Abo | Dbf - Abu | Dbf - ACCA | Dbf - Acp |
| Dbu - Aad | Dbu - aAhx | Dbu - Abo | Dbu - Abu | Dbu - ACCA | Dbu - Acp |
| Des - Aad | Des - aAhx | Des - Abo | Des - Abu | Des - ACCA | Des - Acp |
| Dip - Aad | Dip - aAhx | Dip - Abo | Dip - Abu | Dip - ACCA | Dip - Acp |
| Dph - Aad | Dph - aAhx | Dph - Abo | Dph - Abu | Dph - ACCA | Dph - Acp |
| Dpm - Aad | Dpm - aAhx | Dpm - Abo | Dpm - Abu | Dpm - ACCA | Dpm - Acp |
| Dpr - Aad | Dpr - aAhx | Dpr - Abo | Dpr - Abu | Dpr - ACCA | Dpr - Acp |
| EtAsn - Aad | EtAsn - aAhx | EtAsn - Abo | EtAsn - Abu | EtAsn - ACCA | EtAsn - Acp |
| EtGly - Aad | EtGly - aAhx | EtGly - Abo | EtGly - Abu | EtGly - ACCA | EtGly - Acp |
| gAbu - Aad | gAbu - aAhx | gAbu - Abo | gAbu - Abu | gAbu - ACCA | gAbu - Acp |
| Gln - Aad | Gln - aAhx | Gln - Abo | Gln - Abu | Gln - ACCA | Gln - Acp |
| Glu - Aad | Glu - aAhx | Glu - Abo | Glu - Abu | Glu - ACCA | Glu - Acp |
| Gly - Aad | Gly - aAhx | Gly - Abo | Gly - Abu | Gly - ACCA | Gly - Acp |
| Gly(Ph) - Aad | Gly(Ph) - aAhx | Gly(Ph) - Abo | Gly(Ph) - Abu | Gly(Ph) - ACCA | Gly(Ph) - Acp |
| Har - Aad | Har - aAhx | Har - Abo | Har - Abu | Har - ACCA | Har - Acp |
| Hcy - Aad | Hcy - aAhx | Hcy - Abo | Hcy - Abu | Hcy - ACCA | Hcy - Acp |
| Hib - Aad | Hib - aAhx | Hib - Abo | Hib - Abu | Hib - ACCA | Hib - Acp |
| His - Aad | His - aAhx | His - Abo | His - Abu | His - ACCA | His - Acp |
| Hse - Aad | Hse - aAhx | Hse - Abo | Hse - Abu | Hse - ACCA | Hse - Acp |
| Hyl - Aad | Hyl - aAhx | Hyl - Abo | Hyl - Abu | Hyl - ACCA | Hyl - Acp |
| Hyp - Aad | Hyp - aAhx | Hyp - Abo | Hyp - Abu | Hyp - ACCA | Hyp - Acp |
| Ide - Aad | Ide - aAhx | Ide - Abo | Ide - Abu | Ide - ACCA | Ide - Acp |
| Ile - Aad | Ile - aAhx | Ile - Abo | Ile - Abu | Ile - ACCA | Ile - Acp |
| Iva - Aad | Iva - aAhx | Iva - Abo | Iva - Abu | Iva - ACCA | Iva - Acp |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| Leu - Aad | Leu - aAhx | Leu - Abo | Leu - Abu | Leu - ACCA | Leu - Acp |
| Lys - Aad | Lys - aAhx | Lys - Abo | Lys - Abu | Lys - ACCA | Lys - Acp |
| MeGly - Aad | MeGly - aAhx | MeGly - Abo | MeGly - Abu | MeGly - ACCA | MeGly - Acp |
| MeIle - Aad | MeIle - aAhx | MeIle - Abo | MeIle - Abu | MeIle - ACCA | MeIle - Acp |
| MeLys - Aad | MeLys - aAhx | MeLys - Abo | MeLys - Abu | MeLys - ACCA | MeLys - Acp |
| Met - Aad | Met - aAhx | Met - Abo | Met - Abu | Met - ACCA | Met - Acp |
| Met (O) - Aad | Met (O) - aAhx | Met (O) - Abo | Met (O) - Abu | Met (O) - ACCA | Met (O) - Acp |
| Met (S—Me) - Aad | Met (S—Me) - aAhx | Met (S—Me) - Abo | Met (S—Me) - Abu | Met (S—Me) - ACCA | Met (S—Me) - Acp |
| MeVal - Aad | MeVal - aAhx | MeVal - Abo | MeVal - Abu | MeVal - ACCA | MeVal - Acp |
| Mpt - Aad | Mpt - aAhx | Mpt - Abo | Mpt - Abu | Mpt - ACCA | Mpt - Acp |
| Nap - Aad | Nap - aAhx | Nap - Abo | Nap - Abu | Nap - ACCA | Nap - Acp |
| Nle - Aad | Nle - aAhx | Nle - Abo | Nle - Abu | Nle - ACCA | Nle - Acp |
| Nva - Aad | Nva - aAhx | Nva - Abo | Nva - Abu | Nva - ACCA | Nva - Acp |
| Oic - Aad | Oic - aAhx | Oic - Abo | Oic - Abu | Oic - ACCA | Oic - Acp |
| Opt - Aad | Opt - aAhx | Opt - Abo | Opt - Abu | Opt - ACCA | Opt - Acp |
| Orn - Aad | Orn - aAhx | Orn - Abo | Orn - Abu | Orn - ACCA | Orn - Acp |
| Pen - Aad | Pen - aAhx | Pen - Abo | Pen - Abu | Pen - ACCA | Pen - Acp |
| Phe - Aad | Phe - aAhx | Phe - Abo | Phe - Abu | Phe - ACCA | Phe - Acp |
| Phg - Aad | Phg - aAhx | Phg - Abo | Phg - Abu | Phg - ACCA | Phg - Acp |
| Pip - Aad | Pip - aAhx | Pip - Abo | Pip - Abu | Pip - ACCA | Pip - Acp |
| Pmp - Aad | Pmp - aAhx | Pmp - Abo | Pmp - Abu | Pmp - ACCA | Pmp - Acp |
| Pro - Aad | Pro - aAhx | Pro - Abo | Pro - Abu | Pro - ACCA | Pro - Acp |
| Qal - Aad | Qal - aAhx | Qal - Abo | Qal - Abu | Qal - ACCA | Qal - Acp |
| Qua - Aad | Qua - aAhx | Qua - Abo | Qua - Abu | Qua - ACCA | Qua - Acp |
| Sar - Aad | Sar - aAhx | Sar - Abo | Sar - Abu | Sar - ACCA | Sar - Acp |
| Ser - Aad | Ser - aAhx | Ser - Abo | Ser - Abu | Ser - ACCA | Ser - Acp |
| Thi - Aad | Thi - aAhx | Thi - Abo | Thi - Abu | Thi - ACCA | Thi - Acp |
| Thr - Aad | Thr - aAhx | Thr - Abo | Thr - Abu | Thr - ACCA | Thr - Acp |
| Tic - Aad | Tic - aAhx | Tic - Abo | Tic - Abu | Tic - ACCA | Tic - Acp |
| Trp - Aad | Trp - aAhx | Trp - Abo | Trp - Abu | Trp - ACCA | Trp - Acp |
| Tyr - Aad | Tyr - aAhx | Tyr - Abo | Tyr - Abu | Tyr - ACCA | Tyr - Acp |
| Val - Aad | Val - aAhx | Val - Abo | Val - Abu | Val - ACCA | Val - Acp |
| βAla - Aad | βAla - aAhx | βAla - Abo | βAla - Abu | βAla - ACCA | βAla - Acp |
| D-TIC - Ahe | D-TIC - Ahx | D-TIC - aHyl | D-TIC - Aib | D-TIC - Aib | D-TIC - Aic |
| GABA - Ahe | GABA - Ahx | GABA - aHyl | GABA - Aib | GABA - Aib | GABA - Aic |
| EACA - Ahe | EACA - Ahx | EACA - aHyl | EACA - Aib | EACA - Aib | EACA - Aic |
| K[TFA] - Ahe | K[TFA] - Ahx | K[TFA] - aHyl | K[TFA] - Aib | K[TFA] - Aib | K[TFA] - Aic |
| 1-Nal - Ahe | 1-Nal - Ahx | 1-Nal - aHyl | 1-Nal - Aib | 1-Nal - Aib | 1-Nal - Aic |
| 2-Nal - Ahe | 2-Nal - Ahx | 2-Nal - aHyl | 2-Nal - Aib | 2-Nal - Aib | 2-Nal - Aic |
| 3Hyp - Ahe | 3Hyp - Ahx | 3Hyp - aHyl | 3Hyp - Aib | 3Hyp - Aib | 3Hyp - Aic |
| 3-Pal - Ahe | 3-Pal - Ahx | 3-Pal - aHyl | 3-Pal - Aib | 3-Pal - Aib | 3-Pal - Aic |
| 4Abu - Ahe | 4Abu - Ahx | 4Abu - aHyl | 4Abu - Aib | 4Abu - Aib | 4Abu - Aic |
| 4Hyp - Ahe | 4Hyp - Ahx | 4Hyp - aHyl | 4Hyp - Aib | 4Hyp - Aib | 4Hyp - Aic |
| A2bu - Ahe | A2bu - Ahx | A2bu - aHyl | A2bu - Aib | A2bu - Aib | A2bu - Aic |
| A2pr - Ahe | A2pr - Ahx | A2pr - aHyl | A2pr - Aib | A2pr - Aib | A2pr - Aic |
| Aad - Ahe | Aad - Ahx | Aad - aHyl | Aad - Aib | Aad - Aib | Aad - Aic |
| aAhx - Ahe | aAhx - Ahx | aAhx - aHyl | aAhx - Aib | aAhx - Aib | aAhx - Aic |
| Abo - Ahe | Abo - Ahx | Abo - aHyl | Abo - Aib | Abo - Aib | Abo - Aic |
| Abu - Ahe | Abu - Ahx | Abu - aHyl | Abu - Aib | Abu - Aib | Abu - Aic |
| ACCA - Ahe | ACCA - Ahx | ACCA - aHyl | ACCA - Aib | ACCA - Aib | ACCA - Aic |
| Acp - Ahe | Acp - Ahx | Acp - aHyl | Acp - Aib | Acp - Aib | Acp - Aic |
| Ahe - Ahe | Ahe - Ahx | Ahe - aHyl | Ahe - Aib | Ahe - Aib | Ahe - Aic |
| Ahx - Ahe | Ahx - Ahx | Ahx - aHyl | Ahx - Aib | Ahx - Aib | Ahx - Aic |
| aHyl - Ahe | aHyl - Ahx | aHyl - aHyl | aHyl - Aib | aHyl - Aib | aHyl - Aic |
| Aib - Ahe | Aib - Ahx | Aib - aHyl | Aib - Aib | Aib - Aib | Aib - Aic |
| Aib - Ahe | Aib - Ahx | Aib - aHyl | Aib - Aib | Aib - Aib | Aib - Aic |
| Aic - Ahe | Aic - Ahx | Aic - aHyl | Aic - Aib | Aic - Aib | Aic - Aic |
| aIle - Ahe | aIle - Ahx | aIle - aHyl | aIle - Aib | aIle - Aib | aIle - Aic |
| Ala - Ahe | Ala - Ahx | Ala - aHyl | Ala - Aib | Ala - Aib | Ala - Aic |
| Apm - Ahe | Apm - Ahx | Apm - aHyl | Apm - Aib | Apm - Aib | Apm - Aic |
| Arg - Ahe | Arg - Ahx | Arg - aHyl | Arg - Aib | Arg - Aib | Arg - Aic |
| Asn - Ahe | Asn - Ahx | Asn - aHyl | Asn - Aib | Asn - Aib | Asn - Aic |
| Asp - Ahe | Asp - Ahx | Asp - aHyl | Asp - Aib | Asp - Aib | Asp - Aic |
| Atc - Ahe | Atc - Ahx | Atc - aHyl | Atc - Aib | Atc - Aib | Atc - Aic |
| Ava - Ahe | Ava - Ahx | Ava - aHyl | Ava - Aib | Ava - Aib | Ava - Aic |
| Aze - Ahe | Aze - Ahx | Aze - aHyl | Aze - Aib | Aze - Aib | Aze - Aic |
| bAad - Ahe | bAad - Ahx | bAad - aHyl | bAad - Aib | bAad - Aib | bAad - Aic |
| bAib - Ahe | bAib - Ahx | bAib - aHyl | bAib - Aib | bAib - Aib | bAib - Aic |
| bAla - Ahe | bAla - Ahx | bAla - aHyl | bAla - Aib | bAla - Aib | bAla - Aic |
| Cha - Ahe | Cha - Ahx | Cha - aHyl | Cha - Aib | Cha - Aib | Cha - Aic |
| Cpg - Ahe | Cpg - Ahx | Cpg - aHyl | Cpg - Aib | Cpg - Aib | Cpg - Aic |
| Cpp - Ahe | Cpp - Ahx | Cpp - aHyl | Cpp - Aib | Cpp - Aib | Cpp - Aic |
| cPzACAla - Ahe | cPzACAla - Ahx | cPzACAla - aHyl | cPzACAla - Aib | cPzACAla - Aib | cPzACAla - Aic |
| Cys - Ahe | Cys - Ahx | Cys - aHyl | Cys - Aib | Cys - Aib | Cys - Aic |
| Dap - Ahe | Dap - Ahx | Dap - aHyl | Dap - Aib | Dap - Aib | Dap - Aic |

TABLE 5-continued

Illustrative combinations for $X^2 - X^3$ and/or $X^3 - X^4$.

| I-P | P-D | P-F | F-H | V-A | A-G |
|---|---|---|---|---|---|
| Dbf - Ahe | Dbf - Ahx | Dbf - aHyl | Dbf - Aib | Dbf - Aib | Dbf - Aic |
| Dbu - Ahe | Dbu - Ahx | Dbu - aHyl | Dbu - Aib | Dbu - Aib | Dbu - Aic |
| Des - Ahe | Des - Ahx | Des - aHyl | Des - Aib | Des - Aib | Des - Aic |
| Dip - Ahe | Dip - Ahx | Dip - aHyl | Dip - Aib | Dip - Aib | Dip - Aic |
| Dph - Ahe | Dph - Ahx | Dph - aHyl | Dph - Aib | Dph - Aib | Dph - Aic |
| Dpm - Ahe | Dpm - Ahx | Dpm - aHyl | Dpm - Aib | Dpm - Aib | Dpm - Aic |
| Dpr - Ahe | Dpr - Ahx | Dpr - aHyl | Dpr - Aib | Dpr - Aib | Dpr - Aic |
| EtAsn - Ahe | EtAsn - Ahx | EtAsn - aHyl | EtAsn - Aib | EtAsn - Aib | EtAsn - Aic |
| EtGly - Ahe | EtGly - Ahx | EtGly - aHyl | EtGly - Aib | EtGly - Aib | EtGly - Aic |
| gAbu - Ahe | gAbu - Ahx | gAbu - aHyl | gAbu - Aib | gAbu - Aib | gAbu - Aic |
| Gln - Ahe | Gln - Ahx | Gln - aHyl | Gln - Aib | Gln - Aib | Gln - Aic |
| Glu - Ahe | Glu - Ahx | Glu - aHyl | Glu - Aib | Glu - Aib | Glu - Aic |
| Gly - Ahe | Gly - Ahx | Gly - aHyl | Gly - Aib | Gly - Aib | Gly - Aic |
| Gly(Ph) - Ahe | Gly(Ph) - Ahx | Gly(Ph) - aHyl | Gly(Ph) - Aib | Gly(Ph) - Aib | Gly(Ph) - Aic |
| Har - Ahe | Har - Ahx | Har - aHyl | Har - Aib | Har - Aib | Har - Aic |
| Hcy - Ahe | Hcy - Ahx | Hcy - aHyl | Hcy - Aib | Hcy - Aib | Hcy - Aic |
| Hib - Ahe | Hib - Ahx | Hib - aHyl | Hib - Aib | Hib - Aib | Hib - Aic |
| His - Ahe | His - Ahx | His - aHyl | His - Aib | His - Aib | His - Aic |
| Hse - Ahe | Hse - Ahx | Hse - aHyl | Hse - Aib | Hse - Aib | Hse - Aic |
| Hyl - Ahe | Hyl - Ahx | Hyl - aHyl | Hyl - Aib | Hyl - Aib | Hyl - Aic |
| Hyp - Ahe | Hyp - Ahx | Hyp - aHyl | Hyp - Aib | Hyp - Aib | Hyp - Aic |
| Ide - Ahe | Ide - Ahx | Ide - aHyl | Ide - Aib | Ide - Aib | Ide - Aic |
| Ile - Ahe | Ile - Ahx | Ile - aHyl | Ile - Aib | Ile - Aib | Ile - Aic |
| Iva - Ahe | Iva - Ahx | Iva - aHyl | Iva - Aib | Iva - Aib | Iva - Aic |
| Leu - Ahe | Leu - Ahx | Leu - aHyl | Leu - Aib | Leu - Aib | Leu - Aic |
| Lys - Ahe | Lys - Ahx | Lys - aHyl | Lys - Aib | Lys - Aib | Lys - Aic |
| MeGly - Ahe | MeGly - Ahx | MeGly - aHyl | MeGly - Aib | MeGly - Aib | MeGly - Aic |
| MeIle - Ahe | MeIle - Ahx | MeIle - aHyl | MeIle - Aib | MeIle - Aib | MeIle - Aic |
| MeLys - Ahe | MeLys - Ahx | MeLys - aHyl | MeLys - Aib | MeLys - Aib | MeLys - Aic |
| Met - Ahe | Met - Ahx | Met - aHyl | Met - Aib | Met - Aib | Met - Aic |
| Met (O) - Ahe | Met (O) - Ahx | Met (O) - aHyl | Met (O) - Aib | Met (O) - Aib | Met (O) - Aic |
| Met (S—Me) - Ahe | Met (S—Me) - Ahx | Met (S—Me) - aHyl | Met (S—Me) - Aib | Met (S—Me) - Aib | Met (S—Me) - Aic |
| MeVal - Ahe | MeVal - Ahx | MeVal - aHyl | MeVal - Aib | MeVal - Aib | MeVal - Aic |
| Mpt - Ahe | Mpt - Ahx | Mpt - aHyl | Mpt - Aib | Mpt - Aib | Mpt - Aic |
| Nap - Ahe | Nap - Ahx | Nap - aHyl | Nap - Aib | Nap - Aib | Nap - Aic |
| Nle - Ahe | Nle - Ahx | Nle - aHyl | Nle - Aib | Nle - Aib | Nle - Aic |
| Nva - Ahe | Nva - Ahx | Nva - aHyl | Nva - Aib | Nva - Aib | Nva - Aic |
| Oic - Ahe | Oic - Ahx | Oic - aHyl | Oic - Aib | Oic - Aib | Oic - Aic |
| Opt - Ahe | Opt - Ahx | Opt - aHyl | Opt - Aib | Opt - Aib | Opt - Aic |
| Orn - Ahe | Orn - Ahx | Orn - aHyl | Orn - Aib | Orn - Aib | Orn - Aic |
| Pen - Ahe | Pen - Ahx | Pen - aHyl | Pen - Aib | Pen - Aib | Pen - Aic |
| Phe - Ahe | Phe - Ahx | Phe - aHyl | Phe - Aib | Phe - Aib | Phe - Aic |
| Phg - Ahe | Phg - Ahx | Phg - aHyl | Phg - Aib | Phg - Aib | Phg - Aic |
| Pip - Ahe | Pip - Ahx | Pip - aHyl | Pip - Aib | Pip - Aib | Pip - Aic |
| Pmp - Ahe | Pmp - Ahx | Pmp - aHyl | Pmp - Aib | Pmp - Aib | Pmp - Aic |
| Pro - Ahe | Pro - Ahx | Pro - aHyl | Pro - Aib | Pro - Aib | Pro - Aic |
| Qal - Ahe | Qal - Ahx | Qal - aHyl | Qal - Aib | Qal - Aib | Qal - Aic |
| Qua - Ahe | Qua - Ahx | Qua - aHyl | Qua - Aib | Qua - Aib | Qua - Aic |
| Sar - Ahe | Sar - Ahx | Sar - aHyl | Sar - Aib | Sar - Aib | Sar - Aic |
| Ser - Ahe | Ser - Ahx | Ser - aHyl | Ser - Aib | Ser - Aib | Ser - Aic |
| Thi - Ahe | Thi - Ahx | Thi - aHyl | Thi - Aib | Thi - Aib | Thi - Aic |
| Thr - Ahe | Thr - Ahx | Thr - aHyl | Thr - Aib | Thr - Aib | Thr - Aic |
| Tic - Ahe | Tic - Ahx | Tic - aHyl | Tic - Aib | Tic - Aib | Tic - Aic |
| Trp - Ahe | Trp - Ahx | Trp - aHyl | Trp - Aib | Trp - Aib | Trp - Aic |
| Tyr - Ahe | Tyr - Ahx | Tyr - aHyl | Tyr - Aib | Tyr - Aib | Tyr - Aic |
| Val - Ahe | Val - Ahx | Val - aHyl | Val - Aib | Val - Aib | Val - Aic |
| βAla - Ahe | βAla - Ahx | βAla - aHyl | βAla - Aib | βAla - Aib | βAla - Aic |
| D-TIC - aIle | D-TIC - Ala | D-TIC - Apm | D-TIC - Arg | D-TIC - Asn | D-TIC - Asp |
| GABA - aIle | GABA - Ala | GABA - Apm | GABA - Arg | GABA - Asn | GABA - Asp |
| EACA - aIle | EACA - Ala | EACA - Apm | EACA - Arg | EACA - Asn | EACA - Asp |
| K[TFA] - aIle | K[TFA] - Ala | K[TFA] - Apm | K[TFA] - Arg | K[TFA] - Asn | K[TFA] - Asp |
| 1-Nal - aIle | 1-Nal - Ala | 1-Nal - Apm | 1-Nal - Arg | 1-Nal - Asn | 1-Nal - Asp |
| 2-Nal - aIle | 2-Nal - Ala | 2-Nal - Apm | 2-Nal - Arg | 2-Nal - Asn | 2-Nal - Asp |
| 3Hyp - aIle | 3Hyp - Ala | 3Hyp - Apm | 3Hyp - Arg | 3Hyp - Asn | 3Hyp - Asp |
| 3-Pal - aIle | 3-Pal - Ala | 3-Pal - Apm | 3-Pal - Arg | 3-Pal - Asn | 3-Pal - Asp |
| 4Abu - aIle | 4Abu - Ala | 4Abu - Apm | 4Abu - Arg | 4Abu - Asn | 4Abu - Asp |
| 4Hyp - aIle | 4Hyp - Ala | 4Hyp - Apm | 4Hyp - Arg | 4Hyp - Asn | 4Hyp - Asp |
| A2bu - aIle | A2bu - Ala | A2bu - Apm | A2bu - Arg | A2bu - Asn | A2bu - Asp |
| A2pr - aIle | A2pr - Ala | A2pr - Apm | A2pr - Arg | A2pr - Asn | A2pr - Asp |
| Aad - aIle | Aad - Ala | Aad - Apm | Aad - Arg | Aad - Asn | Aad - Asp |
| aAhx - aIle | aAhx - Ala | aAhx - Apm | aAhx - Arg | aAhx - Asn | aAhx - Asp |
| Abo - aIle | Abo - Ala | Abo - Apm | Abo - Arg | Abo - Asn | Abo - Asp |
| Abu - aIle | Abu - Ala | Abu - Apm | Abu - Arg | Abu - Asn | Abu - Asp |
| ACCA - aIle | ACCA - Ala | ACCA - Apm | ACCA - Arg | ACCA - Asn | ACCA - Asp |
| Acp - aIle | Acp - Ala | Acp - Apm | Acp - Arg | Acp - Asn | Acp - Asp |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| Ahe - aIle | Ahe - Ala | Ahe - Apm | Ahe - Arg | Ahe - Asn | Ahe - Asp |
| Ahx - aIle | Ahx - Ala | Ahx - Apm | Ahx - Arg | Ahx - Asn | Ahx - Asp |
| aHyl - aIle | aHyl - Ala | aHyl - Apm | aHyl - Arg | aHyl - Asn | aHyl - Asp |
| Aib - aIle | Aib - Ala | Aib - Apm | Aib - Arg | Aib - Asn | Aib - Asp |
| Aic - aIle | Aic - Ala | Aic - Apm | Aic - Arg | Aic - Asn | Aic - Asp |
| aIle - aIle | aIle - Ala | aIle - Apm | aIle - Arg | aIle - Asn | aIle - Asp |
| Ala - aIle | Ala - Ala | Ala - Apm | Ala - Arg | Ala - Asn | Ala - Asp |
| Apm - aIle | Apm - Ala | Apm - Apm | Apm - Arg | Apm - Asn | Apm - Asp |
| Arg - aIle | Arg - Ala | Arg - Apm | Arg - Arg | Arg - Asn | Arg - Asp |
| Asn - aIle | Asn - Ala | Asn - Apm | Asn - Arg | Asn - Asn | Asn - Asp |
| Asp - aIle | Asp - Ala | Asp - Apm | Asp - Arg | Asp - Asn | Asp - Asp |
| Atc - aIle | Atc - Ala | Atc - Apm | Atc - Arg | Atc - Asn | Atc - Asp |
| Ava - aIle | Ava - Ala | Ava - Apm | Ava - Arg | Ava - Asn | Ava - Asp |
| Aze - aIle | Aze - Ala | Aze - Apm | Aze - Arg | Aze - Asn | Aze - Asp |
| bAad - aIle | bAad - Ala | bAad - Apm | bAad - Arg | bAad - Asn | bAad - Asp |
| bAib - aIle | bAib - Ala | bAib - Apm | bAib - Arg | bAib - Asn | bAib - Asp |
| bAla - aIle | bAla - Ala | bAla - Apm | bAla - Arg | bAla - Asn | bAla - Asp |
| Cha - aIle | Cha - Ala | Cha - Apm | Cha - Arg | Cha - Asn | Cha - Asp |
| Cpg - aIle | Cpg - Ala | Cpg - Apm | Cpg - Arg | Cpg - Asn | Cpg - Asp |
| Cpp - aIle | Cpp - Ala | Cpp - Apm | Cpp - Arg | Cpp - Asn | Cpp - Asp |
| cPzACAla - aIle | cPzACAla - Ala | cPzACAla - Apm | cPzACAla - Arg | cPzACAla - Asn | cPzACAla - Asp |
| Cys - aIle | Cys - Ala | Cys - Apm | Cys - Arg | Cys - Asn | Cys - Asp |
| Dap - aIle | Dap - Ala | Dap - Apm | Dap - Arg | Dap - Asn | Dap - Asp |
| Dbf - aIle | Dbf - Ala | Dbf - Apm | Dbf - Arg | Dbf - Asn | Dbf - Asp |
| Dbu - aIle | Dbu - Ala | Dbu - Apm | Dbu - Arg | Dbu - Asn | Dbu - Asp |
| Des - aIle | Des - Ala | Des - Apm | Des - Arg | Des - Asn | Des - Asp |
| Dip - aIle | Dip - Ala | Dip - Apm | Dip - Arg | Dip - Asn | Dip - Asp |
| Dph - aIle | Dph - Ala | Dph - Apm | Dph - Arg | Dph - Asn | Dph - Asp |
| Dpm - aIle | Dpm - Ala | Dpm - Apm | Dpm - Arg | Dpm - Asn | Dpm - Asp |
| Dpr - aIle | Dpr - Ala | Dpr - Apm | Dpr - Arg | Dpr - Asn | Dpr - Asp |
| EtAsn - aIle | EtAsn - Ala | EtAsn - Apm | EtAsn - Arg | EtAsn - Asn | EtAsn - Asp |
| EtGly - aIle | EtGly - Ala | EtGly - Apm | EtGly - Arg | EtGly - Asn | EtGly - Asp |
| gAbu - aIle | gAbu - Ala | gAbu - Apm | gAbu - Arg | gAbu - Asn | gAbu - Asp |
| Gln - aIle | Gln - Ala | Gln - Apm | Gln - Arg | Gln - Asn | Gln - Asp |
| Glu - aIle | Glu - Ala | Glu - Apm | Glu - Arg | Glu - Asn | Glu - Asp |
| Gly - aIle | Gly - Ala | Gly - Apm | Gly - Arg | Gly - Asn | Gly - Asp |
| Gly(Ph) - aIle | Gly(Ph) - Ala | Gly(Ph) - Apm | Gly(Ph) - Arg | Gly(Ph) - Asn | Gly(Ph) - Asp |
| Har - aIle | Har - Ala | Har - Apm | Har - Arg | Har - Asn | Har - Asp |
| Hcy - aIle | Hcy - Ala | Hcy - Apm | Hcy - Arg | Hcy - Asn | Hcy - Asp |
| Hib - aIle | Hib - Ala | Hib - Apm | Hib - Arg | Hib - Asn | Hib - Asp |
| His - aIle | His - Ala | His - Apm | His - Arg | His - Asn | His - Asp |
| Hse - aIle | Hse - Ala | Hse - Apm | Hse - Arg | Hse - Asn | Hse - Asp |
| Hyl - aIle | Hyl - Ala | Hyl - Apm | Hyl - Arg | Hyl - Asn | Hyl - Asp |
| Hyp - aIle | Hyp - Ala | Hyp - Apm | Hyp - Arg | Hyp - Asn | Hyp - Asp |
| Ide - aIle | Ide - Ala | Ide - Apm | Ide - Arg | Ide - Asn | Ide - Asp |
| Ile - aIle | Ile - Ala | Ile - Apm | Ile - Arg | Ile - Asn | Ile - Asp |
| Iva - aIle | Iva - Ala | Iva - Apm | Iva - Arg | Iva - Asn | Iva - Asp |
| Leu - aIle | Leu - Ala | Leu - Apm | Leu - Arg | Leu - Asn | Leu - Asp |
| Lys - aIle | Lys - Ala | Lys - Apm | Lys - Arg | Lys - Asn | Lys - Asp |
| MeGly - aIle | MeGly - Ala | MeGly - Apm | MeGly - Arg | MeGly - Asn | MeGly - Asp |
| MeIle - aIle | MeIle - Ala | MeIle - Apm | MeIle - Arg | MeIle - Asn | MeIle - Asp |
| MeLys - aIle | MeLys - Ala | MeLys - Apm | MeLys - Arg | MeLys - Asn | MeLys - Asp |
| Met - aIle | Met - Ala | Met - Apm | Met - Arg | Met - Asn | Met - Asp |
| Met (O) - aIle | Met (O) - Ala | Met (O) - Apm | Met (O) - Arg | Met (O) - Asn | Met (O) - Asp |
| Met (((S—Me))) - aIle | Met (((S—Me))) - Ala | Met (((S—Me))) - Apm | Met (((S—Me))) - Arg | Met (((S—Me))) - Asn | Met (((S—Me))) - Asp |
| MeVal - aIle | MeVal - Ala | MeVal - Apm | MeVal - Arg | MeVal - Asn | MeVal - Asp |
| Mpt - aIle | Mpt - Ala | Mpt - Apm | Mpt - Arg | Mpt - Asn | Mpt - Asp |
| Nap - aIle | Nap - Ala | Nap - Apm | Nap - Arg | Nap - Asn | Nap - Asp |
| Nle - aIle | Nle - Ala | Nle - Apm | Nle - Arg | Nle - Asn | Nle - Asp |
| Nva - aIle | Nva - Ala | Nva - Apm | Nva - Arg | Nva - Asn | Nva - Asp |
| Oic - aIle | Oic - Ala | Oic - Apm | Oic - Arg | Oic - Asn | Oic - Asp |
| Opt - aIle | Opt - Ala | Opt - Apm | Opt - Arg | Opt - Asn | Opt - Asp |
| Orn - aIle | Orn - Ala | Orn - Apm | Orn - Arg | Orn - Asn | Orn - Asp |
| Pen - aIle | Pen - Ala | Pen - Apm | Pen - Arg | Pen - Asn | Pen - Asp |
| Phe - aIle | Phe - Ala | Phe - Apm | Phe - Arg | Phe - Asn | Phe - Asp |
| Phg - aIle | Phg - Ala | Phg - Apm | Phg - Arg | Phg - Asn | Phg - Asp |
| Pip - aIle | Pip - Ala | Pip - Apm | Pip - Arg | Pip - Asn | Pip - Asp |
| Pmp - aIle | Pmp - Ala | Pmp - Apm | Pmp - Arg | Pmp - Asn | Pmp - Asp |
| Pro - aIle | Pro - Ala | Pro - Apm | Pro - Arg | Pro - Asn | Pro - Asp |
| Qal - aIle | Qal - Ala | Qal - Apm | Qal - Arg | Qal - Asn | Qal - Asp |
| Qua - aIle | Qua - Ala | Qua - Apm | Qua - Arg | Qua - Asn | Qua - Asp |
| Sar - aIle | Sar - Ala | Sar - Apm | Sar - Arg | Sar - Asn | Sar - Asp |
| Ser - aIle | Ser - Ala | Ser - Apm | Ser - Arg | Ser - Asn | Ser - Asp |
| Thi - aIle | Thi - Ala | Thi - Apm | Thi - Arg | Thi - Asn | Thi - Asp |

TABLE 5-continued

Illustrative combinations for $X^2 - X^3$ and/or $X^3 - X^4$.

| I-P | P-D | P-F | F-H | V-A | A-G |
|---|---|---|---|---|---|
| Thr - aIle | Thr - Ala | Thr - Apm | Thr - Arg | Thr - Asn | Thr - Asp |
| Tic - aIle | Tic - Ala | Tic - Apm | Tic - Arg | Tic - Asn | Tic - Asp |
| Trp - aIle | Trp - Ala | Trp - Apm | Trp - Arg | Trp - Asn | Trp - Asp |
| Tyr - aIle | Tyr - Ala | Tyr - Apm | Tyr - Arg | Tyr - Asn | Tyr - Asp |
| Val - aIle | Val - Ala | Val - Apm | Val - Arg | Val - Asn | Val - Asp |
| βAla - aIle | βAla - Ala | βAla - Apm | βAla - Arg | βAla - Asn | βAla - Asp |
| D-TIC - Atc | D-TIC - Ava | D-TIC - Aze | D-TIC - bAad | D-TIC - bAib | D-TIC - bAla |
| GABA - Atc | GABA - Ava | GABA - Aze | GABA - bAad | GABA - bAib | GABA - bAla |
| EACA - Atc | EACA - Ava | EACA - Aze | EACA - bAad | EACA - bAib | EACA - bAla |
| K[TFA] - Atc | K[TFA] - Ava | K[TFA] - Aze | K[TFA] - bAad | K[TFA] - bAib | K[TFA] - bAla |
| 1-Nal - Atc | 1-Nal - Ava | 1-Nal - Aze | 1-Nal - bAad | 1-Nal - bAib | 1-Nal - bAla |
| 2-Nal - Atc | 2-Nal - Ava | 2-Nal - Aze | 2-Nal - bAad | 2-Nal - bAib | 2-Nal - bAla |
| 3Hyp - Atc | 3Hyp - Ava | 3Hyp - Aze | 3Hyp - bAad | 3Hyp - bAib | 3Hyp - bAla |
| 3-Pal - Atc | 3-Pal - Ava | 3-Pal - Aze | 3-Pal - bAad | 3-Pal - bAib | 3-Pal - bAla |
| 4Abu - Atc | 4Abu - Ava | 4Abu - Aze | 4Abu - bAad | 4Abu - bAib | 4Abu - bAla |
| 4Hyp - Atc | 4Hyp - Ava | 4Hyp - Aze | 4Hyp - bAad | 4Hyp - bAib | 4Hyp - bAla |
| A2bu - Atc | A2bu - Ava | A2bu - Aze | A2bu - bAad | A2bu - bAib | A2bu - bAla |
| A2pr - Atc | A2pr - Ava | A2pr - Aze | A2pr - bAad | A2pr - bAib | A2pr - bAla |
| Aad - Atc | Aad - Ava | Aad - Aze | Aad - bAad | Aad - bAib | Aad - bAla |
| aAhx - Atc | aAhx - Ava | aAhx - Aze | aAhx - bAad | aAhx - bAib | aAhx - bAla |
| Abo - Atc | Abo - Ava | Abo - Aze | Abo - bAad | Abo - bAib | Abo - bAla |
| Abu - Atc | Abu - Ava | Abu - Aze | Abu - bAad | Abu - bAib | Abu - bAla |
| ACCA - Atc | ACCA - Ava | ACCA - Aze | ACCA - bAad | ACCA - bAib | ACCA - bAla |
| Acp - Atc | Acp - Ava | Acp - Aze | Acp - bAad | Acp - bAib | Acp - bAla |
| Ahe - Atc | Ahe - Ava | Ahe - Aze | Ahe - bAad | Ahe - bAib | Ahe - bAla |
| Ahx - Atc | Ahx - Ava | Ahx - Aze | Ahx - bAad | Ahx - bAib | Ahx - bAla |
| aHyl - Atc | aHyl - Ava | aHyl - Aze | aHyl - bAad | aHyl - bAib | aHyl - bAla |
| Aib - Atc | Aib - Ava | Aib - Aze | Aib - bAad | Aib - bAib | Aib - bAla |
| Aib - Atc | Aib - Ava | Aib - Aze | Aib - bAad | Aib - bAib | Aib - bAla |
| Aic - Atc | Aic - Ava | Aic - Aze | Aic - bAad | Aic - bAib | Aic - bAla |
| aIle - Atc | aIle - Ava | aIle - Aze | aIle - bAad | aIle - bAib | aIle - bAla |
| Ala - Atc | Ala - Ava | Ala - Aze | Ala - bAad | Ala - bAib | Ala - bAla |
| Apm - Atc | Apm - Ava | Apm - Aze | Apm - bAad | Apm - bAib | Apm - bAla |
| Arg - Atc | Arg - Ava | Arg - Aze | Arg - bAad | Arg - bAib | Arg - bAla |
| Asn - Atc | Asn - Ava | Asn - Aze | Asn - bAad | Asn - bAib | Asn - bAla |
| Asp - Atc | Asp - Ava | Asp - Aze | Asp - bAad | Asp - bAib | Asp - bAla |
| Atc - Atc | Atc - Ava | Atc - Aze | Atc - bAad | Atc - bAib | Atc - bAla |
| Ava - Atc | Ava - Ava | Ava - Aze | Ava - bAad | Ava - bAib | Ava - bAla |
| Aze - Atc | Aze - Ava | Aze - Aze | Aze - bAad | Aze - bAib | Aze - bAla |
| bAad - Atc | bAad - Ava | bAad - Aze | bAad - bAad | bAad - bAib | bAad - bAla |
| bAib - Atc | bAib - Ava | bAib - Aze | bAib - bAad | bAib - bAib | bAib - bAla |
| bAla - Atc | bAla - Ava | bAla - Aze | bAla - bAad | bAla - bAib | bAla - bAla |
| Cha - Atc | Cha - Ava | Cha - Aze | Cha - bAad | Cha - bAib | Cha - bAla |
| Cpg - Atc | Cpg - Ava | Cpg - Aze | Cpg - bAad | Cpg - bAib | Cpg - bAla |
| Cpp - Atc | Cpp - Ava | Cpp - Aze | Cpp - bAad | Cpp - bAib | Cpp - bAla |
| cPzACAla - Atc | cPzACAla - Ava | cPzACAla - Aze | cPzACAla - bAad | cPzACAla - bAib | cPzACAla - bAla |
| Cys - Atc | Cys - Ava | Cys - Aze | Cys - bAad | Cys - bAib | Cys - bAla |
| Dap - Atc | Dap - Ava | Dap - Aze | Dap - bAad | Dap - bAib | Dap - bAla |
| Dbf - Atc | Dbf - Ava | Dbf - Aze | Dbf - bAad | Dbf - bAib | Dbf - bAla |
| Dbu - Atc | Dbu - Ava | Dbu - Aze | Dbu - bAad | Dbu - bAib | Dbu - bAla |
| Des - Atc | Des - Ava | Des - Aze | Des - bAad | Des - bAib | Des - bAla |
| Dip - Atc | Dip - Ava | Dip - Aze | Dip - bAad | Dip - bAib | Dip - bAla |
| Dph - Atc | Dph - Ava | Dph - Aze | Dph - bAad | Dph - bAib | Dph - bAla |
| Dpm - Atc | Dpm - Ava | Dpm - Aze | Dpm - bAad | Dpm - bAib | Dpm - bAla |
| Dpr - Atc | Dpr - Ava | Dpr - Aze | Dpr - bAad | Dpr - bAib | Dpr - bAla |
| EtAsn - Atc | EtAsn - Ava | EtAsn - Aze | EtAsn - bAad | EtAsn - bAib | EtAsn - bAla |
| EtGly - Atc | EtGly - Ava | EtGly - Aze | EtGly - bAad | EtGly - bAib | EtGly - bAla |
| gAbu - Atc | gAbu - Ava | gAbu - Aze | gAbu - bAad | gAbu - bAib | gAbu - bAla |
| Gln - Atc | Gln - Ava | Gln - Aze | Gln - bAad | Gln - bAib | Gln - bAla |
| Glu - Atc | Glu - Ava | Glu - Aze | Glu - bAad | Glu - bAib | Glu - bAla |
| Gly - Atc | Gly - Ava | Gly - Aze | Gly - bAad | Gly - bAib | Gly - bAla |
| Gly(Ph) - Atc | Gly(Ph) - Ava | Gly(Ph) - Aze | Gly(Ph) - bAad | Gly(Ph) - bAib | Gly(Ph) - bAla |
| Har - Atc | Har - Ava | Har - Aze | Har - bAad | Har - bAib | Har - bAla |
| Hcy - Atc | Hcy - Ava | Hcy - Aze | Hcy - bAad | Hcy - bAib | Hcy - bAla |
| Hib - Atc | Hib - Ava | Hib - Aze | Hib - bAad | Hib - bAib | Hib - bAla |
| His - Atc | His - Ava | His - Aze | His - bAad | His - bAib | His - bAla |
| Hse - Atc | Hse - Ava | Hse - Aze | Hse - bAad | Hse - bAib | Hse - bAla |
| Hyl - Atc | Hyl - Ava | Hyl - Aze | Hyl - bAad | Hyl - bAib | Hyl - bAla |
| Hyp - Atc | Hyp - Ava | Hyp - Aze | Hyp - bAad | Hyp - bAib | Hyp - bAla |
| Ide - Atc | Ide - Ava | Ide - Aze | Ide - bAad | Ide - bAib | Ide - bAla |
| Ile - Atc | Ile - Ava | Ile - Aze | Ile - bAad | Ile - bAib | Ile - bAla |
| Iva - Atc | Iva - Ava | Iva - Aze | Iva - bAad | Iva - bAib | Iva - bAla |
| Leu - Atc | Leu - Ava | Leu - Aze | Leu - bAad | Leu - bAib | Leu - bAla |
| Lys - Atc | Lys - Ava | Lys - Aze | Lys - bAad | Lys - bAib | Lys - bAla |
| MeGly - Atc | MeGly - Ava | MeGly - Aze | MeGly - bAad | MeGly - bAib | MeGly - bAla |
| MeIle - Atc | MeIle - Ava | MeIle - Aze | MeIle - bAad | MeIle - bAib | MeIle - bAla |

TABLE 5-continued

Illustrative combinations for $X^2 - X^3$ and/or $X^3 - X^4$.

| I-P | P-D | P-F | F-H | V-A | A-G |
|---|---|---|---|---|---|
| MeLys - Atc | MeLys - Ava | MeLys - Aze | MeLys - bAad | MeLys - bAib | MeLys - bAla |
| Met - Atc | Met - Ava | Met - Aze | Met - bAad | Met - bAib | Met - bAla |
| Met (O) - Atc | Met (O) - Ava | Met (O) - Aze | Met (O) - bAad | Met (O) - bAib | Met (O) - bAla |
| Met (((S—Me))) - Atc | Met (((S—Me))) - Ava | Met (((S—Me))) - Aze | Met (((S—Me))) - bAad | Met (((S—Me))) - bAib | Met (((S—Me))) - bAla |
| MeVal - Atc | MeVal - Ava | MeVal - Aze | MeVal - bAad | MeVal - bAib | MeVal - bAla |
| Mpt - Atc | Mpt - Ava | Mpt - Aze | Mpt - bAad | Mpt - bAib | Mpt - bAla |
| Nap - Atc | Nap - Ava | Nap - Aze | Nap - bAad | Nap - bAib | Nap - bAla |
| Nle - Atc | Nle - Ava | Nle - Aze | Nle - bAad | Nle - bAib | Nle - bAla |
| Nva - Atc | Nva - Ava | Nva - Aze | Nva - bAad | Nva - bAib | Nva - bAla |
| Oic - Atc | Oic - Ava | Oic - Aze | Oic - bAad | Oic - bAib | Oic - bAla |
| Opt - Atc | Opt - Ava | Opt - Aze | Opt - bAad | Opt - bAib | Opt - bAla |
| Orn - Atc | Orn - Ava | Orn - Aze | Orn - bAad | Orn - bAib | Orn - bAla |
| Pen - Atc | Pen - Ava | Pen - Aze | Pen - bAad | Pen - bAib | Pen - bAla |
| Phe - Atc | Phe - Ava | Phe - Aze | Phe - bAad | Phe - bAib | Phe - bAla |
| Phg - Atc | Phg - Ava | Phg - Aze | Phg - bAad | Phg - bAib | Phg - bAla |
| Pip - Atc | Pip - Ava | Pip - Aze | Pip - bAad | Pip - bAib | Pip - bAla |
| Pmp - Atc | Pmp - Ava | Pmp - Aze | Pmp - bAad | Pmp - bAib | Pmp - bAla |
| Pro - Atc | Pro - Ava | Pro - Aze | Pro - bAad | Pro - bAib | Pro - bAla |
| Qal - Atc | Qal - Ava | Qal - Aze | Qal - bAad | Qal - bAib | Qal - bAla |
| Qua - Atc | Qua - Ava | Qua - Aze | Qua - bAad | Qua - bAib | Qua - bAla |
| Sar - Atc | Sar - Ava | Sar - Aze | Sar - bAad | Sar - bAib | Sar - bAla |
| Ser - Atc | Ser - Ava | Ser - Aze | Ser - bAad | Ser - bAib | Ser - bAla |
| Thi - Atc | Thi - Ava | Thi - Aze | Thi - bAad | Thi - bAib | Thi - bAla |
| Thr - Atc | Thr - Ava | Thr - Aze | Thr - bAad | Thr - bAib | Thr - bAla |
| Tic - Atc | Tic - Ava | Tic - Aze | Tic - bAad | Tic - bAib | Tic - bAla |
| Trp - Atc | Trp - Ava | Trp - Aze | Trp - bAad | Trp - bAib | Trp - bAla |
| Tyr - Atc | Tyr - Ava | Tyr - Aze | Tyr - bAad | Tyr - bAib | Tyr - bAla |
| Val - Atc | Val - Ava | Val - Aze | Val - bAad | Val - bAib | Val - bAla |
| βAla - Atc | βAla - Ava | βAla - Aze | βAla - bAad | βAla - bAib | βAla - bAla |
| D-TIC - Cha | D-TIC - Cpg | D-TIC - Cpp | D-TIC - cPzACAla | D-TIC - Cys | D-TIC - Dap |
| GABA - Cha | GABA - Cpg | GABA - Cpp | GABA - cPzACAla | GABA - Cys | GABA - Dap |
| EACA - Cha | EACA - Cpg | EACA - Cpp | EACA - cPzACAla | EACA - Cys | EACA - Dap |
| K[TFA] - Cha | K[TFA] - Cpg | K[TFA] - Cpp | K[TFA] - cPzACAla | K[TFA] - Cys | K[TFA] - Dap |
| 1-Nal - Cha | 1-Nal - Cpg | 1-Nal - Cpp | 1-Nal - cPzACAla | 1-Nal - Cys | 1-Nal - Dap |
| 2-Nal - Cha | 2-Nal - Cpg | 2-Nal - Cpp | 2-Nal - cPzACAla | 2-Nal - Cys | 2-Nal - Dap |
| 3Hyp - Cha | 3Hyp - Cpg | 3Hyp - Cpp | 3Hyp - cPzACAla | 3Hyp - Cys | 3Hyp - Dap |
| 3-Pal - Cha | 3-Pal - Cpg | 3-Pal - Cpp | 3-Pal - cPzACAla | 3-Pal - Cys | 3-Pal - Dap |
| 4Abu - Cha | 4Abu - Cpg | 4Abu - Cpp | 4Abu - cPzACAla | 4Abu - Cys | 4Abu - Dap |
| 4Hyp - Cha | 4Hyp - Cpg | 4Hyp - Cpp | 4Hyp - cPzACAla | 4Hyp - Cys | 4Hyp - Dap |
| A2bu - Cha | A2bu - Cpg | A2bu - Cpp | A2bu - cPzACAla | A2bu - Cys | A2bu - Dap |
| A2pr - Cha | A2pr - Cpg | A2pr - Cpp | A2pr - cPzACAla | A2pr - Cys | A2pr - Dap |
| Aad - Cha | Aad - Cpg | Aad - Cpp | Aad - cPzACAla | Aad - Cys | Aad - Dap |
| aAhx - Cha | aAhx - Cpg | aAhx - Cpp | aAhx - cPzACAla | aAhx - Cys | aAhx - Dap |
| Abo - Cha | Abo - Cpg | Abo - Cpp | Abo - cPzACAla | Abo - Cys | Abo - Dap |
| Abu - Cha | Abu - Cpg | Abu - Cpp | Abu - cPzACAla | Abu - Cys | Abu - Dap |
| ACCA - Cha | ACCA - Cpg | ACCA - Cpp | ACCA - cPzACAla | ACCA - Cys | ACCA - Dap |
| Acp - Cha | Acp - Cpg | Acp - Cpp | Acp - cPzACAla | Acp - Cys | Acp - Dap |
| Ahe - Cha | Ahe - Cpg | Ahe - Cpp | Ahe - cPzACAla | Ahe - Cys | Ahe - Dap |
| Ahx - Cha | Ahx - Cpg | Ahx - Cpp | Ahx - cPzACAla | Ahx - Cys | Ahx - Dap |
| aHyl - Cha | aHyl - Cpg | aHyl - Cpp | aHyl - cPzACAla | aHyl - Cys | aHyl - Dap |
| Aib - Cha | Aib - Cpg | Aib - Cpp | Aib - cPzACAla | Aib - Cys | Aib - Dap |
| Aib - Cha | Aib - Cpg | Aib - Cpp | Aib - cPzACAla | Aib - Cys | Aib - Dap |
| Aic - Cha | Aic - Cpg | Aic - Cpp | Aic - cPzACAla | Aic - Cys | Aic - Dap |
| aIle - Cha | aIle - Cpg | aIle - Cpp | aIle - cPzACAla | aIle - Cys | aIle - Dap |
| Ala - Cha | Ala - Cpg | Ala - Cpp | Ala - cPzACAla | Ala - Cys | Ala - Dap |
| Apm - Cha | Apm - Cpg | Apm - Cpp | Apm - cPzACAla | Apm - Cys | Apm - Dap |
| Arg - Cha | Arg - Cpg | Arg - Cpp | Arg - cPzACAla | Arg - Cys | Arg - Dap |
| Asn - Cha | Asn - Cpg | Asn - Cpp | Asn - cPzACAla | Asn - Cys | Asn - Dap |
| Asp - Cha | Asp - Cpg | Asp - Cpp | Asp - cPzACAla | Asp - Cys | Asp - Dap |
| Atc - Cha | Atc - Cpg | Atc - Cpp | Atc - cPzACAla | Atc - Cys | Atc - Dap |
| Ava - Cha | Ava - Cpg | Ava - Cpp | Ava - cPzACAla | Ava - Cys | Ava - Dap |
| Aze - Cha | Aze - Cpg | Aze - Cpp | Aze - cPzACAla | Aze - Cys | Aze - Dap |
| bAad - Cha | bAad - Cpg | bAad - Cpp | bAad - cPzACAla | bAad - Cys | bAad - Dap |
| bAib - Cha | bAib - Cpg | bAib - Cpp | bAib - cPzACAla | bAib - Cys | bAib - Dap |
| bAla - Cha | bAla - Cpg | bAla - Cpp | bAla - cPzACAla | bAla - Cys | bAla - Dap |
| Cha - Cha | Cha - Cpg | Cha - Cpp | Cha - cPzACAla | Cha - Cys | Cha - Dap |
| Cpg - Cha | Cpg - Cpg | Cpg - Cpp | Cpg - cPzACAla | Cpg - Cys | Cpg - Dap |
| Cpp - Cha | Cpp - Cpg | Cpp - Cpp | Cpp - cPzACAla | Cpp - Cys | Cpp - Dap |
| cPzACAla - Cha | cPzACAla - Cpg | cPzACAla - Cpp | cPzACAla - cPzACAla | cPzACAla - Cys | cPzACAla - Dap |
| Cys - Cha | Cys - Cpg | Cys - Cpp | Cys - cPzACAla | Cys - Cys | Cys - Dap |
| Dap - Cha | Dap - Cpg | Dap - Cpp | Dap - cPzACAla | Dap - Cys | Dap - Dap |
| Dbf - Cha | Dbf - Cpg | Dbf - Cpp | Dbf - cPzACAla | Dbf - Cys | Dbf - Dap |
| Dbu - Cha | Dbu - Cpg | Dbu - Cpp | Dbu - cPzACAla | Dbu - Cys | Dbu - Dap |
| Des - Cha | Des - Cpg | Des - Cpp | Des - cPzACAla | Des - Cys | Des - Dap |
| Dip - Cha | Dip - Cpg | Dip - Cpp | Dip - cPzACAla | Dip - Cys | Dip - Dap |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| Dph - Cha | Dph - Cpg | Dph - Cpp | Dph - cPzACAla | Dph - Cys | Dph - Dap |
| Dpm - Cha | Dpm - Cpg | Dpm - Cpp | Dpm - cPzACAla | Dpm - Cys | Dpm - Dap |
| Dpr - Cha | Dpr - Cpg | Dpr - Cpp | Dpr - cPzACAla | Dpr - Cys | Dpr - Dap |
| EtAsn - Cha | EtAsn - Cpg | EtAsn - Cpp | EtAsn - cPzACAla | EtAsn - Cys | EtAsn - Dap |
| EtGly - Cha | EtGly - Cpg | EtGly - Cpp | EtGly - cPzACAla | EtGly - Cys | EtGly - Dap |
| gAbu - Cha | gAbu - Cpg | gAbu - Cpp | gAbu - cPzACAla | gAbu - Cys | gAbu - Dap |
| Gln - Cha | Gln - Cpg | Gln - Cpp | Gln - cPzACAla | Gln - Cys | Gln - Dap |
| Glu - Cha | Glu - Cpg | Glu - Cpp | Glu - cPzACAla | Glu - Cys | Glu - Dap |
| Gly - Cha | Gly - Cpg | Gly - Cpp | Gly - cPzACAla | Gly - Cys | Gly - Dap |
| Gly(Ph) - Cha | Gly(Ph) - Cpg | Gly(Ph) - Cpp | Gly(Ph) - cPzACAla | Gly(Ph) - Cys | Gly(Ph) - Dap |
| Har - Cha | Har - Cpg | Har - Cpp | Har - cPzACAla | Har - Cys | Har - Dap |
| Hcy - Cha | Hcy - Cpg | Hcy - Cpp | Hcy - cPzACAla | Hcy - Cys | Hcy - Dap |
| Hib - Cha | Hib - Cpg | Hib - Cpp | Hib - cPzACAla | Hib - Cys | Hib - Dap |
| His - Cha | His - Cpg | His - Cpp | His - cPzACAla | His - Cys | His - Dap |
| Hse - Cha | Hse - Cpg | Hse - Cpp | Hse - cPzACAla | Hse - Cys | Hse - Dap |
| Hyl - Cha | Hyl - Cpg | Hyl - Cpp | Hyl - cPzACAla | Hyl - Cys | Hyl - Dap |
| Hyp - Cha | Hyp - Cpg | Hyp - Cpp | Hyp - cPzACAla | Hyp - Cys | Hyp - Dap |
| Ide - Cha | Ide - Cpg | Ide - Cpp | Ide - cPzACAla | Ide - Cys | Ide - Dap |
| Ile - Cha | Ile - Cpg | Ile - Cpp | Ile - cPzACAla | Ile - Cys | Ile - Dap |
| Iva - Cha | Iva - Cpg | Iva - Cpp | Iva - cPzACAla | Iva - Cys | Iva - Dap |
| Leu - Cha | Leu - Cpg | Leu - Cpp | Leu - cPzACAla | Leu - Cys | Leu - Dap |
| Lys - Cha | Lys - Cpg | Lys - Cpp | Lys - cPzACAla | Lys - Cys | Lys - Dap |
| MeGly - Cha | MeGly - Cpg | MeGly - Cpp | MeGly - cPzACAla | MeGly - Cys | MeGly - Dap |
| MeIle - Cha | MeIle - Cpg | MeIle - Cpp | MeIle - cPzACAla | MeIle - Cys | MeIle - Dap |
| MeLys - Cha | MeLys - Cpg | MeLys - Cpp | MeLys - cPzACAla | MeLys - Cys | MeLys - Dap |
| Met - Cha | Met - Cpg | Met - Cpp | Met - cPzACAla | Met - Cys | Met - Dap |
| Met (O) - Cha | Met (O) - Cpg | Met (O) - Cpp | Met (O) - cPzACAla | Met (O) - Cys | Met (O) - Dap |
| Met (S—Me) - Cha | Met (S—Me) - Cpg | Met (S—Me) - Cpp | Met (S—Me) - cPzACAla | Met (S—Me) - Cys | Met (S—Me) - Dap |
| MeVal - Cha | MeVal - Cpg | MeVal - Cpp | MeVal - cPzACAla | MeVal - Cys | MeVal - Dap |
| Mpt - Cha | Mpt - Cpg | Mpt - Cpp | Mpt - cPzACAla | Mpt - Cys | Mpt - Dap |
| Nap - Cha | Nap - Cpg | Nap - Cpp | Nap - cPzACAla | Nap - Cys | Nap - Dap |
| Nle - Cha | Nle - Cpg | Nle - Cpp | Nle - cPzACAla | Nle - Cys | Nle - Dap |
| Nva - Cha | Nva - Cpg | Nva - Cpp | Nva - cPzACAla | Nva - Cys | Nva - Dap |
| Oic - Cha | Oic - Cpg | Oic - Cpp | Oic - cPzACAla | Oic - Cys | Oic - Dap |
| Opt - Cha | Opt - Cpg | Opt - Cpp | Opt - cPzACAla | Opt - Cys | Opt - Dap |
| Orn - Cha | Orn - Cpg | Orn - Cpp | Orn - cPzACAla | Orn - Cys | Orn - Dap |
| Pen - Cha | Pen - Cpg | Pen - Cpp | Pen - cPzACAla | Pen - Cys | Pen - Dap |
| Phe - Cha | Phe - Cpg | Phe - Cpp | Phe - cPzACAla | Phe - Cys | Phe - Dap |
| Phg - Cha | Phg - Cpg | Phg - Cpp | Phg - cPzACAla | Phg - Cys | Phg - Dap |
| Pip - Cha | Pip - Cpg | Pip - Cpp | Pip - cPzACAla | Pip - Cys | Pip - Dap |
| Pmp - Cha | Pmp - Cpg | Pmp - Cpp | Pmp - cPzACAla | Pmp - Cys | Pmp - Dap |
| Pro - Cha | Pro - Cpg | Pro - Cpp | Pro - cPzACAla | Pro - Cys | Pro - Dap |
| Qal - Cha | Qal - Cpg | Qal - Cpp | Qal - cPzACAla | Qal - Cys | Qal - Dap |
| Qua - Cha | Qua - Cpg | Qua - Cpp | Qua - cPzACAla | Qua - Cys | Qua - Dap |
| Sar - Cha | Sar - Cpg | Sar - Cpp | Sar - cPzACAla | Sar - Cys | Sar - Dap |
| Ser - Cha | Ser - Cpg | Ser - Cpp | Ser - cPzACAla | Ser - Cys | Ser - Dap |
| Thi - Cha | Thi - Cpg | Thi - Cpp | Thi - cPzACAla | Thi - Cys | Thi - Dap |
| Thr - Cha | Thr - Cpg | Thr - Cpp | Thr - cPzACAla | Thr - Cys | Thr - Dap |
| Tic - Cha | Tic - Cpg | Tic - Cpp | Tic - cPzACAla | Tic - Cys | Tic - Dap |
| Trp - Cha | Trp - Cpg | Trp - Cpp | Trp - cPzACAla | Trp - Cys | Trp - Dap |
| Tyr - Cha | Tyr - Cpg | Tyr - Cpp | Tyr - cPzACAla | Tyr - Cys | Tyr - Dap |
| Val - Cha | Val - Cpg | Val - Cpp | Val - cPzACAla | Val - Cys | Val - Dap |
| βAla - Cha | βAla - Cpg | βAla - Cpp | βAla - cPzACAla | βAla - Cys | βAla - Dap |
| D-TIC - Dbf | D-TIC - Dbu | D-TIC - Des | D-TIC - Dip | D-TIC - Dph | D-TIC - Dpm |
| GABA - Dbf | GABA - Dbu | GABA - Des | GABA - Dip | GABA - Dph | GABA - Dpm |
| EACA - Dbf | EACA - Dbu | EACA - Des | EACA - Dip | EACA - Dph | EACA - Dpm |
| K[TFA] - Dbf | K[TFA] - Dbu | K[TFA] - Des | K[TFA] - Dip | K[TFA] - Dph | K[TFA] - Dpm |
| 1-Nal - Dbf | 1-Nal - Dbu | 1-Nal - Des | 1-Nal - Dip | 1-Nal - Dph | 1-Nal - Dpm |
| 2-Nal - Dbf | 2-Nal - Dbu | 2-Nal - Des | 2-Nal - Dip | 2-Nal - Dph | 2-Nal - Dpm |
| 3Hyp - Dbf | 3Hyp - Dbu | 3Hyp - Des | 3Hyp - Dip | 3Hyp - Dph | 3Hyp - Dpm |
| 3-Pal - Dbf | 3-Pal - Dbu | 3-Pal - Des | 3-Pal - Dip | 3-Pal - Dph | 3-Pal - Dpm |
| 4Abu - Dbf | 4Abu - Dbu | 4Abu - Des | 4Abu - Dip | 4Abu - Dph | 4Abu - Dpm |
| 4Hyp - Dbf | 4Hyp - Dbu | 4Hyp - Des | 4Hyp - Dip | 4Hyp - Dph | 4Hyp - Dpm |
| A2bu - Dbf | A2bu - Dbu | A2bu - Des | A2bu - Dip | A2bu - Dph | A2bu - Dpm |
| A2pr - Dbf | A2pr - Dbu | A2pr - Des | A2pr - Dip | A2pr - Dph | A2pr - Dpm |
| Aad - Dbf | Aad - Dbu | Aad - Des | Aad - Dip | Aad - Dph | Aad - Dpm |
| aAhx - Dbf | aAhx - Dbu | aAhx - Des | aAhx - Dip | aAhx - Dph | aAhx - Dpm |
| Abo - Dbf | Abo - Dbu | Abo - Des | Abo - Dip | Abo - Dph | Abo - Dpm |
| Abu - Dbf | Abu - Dbu | Abu - Des | Abu - Dip | Abu - Dph | Abu - Dpm |
| ACCA - Dbf | ACCA - Dbu | ACCA - Des | ACCA - Dip | ACCA - Dph | ACCA - Dpm |
| Acp - Dbf | Acp - Dbu | Acp - Des | Acp - Dip | Acp - Dph | Acp - Dpm |
| Ahe - Dbf | Ahe - Dbu | Ahe - Des | Ahe - Dip | Ahe - Dph | Ahe - Dpm |
| Ahx - Dbf | Ahx - Dbu | Ahx - Des | Ahx - Dip | Ahx - Dph | Ahx - Dpm |
| aHyl - Dbf | aHyl - Dbu | aHyl - Des | aHyl - Dip | aHyl - Dph | aHyl - Dpm |
| Aib - Dbf | Aib - Dbu | Aib - Des | Aib - Dip | Aib - Dph | Aib - Dpm |

TABLE 5-continued

Illustrative combinations for $X^2 - X^3$ and/or $X^3 - X^4$.

| I-P | P-D | P-F | F-H | V-A | A-G |
|---|---|---|---|---|---|
| Aib - Dbf | Aib - Dbu | Aib - Des | Aib - Dip | Aib - Dph | Aib - Dpm |
| Aic - Dbf | Aic - Dbu | Aic - Des | Aic - Dip | Aic - Dph | Aic - Dpm |
| aIle - Dbf | aIle - Dbu | aIle - Des | aIle - Dip | aIle - Dph | aIle - Dpm |
| Ala - Dbf | Ala - Dbu | Ala - Des | Ala - Dip | Ala - Dph | Ala - Dpm |
| Apm - Dbf | Apm - Dbu | Apm - Des | Apm - Dip | Apm - Dph | Apm - Dpm |
| Arg - Dbf | Arg - Dbu | Arg - Des | Arg - Dip | Arg - Dph | Arg - Dpm |
| Asn - Dbf | Asn - Dbu | Asn - Des | Asn - Dip | Asn - Dph | Asn - Dpm |
| Asp - Dbf | Asp - Dbu | Asp - Des | Asp - Dip | Asp - Dph | Asp - Dpm |
| Atc - Dbf | Atc - Dbu | Atc - Des | Atc - Dip | Atc - Dph | Atc - Dpm |
| Ava - Dbf | Ava - Dbu | Ava - Des | Ava - Dip | Ava - Dph | Ava - Dpm |
| Aze - Dbf | Aze - Dbu | Aze - Des | Aze - Dip | Aze - Dph | Aze - Dpm |
| bAad - Dbf | bAad - Dbu | bAad - Des | bAad - Dip | bAad - Dph | bAad - Dpm |
| bAib - Dbf | bAib - Dbu | bAib - Des | bAib - Dip | bAib - Dph | bAib - Dpm |
| bAla - Dbf | bAla - Dbu | bAla - Des | bAla - Dip | bAla - Dph | bAla - Dpm |
| Cha - Dbf | Cha - Dbu | Cha - Des | Cha - Dip | Cha - Dph | Cha - Dpm |
| Cpg - Dbf | Cpg - Dbu | Cpg - Des | Cpg - Dip | Cpg - Dph | Cpg - Dpm |
| Cpp - Dbf | Cpp - Dbu | Cpp - Des | Cpp - Dip | Cpp - Dph | Cpp - Dpm |
| cPzACAla - Dbf | cPzACAla - Dbu | cPzACAla - Des | cPzACAla - Dip | cPzACAla - Dph | cPzACAla - Dpm |
| Cys - Dbf | Cys - Dbu | Cys - Des | Cys - Dip | Cys - Dph | Cys - Dpm |
| Dap - Dbf | Dap - Dbu | Dap - Des | Dap - Dip | Dap - Dph | Dap - Dpm |
| Dbf - Dbf | Dbf - Dbu | Dbf - Des | Dbf - Dip | Dbf - Dph | Dbf - Dpm |
| Dbu - Dbf | Dbu - Dbu | Dbu - Des | Dbu - Dip | Dbu - Dph | Dbu - Dpm |
| Des - Dbf | Des - Dbu | Des - Des | Des - Dip | Des - Dph | Des - Dpm |
| Dip - Dbf | Dip - Dbu | Dip - Des | Dip - Dip | Dip - Dph | Dip - Dpm |
| Dph - Dbf | Dph - Dbu | Dph - Des | Dph - Dip | Dph - Dph | Dph - Dpm |
| Dpm - Dbf | Dpm - Dbu | Dpm - Des | Dpm - Dip | Dpm - Dph | Dpm - Dpm |
| Dpr - Dbf | Dpr - Dbu | Dpr - Des | Dpr - Dip | Dpr - Dph | Dpr - Dpm |
| EtAsn - Dbf | EtAsn - Dbu | EtAsn - Des | EtAsn - Dip | EtAsn - Dph | EtAsn - Dpm |
| EtGly - Dbf | EtGly - Dbu | EtGly - Des | EtGly - Dip | EtGly - Dph | EtGly - Dpm |
| gAbu - Dbf | gAbu - Dbu | gAbu - Des | gAbu - Dip | gAbu - Dph | gAbu - Dpm |
| Gln - Dbf | Gln - Dbu | Gln - Des | Gln - Dip | Gln - Dph | Gln - Dpm |
| Glu - Dbf | Glu - Dbu | Glu - Des | Glu - Dip | Glu - Dph | Glu - Dpm |
| Gly - Dbf | Gly - Dbu | Gly - Des | Gly - Dip | Gly - Dph | Gly - Dpm |
| Gly(Ph) - Dbf | Gly(Ph) - Dbu | Gly(Ph) - Des | Gly(Ph) - Dip | Gly(Ph) - Dph | Gly(Ph) - Dpm |
| Har - Dbf | Har - Dbu | Har - Des | Har - Dip | Har - Dph | Har - Dpm |
| Hcy - Dbf | Hcy - Dbu | Hcy - Des | Hcy - Dip | Hcy - Dph | Hcy - Dpm |
| Hib - Dbf | Hib - Dbu | Hib - Des | Hib - Dip | Hib - Dph | Hib - Dpm |
| His - Dbf | His - Dbu | His - Des | His - Dip | His - Dph | His - Dpm |
| Hse - Dbf | Hse - Dbu | Hse - Des | Hse - Dip | Hse - Dph | Hse - Dpm |
| Hyl - Dbf | Hyl - Dbu | Hyl - Des | Hyl - Dip | Hyl - Dph | Hyl - Dpm |
| Hyp - Dbf | Hyp - Dbu | Hyp - Des | Hyp - Dip | Hyp - Dph | Hyp - Dpm |
| Ide - Dbf | Ide - Dbu | Ide - Des | Ide - Dip | Ide - Dph | Ide - Dpm |
| Ile - Dbf | Ile - Dbu | Ile - Des | Ile - Dip | Ile - Dph | Ile - Dpm |
| Iva - Dbf | Iva - Dbu | Iva - Des | Iva - Dip | Iva - Dph | Iva - Dpm |
| Leu - Dbf | Leu - Dbu | Leu - Des | Leu - Dip | Leu - Dph | Leu - Dpm |
| Lys - Dbf | Lys - Dbu | Lys - Des | Lys - Dip | Lys - Dph | Lys - Dpm |
| MeGly - Dbf | MeGly - Dbu | MeGly - Des | MeGly - Dip | MeGly - Dph | MeGly - Dpm |
| MeIle - Dbf | MeIle - Dbu | MeIle - Des | MeIle - Dip | MeIle - Dph | MeIle - Dpm |
| MeLys - Dbf | MeLys - Dbu | MeLys - Des | MeLys - Dip | MeLys - Dph | MeLys - Dpm |
| Met - Dbf | Met - Dbu | Met - Des | Met - Dip | Met - Dph | Met - Dpm |
| Met (O) - Dbf | Met (O) - Dbu | Met (O) - Des | Met (O) - Dip | Met (O) - Dph | Met (O) - Dpm |
| Met (S—Me) - Dbf | Met (S—Me) - Dbu | Met (S—Me) - Des | Met (S—Me) - Dip | Met (S—Me) - Dph | Met (S—Me) - Dpm |
| MeVal - Dbf | MeVal - Dbu | MeVal - Des | MeVal - Dip | MeVal - Dph | MeVal - Dpm |
| Mpt - Dbf | Mpt - Dbu | Mpt - Des | Mpt - Dip | Mpt - Dph | Mpt - Dpm |
| Nap - Dbf | Nap - Dbu | Nap - Des | Nap - Dip | Nap - Dph | Nap - Dpm |
| Nle - Dbf | Nle - Dbu | Nle - Des | Nle - Dip | Nle - Dph | Nle - Dpm |
| Nva - Dbf | Nva - Dbu | Nva - Des | Nva - Dip | Nva - Dph | Nva - Dpm |
| Oic - Dbf | Oic - Dbu | Oic - Des | Oic - Dip | Oic - Dph | Oic - Dpm |
| Opt - Dbf | Opt - Dbu | Opt - Des | Opt - Dip | Opt - Dph | Opt - Dpm |
| Orn - Dbf | Orn - Dbu | Orn - Des | Orn - Dip | Orn - Dph | Orn - Dpm |
| Pen - Dbf | Pen - Dbu | Pen - Des | Pen - Dip | Pen - Dph | Pen - Dpm |
| Phe - Dbf | Phe - Dbu | Phe - Des | Phe - Dip | Phe - Dph | Phe - Dpm |
| Phg - Dbf | Phg - Dbu | Phg - Des | Phg - Dip | Phg - Dph | Phg - Dpm |
| Pip - Dbf | Pip - Dbu | Pip - Des | Pip - Dip | Pip - Dph | Pip - Dpm |
| Pmp - Dbf | Pmp - Dbu | Pmp - Des | Pmp - Dip | Pmp - Dph | Pmp - Dpm |
| Pro - Dbf | Pro - Dbu | Pro - Des | Pro - Dip | Pro - Dph | Pro - Dpm |
| Qal - Dbf | Qal - Dbu | Qal - Des | Qal - Dip | Qal - Dph | Qal - Dpm |
| Qua - Dbf | Qua - Dbu | Qua - Des | Qua - Dip | Qua - Dph | Qua - Dpm |
| Sar - Dbf | Sar - Dbu | Sar - Des | Sar - Dip | Sar - Dph | Sar - Dpm |
| Ser - Dbf | Ser - Dbu | Ser - Des | Ser - Dip | Ser - Dph | Ser - Dpm |
| Thi - Dbf | Thi - Dbu | Thi - Des | Thi - Dip | Thi - Dph | Thi - Dpm |
| Thr - Dbf | Thr - Dbu | Thr - Des | Thr - Dip | Thr - Dph | Thr - Dpm |
| Tic - Dbf | Tic - Dbu | Tic - Des | Tic - Dip | Tic - Dph | Tic - Dpm |
| Trp - Dbf | Trp - Dbu | Trp - Des | Trp - Dip | Trp - Dph | Trp - Dpm |
| Tyr - Dbf | Tyr - Dbu | Tyr - Des | Tyr - Dip | Tyr - Dph | Tyr - Dpm |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| Val - Dbf | Val - Dbu | Val - Des | Val - Dip | Val - Dph | Val - Dpm |
| βAla - Dbf | βAla - Dbu | βAla - Des | βAla - Dip | βAla - Dph | βAla - Dpm |
| D-TIC - Dpr | D-TIC - EtAsn | D-TIC - EtGly | D-TIC - gAbu | D-TIC - Gln | D-TIC - Glu |
| GABA - Dpr | GABA - EtAsn | GABA - EtGly | GABA - gAbu | GABA - Gln | GABA - Glu |
| EACA - Dpr | EACA - EtAsn | EACA - EtGly | EACA - gAbu | EACA - Gln | EACA - Glu |
| K[TFA] - Dpr | K[TFA] - EtAsn | K[TFA] - EtGly | K[TFA] - gAbu | K[TFA] - Gln | K[TFA] - Glu |
| 1-Nal - Dpr | 1-Nal - EtAsn | 1-Nal - EtGly | 1-Nal - gAbu | 1-Nal - Gln | 1-Nal - Glu |
| 2-Nal - Dpr | 2-Nal - EtAsn | 2-Nal - EtGly | 2-Nal - gAbu | 2-Nal - Gln | 2-Nal - Glu |
| 3Hyp - Dpr | 3Hyp - EtAsn | 3Hyp - EtGly | 3Hyp - gAbu | 3Hyp - Gln | 3Hyp - Glu |
| 3-Pal - Dpr | 3-Pal - EtAsn | 3-Pal - EtGly | 3-Pal - gAbu | 3-Pal - Gln | 3-Pal - Glu |
| 4Abu - Dpr | 4Abu - EtAsn | 4Abu - EtGly | 4Abu - gAbu | 4Abu - Gln | 4Abu - Glu |
| 4Hyp - Dpr | 4Hyp - EtAsn | 4Hyp - EtGly | 4Hyp - gAbu | 4Hyp - Gln | 4Hyp - Glu |
| A2bu - Dpr | A2bu - EtAsn | A2bu - EtGly | A2bu - gAbu | A2bu - Gln | A2bu - Glu |
| A2pr - Dpr | A2pr - EtAsn | A2pr - EtGly | A2pr - gAbu | A2pr - Gln | A2pr - Glu |
| Aad - Dpr | Aad - EtAsn | Aad - EtGly | Aad - gAbu | Aad - Gln | Aad - Glu |
| aAhx - Dpr | aAhx - EtAsn | aAhx - EtGly | aAhx - gAbu | aAhx - Gln | aAhx - Glu |
| Abo - Dpr | Abo - EtAsn | Abo - EtGly | Abo - gAbu | Abo - Gln | Abo - Glu |
| Abu - Dpr | Abu - EtAsn | Abu - EtGly | Abu - gAbu | Abu - Gln | Abu - Glu |
| ACCA - Dpr | ACCA - EtAsn | ACCA - EtGly | ACCA - gAbu | ACCA - Gln | ACCA - Glu |
| Acp - Dpr | Acp - EtAsn | Acp - EtGly | Acp - gAbu | Acp - Gln | Acp - Glu |
| Ahe - Dpr | Ahe - EtAsn | Ahe - EtGly | Ahe - gAbu | Ahe - Gln | Ahe - Glu |
| Ahx - Dpr | Ahx - EtAsn | Ahx - EtGly | Ahx - gAbu | Ahx - Gln | Ahx - Glu |
| aHyl - Dpr | aHyl - EtAsn | aHyl - EtGly | aHyl - gAbu | aHyl - Gln | aHyl - Glu |
| Aib - Dpr | Aib - EtAsn | Aib - EtGly | Aib - gAbu | Aib - Gln | Aib - Glu |
| Aib - Dpr | Aib - EtAsn | Aib - EtGly | Aib - gAbu | Aib - Gln | Aib - Glu |
| Aic - Dpr | Aic - EtAsn | Aic - EtGly | Aic - gAbu | Aic - Gln | Aic - Glu |
| aIle - Dpr | aIle - EtAsn | aIle - EtGly | aIle - gAbu | aIle - Gln | aIle - Glu |
| Ala - Dpr | Ala - EtAsn | Ala - EtGly | Ala - gAbu | Ala - Gln | Ala - Glu |
| Apm - Dpr | Apm - EtAsn | Apm - EtGly | Apm - gAbu | Apm - Gln | Apm - Glu |
| Arg - Dpr | Arg - EtAsn | Arg - EtGly | Arg - gAbu | Arg - Gln | Arg - Glu |
| Asn - Dpr | Asn - EtAsn | Asn - EtGly | Asn - gAbu | Asn - Gln | Asn - Glu |
| Asp - Dpr | Asp - EtAsn | Asp - EtGly | Asp - gAbu | Asp - Gln | Asp - Glu |
| Atc - Dpr | Atc - EtAsn | Atc - EtGly | Atc - gAbu | Atc - Gln | Atc - Glu |
| Ava - Dpr | Ava - EtAsn | Ava - EtGly | Ava - gAbu | Ava - Gln | Ava - Glu |
| Aze - Dpr | Aze - EtAsn | Aze - EtGly | Aze - gAbu | Aze - Gln | Aze - Glu |
| bAad - Dpr | bAad - EtAsn | bAad - EtGly | bAad - gAbu | bAad - Gln | bAad - Glu |
| bAib - Dpr | bAib - EtAsn | bAib - EtGly | bAib - gAbu | bAib - Gln | bAib - Glu |
| bAla - Dpr | bAla - EtAsn | bAla - EtGly | bAla - gAbu | bAla - Gln | bAla - Glu |
| Cha - Dpr | Cha - EtAsn | Cha - EtGly | Cha - gAbu | Cha - Gln | Cha - Glu |
| Cpg - Dpr | Cpg - EtAsn | Cpg - EtGly | Cpg - gAbu | Cpg - Gln | Cpg - Glu |
| Cpp - Dpr | Cpp - EtAsn | Cpp - EtGly | Cpp - gAbu | Cpp - Gln | Cpp - Glu |
| cPzACAla - Dpr | cPzACAla - EtAsn | cPzACAla - EtGly | cPzACAla - gAbu | cPzACAla - Gln | cPzACAla - Glu |
| Cys - Dpr | Cys - EtAsn | Cys - EtGly | Cys - gAbu | Cys - Gln | Cys - Glu |
| Dap - Dpr | Dap - EtAsn | Dap - EtGly | Dap - gAbu | Dap - Gln | Dap - Glu |
| Dbf - Dpr | Dbf - EtAsn | Dbf - EtGly | Dbf - gAbu | Dbf - Gln | Dbf - Glu |
| Dbu - Dpr | Dbu - EtAsn | Dbu - EtGly | Dbu - gAbu | Dbu - Gln | Dbu - Glu |
| Des - Dpr | Des - EtAsn | Des - EtGly | Des - gAbu | Des - Gln | Des - Glu |
| Dip - Dpr | Dip - EtAsn | Dip - EtGly | Dip - gAbu | Dip - Gln | Dip - Glu |
| Dph - Dpr | Dph - EtAsn | Dph - EtGly | Dph - gAbu | Dph - Gln | Dph - Glu |
| Dpm - Dpr | Dpm - EtAsn | Dpm - EtGly | Dpm - gAbu | Dpm - Gln | Dpm - Glu |
| Dpr - Dpr | Dpr - EtAsn | Dpr - EtGly | Dpr - gAbu | Dpr - Gln | Dpr - Glu |
| EtAsn - Dpr | EtAsn - EtAsn | EtAsn - EtGly | EtAsn - gAbu | EtAsn - Gln | EtAsn - Glu |
| EtGly - Dpr | EtGly - EtAsn | EtGly - EtGly | EtGly - gAbu | EtGly - Gln | EtGly - Glu |
| gAbu - Dpr | gAbu - EtAsn | gAbu - EtGly | gAbu - gAbu | gAbu - Gln | gAbu - Glu |
| Gln - Dpr | Gln - EtAsn | Gln - EtGly | Gln - gAbu | Gln - Gln | Gln - Glu |
| Glu - Dpr | Glu - EtAsn | Glu - EtGly | Glu - gAbu | Glu - Gln | Glu - Glu |
| Gly - Dpr | Gly - EtAsn | Gly - EtGly | Gly - gAbu | Gly - Gln | Gly - Glu |
| Gly(Ph) - Dpr | Gly(Ph) - EtAsn | Gly(Ph) - EtGly | Gly(Ph) - gAbu | Gly(Ph) - Gln | Gly(Ph) - Glu |
| Har - Dpr | Har - EtAsn | Har - EtGly | Har - gAbu | Har - Gln | Har - Glu |
| Hcy - Dpr | Hcy - EtAsn | Hcy - EtGly | Hcy - gAbu | Hcy - Gln | Hcy - Glu |
| Hib - Dpr | Hib - EtAsn | Hib - EtGly | Hib - gAbu | Hib - Gln | Hib - Glu |
| His - Dpr | His - EtAsn | His - EtGly | His - gAbu | His - Gln | His - Glu |
| Hse - Dpr | Hse - EtAsn | Hse - EtGly | Hse - gAbu | Hse - Gln | Hse - Glu |
| Hyl - Dpr | Hyl - EtAsn | Hyl - EtGly | Hyl - gAbu | Hyl - Gln | Hyl - Glu |
| Hyp - Dpr | Hyp - EtAsn | Hyp - EtGly | Hyp - gAbu | Hyp - Gln | Hyp - Glu |
| Ide - Dpr | Ide - EtAsn | Ide - EtGly | Ide - gAbu | Ide - Gln | Ide - Glu |
| Ile - Dpr | Ile - EtAsn | Ile - EtGly | Ile - gAbu | Ile - Gln | Ile - Glu |
| Iva - Dpr | Iva - EtAsn | Iva - EtGly | Iva - gAbu | Iva - Gln | Iva - Glu |
| Leu - Dpr | Leu - EtAsn | Leu - EtGly | Leu - gAbu | Leu - Gln | Leu - Glu |
| Lys - Dpr | Lys - EtAsn | Lys - EtGly | Lys - gAbu | Lys - Gln | Lys - Glu |
| MeGly - Dpr | MeGly - EtAsn | MeGly - EtGly | MeGly - gAbu | MeGly - Gln | MeGly - Glu |
| MeIle - Dpr | MeIle - EtAsn | MeIle - EtGly | MeIle - gAbu | MeIle - Gln | MeIle - Glu |
| MeLys - Dpr | MeLys - EtAsn | MeLys - EtGly | MeLys - gAbu | MeLys - Gln | MeLys - Glu |
| Met - Dpr | Met - EtAsn | Met - EtGly | Met - gAbu | Met - Gln | Met - Glu |
| Met (O) - Dpr | Met (O) - EtAsn | Met (O) - EtGly | Met (O) - gAbu | Met (O) - Gln | Met (O) - Glu |
| Met (S—Me) - | Met (S—Me) - | Met (S—Me) - | Met (S—Me) - | Met (S—Me) - | Met (S—Me) - |

TABLE 5-continued

Illustrative combinations for $X^2 - X^3$ and/or $X^3 - X^4$.

| I-P | P-D | P-F | F-H | V-A | A-G |
|---|---|---|---|---|---|
| Dpr | EtAsn | EtGly | gAbu | Gln | Glu |
| MeVal - Dpr | MeVal - EtAsn | MeVal - EtGly | MeVal - gAbu | MeVal - Gln | MeVal - Glu |
| Mpt - Dpr | Mpt - EtAsn | Mpt - EtGly | Mpt - gAbu | Mpt - Gln | Mpt - Glu |
| Nap - Dpr | Nap - EtAsn | Nap - EtGly | Nap - gAbu | Nap - Gln | Nap - Glu |
| Nle - Dpr | Nle - EtAsn | Nle - EtGly | Nle - gAbu | Nle - Gln | Nle - Glu |
| Nva - Dpr | Nva - EtAsn | Nva - EtGly | Nva - gAbu | Nva - Gln | Nva - Glu |
| Oic - Dpr | Oic - EtAsn | Oic - EtGly | Oic - gAbu | Oic - Gln | Oic - Glu |
| Opt - Dpr | Opt - EtAsn | Opt - EtGly | Opt - gAbu | Opt - Gln | Opt - Glu |
| Orn - Dpr | Orn - EtAsn | Orn - EtGly | Orn - gAbu | Orn - Gln | Orn - Glu |
| Pen - Dpr | Pen - EtAsn | Pen - EtGly | Pen - gAbu | Pen - Gln | Pen - Glu |
| Phe - Dpr | Phe - EtAsn | Phe - EtGly | Phe - gAbu | Phe - Gln | Phe - Glu |
| Phg - Dpr | Phg - EtAsn | Phg - EtGly | Phg - gAbu | Phg - Gln | Phg - Glu |
| Pip - Dpr | Pip - EtAsn | Pip - EtGly | Pip - gAbu | Pip - Gln | Pip - Glu |
| Pmp - Dpr | Pmp - EtAsn | Pmp - EtGly | Pmp - gAbu | Pmp - Gln | Pmp - Glu |
| Pro - Dpr | Pro - EtAsn | Pro - EtGly | Pro - gAbu | Pro - Gln | Pro - Glu |
| Qal - Dpr | Qal - EtAsn | Qal - EtGly | Qal - gAbu | Qal - Gln | Qal - Glu |
| Qua - Dpr | Qua - EtAsn | Qua - EtGly | Qua - gAbu | Qua - Gln | Qua - Glu |
| Sar - Dpr | Sar - EtAsn | Sar - EtGly | Sar - gAbu | Sar - Gln | Sar - Glu |
| Ser - Dpr | Ser - EtAsn | Ser - EtGly | Ser - gAbu | Ser - Gln | Ser - Glu |
| Thi - Dpr | Thi - EtAsn | Thi - EtGly | Thi - gAbu | Thi - Gln | Thi - Glu |
| Thr - Dpr | Thr - EtAsn | Thr - EtGly | Thr - gAbu | Thr - Gln | Thr - Glu |
| Tic - Dpr | Tic - EtAsn | Tic - EtGly | Tic - gAbu | Tic - Gln | Tic - Glu |
| Trp - Dpr | Trp - EtAsn | Trp - EtGly | Trp - gAbu | Trp - Gln | Trp - Glu |
| Tyr - Dpr | Tyr - EtAsn | Tyr - EtGly | Tyr - gAbu | Tyr - Gln | Tyr - Glu |
| Val - Dpr | Val - EtAsn | Val - EtGly | Val - gAbu | Val - Gln | Val - Glu |
| βAla - Dpr | βAla - EtAsn | βAla - EtGly | βAla - gAbu | βAla - Gln | βAla - Glu |
| D-TIC - Gly | D-TIC - Gly(Ph) | D-TIC - Har | D-TIC - Hcy | D-TIC - Hib | D-TIC - His |
| GABA - Gly | GABA - Gly(Ph) | GABA - Har | GABA - Hcy | GABA - Hib | GABA - His |
| EACA - Gly | EACA - Gly(Ph) | EACA - Har | EACA - Hcy | EACA - Hib | EACA - His |
| K[TFA] - Gly | K[TFA] - Gly(Ph) | K[TFA] - Har | K[TFA] - Hcy | K[TFA] - Hib | K[TFA] - His |
| 1-Nal - Gly | 1 - Nal - Gly(Ph) | 1-Nal - Har | 1-Nal - Hcy | 1-Nal - Hib | 1-Nal - His |
| 2-Nal - Gly | 2-Nal - Gly(Ph) | 2-Nal - Har | 2-Nal - Hcy | 2-Nal - Hib | 2-Nal - His |
| 3Hyp - Gly | 3Hyp - Gly(Ph) | 3Hyp - Har | 3Hyp - Hcy | 3Hyp - Hib | 3Hyp - His |
| 3-Pal - Gly | 3-Pal - Gly(Ph) | 3-Pal - Har | 3-Pal - Hcy | 3-Pal - Hib | 3-Pal - His |
| 4Abu - Gly | 4Abu - Gly(Ph) | 4Abu - Har | 4Abu - Hcy | 4Abu - Hib | 4Abu - His |
| 4Hyp - Gly | 4Hyp - Gly(Ph) | 4Hyp - Har | 4Hyp - Hcy | 4Hyp - Hib | 4Hyp - His |
| A2bu - Gly | A2bu - Gly(Ph) | A2bu - Har | A2bu - Hcy | A2bu - Hib | A2bu - His |
| A2pr - Gly | A2pr - Gly(Ph) | A2pr - Har | A2pr - Hcy | A2pr - Hib | A2pr - His |
| Aad - Gly | Aad - Gly(Ph) | Aad - Har | Aad - Hcy | Aad - Hib | Aad - His |
| aAhx - Gly | aAhx - Gly(Ph) | aAhx - Har | aAhx - Hcy | aAhx - Hib | aAhx - His |
| Abo - Gly | Abo - Gly(Ph) | Abo - Har | Abo - Hcy | Abo - Hib | Abo - His |
| Abu - Gly | Abu - Gly(Ph) | Abu - Har | Abu - Hcy | Abu - Hib | Abu - His |
| ACCA - Gly | ACCA - Gly(Ph) | ACCA - Har | ACCA - Hcy | ACCA - Hib | ACCA - His |
| Acp - Gly | Acp - Gly(Ph) | Acp - Har | Acp - Hcy | Acp - Hib | Acp - His |
| Ahe - Gly | Ahe - Gly(Ph) | Ahe - Har | Ahe - Hcy | Ahe - Hib | Ahe - His |
| Ahx - Gly | Ahx - Gly(Ph) | Ahx - Har | Ahx - Hcy | Ahx - Hib | Ahx - His |
| aHyl - Gly | aHyl - Gly(Ph) | aHyl - Har | aHyl - Hcy | aHyl - Hib | aHyl - His |
| Aib - Gly | Aib - Gly(Ph) | Aib - Har | Aib - Hcy | Aib - Hib | Aib - His |
| Aib - Gly | Aib - Gly(Ph) | Aib - Har | Aib - Hcy | Aib - Hib | Aib - His |
| Aic - Gly | Aic - Gly(Ph) | Aic - Har | Aic - Hcy | Aic - Hib | Aic - His |
| aIle - Gly | aIle - Gly(Ph) | aIle - Har | aIle - Hcy | aIle - Hib | aIle - His |
| Ala - Gly | Ala - Gly(Ph) | Ala - Har | Ala - Hcy | Ala - Hib | Ala - His |
| Apm - Gly | Apm - Gly(Ph) | Apm - Har | Apm - Hcy | Apm - Hib | Apm - His |
| Arg - Gly | Arg - Gly(Ph) | Arg - Har | Arg - Hcy | Arg - Hib | Arg - His |
| Asn - Gly | Asn - Gly(Ph) | Asn - Har | Asn - Hcy | Asn - Hib | Asn - His |
| Asp - Gly | Asp - Gly(Ph) | Asp - Har | Asp - Hcy | Asp - Hib | Asp - His |
| Atc - Gly | Atc - Gly(Ph) | Atc - Har | Atc - Hcy | Atc - Hib | Atc - His |
| Ava - Gly | Ava - Gly(Ph) | Ava - Har | Ava - Hcy | Ava - Hib | Ava - His |
| Aze - Gly | Aze - Gly(Ph) | Aze - Har | Aze - Hcy | Aze - Hib | Aze - His |
| bAad - Gly | bAad - Gly(Ph) | bAad - Har | bAad - Hcy | bAad - Hib | bAad - His |
| bAib - Gly | bAib - Gly(Ph) | bAib - Har | bAib - Hcy | bAib - Hib | bAib - His |
| bAla - Gly | bAla - Gly(Ph) | bAla - Har | bAla - Hcy | bAla - Hib | bAla - His |
| Cha - Gly | Cha - Gly(Ph) | Cha - Har | Cha - Hcy | Cha - Hib | Cha - His |
| Cpg - Gly | Cpg - Gly(Ph) | Cpg - Har | Cpg - Hcy | Cpg - Hib | Cpg - His |
| Cpp - Gly | Cpp - Gly(Ph) | Cpp - Har | Cpp - Hcy | Cpp - Hib | Cpp - His |
| cPzACAla - Gly | cPzACAla - Gly(Ph) | cPzACAla - Har | cPzACAla - Hcy | cPzACAla - Hib | cPzACAla - His |
| Cys - Gly | Cys - Gly(Ph) | Cys - Har | Cys - Hcy | Cys - Hib | Cys - His |
| Dap - Gly | Dap - Gly(Ph) | Dap - Har | Dap - Hcy | Dap - Hib | Dap - His |
| Dbf - Gly | Dbf - Gly(Ph) | Dbf - Har | Dbf - Hcy | Dbf - Hib | Dbf - His |
| Dbu - Gly | Dbu - Gly(Ph) | Dbu - Har | Dbu - Hcy | Dbu - Hib | Dbu - His |
| Des - Gly | Des - Gly(Ph) | Des - Har | Des - Hcy | Des - Hib | Des - His |
| Dip - Gly | Dip - Gly(Ph) | Dip - Har | Dip - Hcy | Dip - Hib | Dip - His |
| Dph - Gly | Dph - Gly(Ph) | Dph - Har | Dph - Hcy | Dph - Hib | Dph - His |
| Dpm - Gly | Dpm - Gly(Ph) | Dpm - Har | Dpm - Hcy | Dpm - Hib | Dpm - His |
| Dpr - Gly | Dpr - Gly(Ph) | Dpr - Har | Dpr - Hcy | Dpr - Hib | Dpr - His |
| EtAsn - Gly | EtAsn - Gly(Ph) | EtAsn - Har | EtAsn - Hcy | EtAsn - Hib | EtAsn - His |

TABLE 5-continued

Illustrative combinations for $X^2 - X^3$ and/or $X^3 - X^4$.

| I-P | P-D | P-F | F-H | V-A | A-G |
|---|---|---|---|---|---|
| EtGly - Gly | EtGly - Gly(Ph) | EtGly - Har | EtGly - Hcy | EtGly - Hib | EtGly - His |
| gAbu - Gly | gAbu - Gly(Ph) | gAbu - Har | gAbu - Hcy | gAbu - Hib | gAbu - His |
| Gln - Gly | Gln - Gly(Ph) | Gln - Har | Gln - Hcy | Gln - Hib | Gln - His |
| Glu - Gly | Glu - Gly(Ph) | Glu - Har | Glu - Hcy | Glu - Hib | Glu - His |
| Gly - Gly | Gly - Gly(Ph) | Gly - Har | Gly - Hcy | Gly - Hib | Gly - His |
| Gly(Ph) - Gly | Gly(Ph) - Gly(Ph) | Gly(Ph) - Har | Gly(Ph) - Hcy | Gly(Ph) - Hib | Gly(Ph) - His |
| Har - Gly | Har - Gly(Ph) | Har - Har | Har - Hcy | Har - Hib | Har - His |
| Hcy - Gly | Hcy - Gly(Ph) | Hcy - Har | Hcy - Hcy | Hcy - Hib | Hcy - His |
| Hib - Gly | Hib - Gly(Ph) | Hib - Har | Hib - Hcy | Hib - Hib | Hib - His |
| His - Gly | His - Gly(Ph) | His - Har | His - Hcy | His - Hib | His - His |
| Hse - Gly | Hse - Gly(Ph) | Hse - Har | Hse - Hcy | Hse - Hib | Hse - His |
| Hyl - Gly | Hyl - Gly(Ph) | Hyl - Har | Hyl - Hcy | Hyl - Hib | Hyl - His |
| Hyp - Gly | Hyp - Gly(Ph) | Hyp - Har | Hyp - Hcy | Hyp - Hib | Hyp - His |
| Ide - Gly | Ide - Gly(Ph) | Ide - Har | Ide - Hcy | Ide - Hib | Ide - His |
| Ile - Gly | Ile - Gly(Ph) | Ile - Har | Ile - Hcy | Ile - Hib | Ile - His |
| Iva - Gly | Iva - Gly(Ph) | Iva - Har | Iva - Hcy | Iva - Hib | Iva - His |
| Leu - Gly | Leu - Gly(Ph) | Leu - Har | Leu - Hcy | Leu - Hib | Leu - His |
| Lys - Gly | Lys - Gly(Ph) | Lys - Har | Lys - Hcy | Lys - Hib | Lys - His |
| MeGly - Gly | MeGly - Gly(Ph) | MeGly - Har | MeGly - Hcy | MeGly - Hib | MeGly - His |
| MeIle - Gly | MeIle - Gly(Ph) | MeIle - Har | MeIle - Hcy | MeIle - Hib | MeIle - His |
| MeLys - Gly | MeLys - Gly(Ph) | MeLys - Har | MeLys - Hcy | MeLys - Hib | MeLys - His |
| Met - Gly | Met - Gly(Ph) | Met - Har | Met - Hcy | Met - Hib | Met - His |
| Met (O) - Gly | Met (O) - Gly(Ph) | Met (O) - Har | Met (O) - Hcy | Met (O) - Hib | Met (O) - His |
| Met (S—Me) - Gly | Met (S—Me) - Gly(Ph) | Met (S—Me) - Har | Met (S—Me) - Iley | Met (S—Me) - Hib | Met (S—Me) - His |
| MeVal - Gly | MeVal - Gly(Ph) | MeVal - Har | MeVal - Hcy | MeVal - Hib | MeVal - His |
| Mpt - Gly | Mpt - Gly(Ph) | Mpt - Har | Mpt - Hcy | Mpt - Hib | Mpt - His |
| Nap - Gly | Nap - Gly(Ph) | Nap - Har | Nap - Hcy | Nap - Hib | Nap - His |
| Nle - Gly | Nle - Gly(Ph) | Nle - Har | Nle - Hcy | Nle - Hib | Nle - His |
| Nva - Gly | Nva - Gly(Ph) | Nva - Har | Nva - Hcy | Nva - Hib | Nva - His |
| Oic - Gly | Oic - Gly(Ph) | Oic - Har | Oic - Hcy | Oic - Hib | Oic - His |
| Opt - Gly | Opt - Gly(Ph) | Opt - Har | Opt - Hcy | Opt - Hib | Opt - His |
| Orn - Gly | Orn - Gly(Ph) | Orn - Har | Orn - Hcy | Orn - Hib | Orn - His |
| Pen - Gly | Pen - Gly(Ph) | Pen - Har | Pen - Hcy | Pen - Hib | Pen - His |
| Phe - Gly | Phe - Gly(Ph) | Phe - Har | Phe - Hcy | Phe - Hib | Phe - His |
| Phg - Gly | Phg - Gly(Ph) | Phg - Har | Phg - Hcy | Phg - Hib | Phg - His |
| Pip - Gly | Pip - Gly(Ph) | Pip - Har | Pip - Hcy | Pip - Hib | Pip - His |
| Pmp - Gly | Pmp - Gly(Ph) | Pmp - Har | Pmp - Hcy | Pmp - Hib | Pmp - His |
| Pro - Gly | Pro - Gly(Ph) | Pro - Har | Pro - Hcy | Pro - Hib | Pro - His |
| Qal - Gly | Qal - Gly(Ph) | Qal - Har | Qal - Hcy | Qal - Hib | Qal - His |
| Qua - Gly | Qua - Gly(Ph) | Qua - Har | Qua - Hcy | Qua - Hib | Qua - His |
| Sar - Gly | Sar - Gly(Ph) | Sar - Har | Sar - Hcy | Sar - Hib | Sar - His |
| Ser - Gly | Ser - Gly(Ph) | Ser - Har | Ser - Hcy | Ser - Hib | Ser - His |
| Thi - Gly | Thi - Gly(Ph) | Thi - Har | Thi - Hcy | Thi - Hib | Thi - His |
| Thr - Gly | Thr - Gly(Ph) | Thr - Har | Thr - Hcy | Thr - Hib | Thr - His |
| Tic - Gly | Tic - Gly(Ph) | Tic - Har | Tic - Hcy | Tic - Hib | Tic - His |
| Trp - Gly | Trp - Gly(Ph) | Trp - Har | Trp - Hcy | Trp - Hib | Trp - His |
| Tyr - Gly | Tyr - Gly(Ph) | Tyr - Har | Tyr - Hcy | Tyr - Hib | Tyr - His |
| Val - Gly | Val - Gly(Ph) | Val - Har | Val - Hcy | Val - Hib | Val - His |
| βAla - Gly | βAla - Gly(Ph) | βAla - Har | βAla - Hcy | βAla - Hib | βAla - His |
| D-TIC - Hse | D-TIC - Hyl | D-TIC - Hyp | D-TIC - Ide | D-TIC - Ile | D-TIC - Iva |
| GABA - Hse | GABA - Hyl | GABA - Hyp | GABA - Ide | GABA - Ile | GABA - Iva |
| EACA - Hse | EACA - Hyl | EACA - Hyp | EACA - Ide | EACA - Ile | EACA - Iva |
| K[TFA] - Hse | K[TFA] - Hyl | K[TFA] - Hyp | K[TFA] - Ide | K[TFA] - Ile | K[TFA] - Iva |
| 1-Nal - Hse | 1-Nal - Hyl | 1-Nal - Hyp | 1-Nal - Ide | 1-Nal - Ile | 1-Nal - Iva |
| 2-Nal - Hse | 2-Nal - Hyl | 2-Nal - Hyp | 2-Nal - Ide | 2-Nal - Ile | 2-Nal - Iva |
| 3Hyp - Hse | 3Hyp - Hyl | 3Hyp - Hyp | 3Hyp - Ide | 3Hyp - Ile | 3Hyp - Iva |
| 3-Pal - Hse | 3-Pal - Hyl | 3-Pal - Hyp | 3-Pal - Ide | 3-Pal - Ile | 3-Pal - Iva |
| 4Abu - Hse | 4Abu - Hyl | 4Abu - Hyp | 4Abu - Ide | 4Abu - Ile | 4Abu - Iva |
| 4Hyp - Hse | 4Hyp - Hyl | 4Hyp - Hyp | 4Hyp - Ide | 4Hyp - Ile | 4Hyp - Iva |
| A2bu - Hse | A2bu - Hyl | A2bu - Hyp | A2bu - Ide | A2bu - Ile | A2bu - Iva |
| A2pr - Hse | A2pr - Hyl | A2pr - Hyp | A2pr - Ide | A2pr - Ile | A2pr - Iva |
| Aad - Hse | Aad - Hyl | Aad - Hyp | Aad - Ide | Aad - Ile | Aad - Iva |
| aAhx - Hse | aAhx - Hyl | aAhx - Hyp | aAhx - Ide | aAhx - Ile | aAhx - Iva |
| Abo - Hse | Abo - Hyl | Abo - Hyp | Abo - Ide | Abo - Ile | Abo - Iva |
| Abu - Hse | Abu - Hyl | Abu - Hyp | Abu - Ide | Abu - Ile | Abu - Iva |
| ACCA - Hse | ACCA - Hyl | ACCA - Hyp | ACCA - Ide | ACCA - Ile | ACCA - Iva |
| Acp - Hse | Acp - Hyl | Acp - Hyp | Acp - Ide | Acp - Ile | Acp - Iva |
| Ahe - Hse | Ahe - Hyl | Ahe - Hyp | Ahe - Ide | Ahe - Ile | Ahe - Iva |
| Ahx - Hse | Ahx - Hyl | Ahx - Hyp | Ahx - Ide | Ahx - Ile | Ahx - Iva |
| aHyl - Hse | aHyl - Hyl | aHyl - Hyp | aHyl - Ide | aHyl - Ile | aHyl - Iva |
| Aib - Hse | Aib - Hyl | Aib - Hyp | Aib - Ide | Aib - Ile | Aib - Iva |
| Aib - Hse | Aib - Hyl | Aib - Hyp | Aib - Ide | Aib - Ile | Aib - Iva |
| Aic - Hse | Aic - Hyl | Aic - Hyp | Aic - Ide | Aic - Ile | Aic - Iva |
| aIle - Hse | aIle - Hyl | aIle - Hyp | aIle - Ide | aIle - Ile | aIle - Iva |
| Ala - Hse | Ala - Hyl | Ala - Hyp | Ala - Ide | Ala - Ile | Ala - Iva |

TABLE 5-continued

Illustrative combinations for $X^2 - X^3$ and/or $X^3 - X^4$.

| I-P | P-D | P-F | F-H | V-A | A-G |
|---|---|---|---|---|---|
| Apm - Hse | Apm - Hyl | Apm - Hyp | Apm - Ide | Apm - Ile | Apm - Iva |
| Arg - Hse | Arg - Hyl | Arg - Hyp | Arg - Ide | Arg - Ile | Arg - Iva |
| Asn - Hse | Asn - Hyl | Asn - Hyp | Asn - Ide | Asn - Ile | Asn - Iva |
| Asp - Hse | Asp - Hyl | Asp - Hyp | Asp - Ide | Asp - Ile | Asp - Iva |
| Atc - Hse | Atc - Hyl | Atc - Hyp | Atc - Ide | Atc - Ile | Atc - Iva |
| Ava - Hse | Ava - Hyl | Ava - Hyp | Ava - Ide | Ava - Ile | Ava - Iva |
| Aze - Hse | Aze - Hyl | Aze - Hyp | Aze - Ide | Aze - Ile | Aze - Iva |
| bAad - Hse | bAad - Hyl | bAad - Hyp | bAad - Ide | bAad - Ile | bAad - Iva |
| bAib - Hse | bAib - Hyl | bAib - Hyp | bAib - Ide | bAib - Ile | bAib - Iva |
| bAla - Hse | bAla - Hyl | bAla - Hyp | bAla - Ide | bAla - Ile | bAla - Iva |
| Cha - Hse | Cha - Hyl | Cha - Hyp | Cha - Ide | Cha - Ile | Cha - Iva |
| Cpg - Hse | Cpg - Hyl | Cpg - Hyp | Cpg - Ide | Cpg - Ile | Cpg - Iva |
| Cpp - Hse | Cpp - Hyl | Cpp - Hyp | Cpp - Ide | Cpp - Ile | Cpp - Iva |
| cPzACAla - Hse | cPzACAla - Hyl | cPzACAla - Hyp | cPzACAla - Ide | cPzACAla - Ile | cPzACAla - Iva |
| Cys - Hse | Cys - Hyl | Cys - Hyp | Cys - Ide | Cys - Ile | Cys - Iva |
| Dap - Hse | Dap - Hyl | Dap - Hyp | Dap - Ide | Dap - Ile | Dap - Iva |
| Dbf - Hse | Dbf - Hyl | Dbf - Hyp | Dbf - Ide | Dbf - Ile | Dbf - Iva |
| Dbu - Hse | Dbu - Hyl | Dbu - Hyp | Dbu - Ide | Dbu - Ile | Dbu - Iva |
| Des - Hse | Des - Hyl | Des - Hyp | Des - Ide | Des - Ile | Des - Iva |
| Dip - Hse | Dip - Hyl | Dip - Hyp | Dip - Ide | Dip - Ile | Dip - Iva |
| Dph - Hse | Dph - Hyl | Dph - Hyp | Dph - Ide | Dph - Ile | Dph - Iva |
| Dpm - Hse | Dpm - Hyl | Dpm - Hyp | Dpm - Ide | Dpm - Ile | Dpm - Iva |
| Dpr - Hse | Dpr - Hyl | Dpr - Hyp | Dpr - Ide | Dpr - Ile | Dpr - Iva |
| EtAsn - Hse | EtAsn - Hyl | EtAsn - Hyp | EtAsn - Ide | EtAsn - Ile | EtAsn - Iva |
| EtGly - Hse | EtGly - Hyl | EtGly - Hyp | EtGly - Ide | EtGly - Ile | EtGly - Iva |
| gAbu - Hse | gAbu - Hyl | gAbu - Hyp | gAbu - Ide | gAbu - Ile | gAbu - Iva |
| Gln - Hse | Gln - Hyl | Gln - Hyp | Gln - Ide | Gln - Ile | Gln - Iva |
| Glu - Hse | Glu - Hyl | Glu - Hyp | Glu - Ide | Glu - Ile | Glu - Iva |
| Gly - Hse | Gly - Hyl | Gly - Hyp | Gly - Ide | Gly - Ile | Gly - Iva |
| Gly(Ph) - Hse | Gly(Ph) - Hyl | Gly(Ph) - Hyp | Gly(Ph) - Ide | Gly(Ph) - Ile | Gly(Ph) - Iva |
| Har - Hse | Har - Hyl | Har - Hyp | Har - Ide | Har - Ile | Har - Iva |
| Hcy - Hse | Hcy - Hyl | Hcy - Hyp | Hcy - Ide | Hcy - Ile | Hcy - Iva |
| Hib - Hse | Hib - Hyl | Hib - Hyp | Hib - Ide | Hib - Ile | Hib - Iva |
| His - Hse | His - Hyl | His - Hyp | His - Ide | His - Ile | His - Iva |
| Hse - Hse | Hse - Hyl | Hse - Hyp | Hse - Ide | Hse - Ile | Hse - Iva |
| Hyl - Hse | Hyl - Hyl | Hyl - Hyp | Hyl - Ide | Hyl - Ile | Hyl - Iva |
| Hyp - Hse | Hyp - Hyl | Hyp - Hyp | Hyp - Ide | Hyp - Ile | Hyp - Iva |
| Ide - Hse | Ide - Hyl | Ide - Hyp | Ide - Ide | Ide - Ile | Ide - Iva |
| Ile - Hse | Ile - Hyl | Ile - Hyp | Ile - Ide | Ile - Ile | Ile - Iva |
| Iva - Hse | Iva - Hyl | Iva - Hyp | Iva - Ide | Iva - Ile | Iva - Iva |
| Leu - Hse | Leu - Hyl | Leu - Hyp | Leu - Ide | Leu - Ile | Leu - Iva |
| Lys - Hse | Lys - Hyl | Lys - Hyp | Lys - Ide | Lys - Ile | Lys - Iva |
| MeGly - Hse | MeGly - Hyl | MeGly - Hyp | MeGly - Ide | MeGly - Ile | MeGly - Iva |
| MeIle - Hse | MeIle - Hyl | MeIle - Hyp | MeIle - Ide | MeIle - Ile | MeIle - Iva |
| MeLys - Hse | MeLys - Hyl | MeLys - Hyp | MeLys - Ide | MeLys - Ile | MeLys - Iva |
| Met - Hse | Met - Hyl | Met - Hyp | Met - Ide | Met - Ile | Met - Iva |
| Met (O) - Hse | Met (O) - Hyl | Met (O) - Hyp | Met (O) - Ide | Met (O) - Ile | Met (O) - Iva |
| Met (S—Me) - Hse | Met (S—Me) - Hyl | Met (S—Me) - Hyp | Met (S—Me) - Ide | Met (S—Me) - Ile | Met (S—Me) - Iva |
| MeVal - Hse | MeVal - Hyl | MeVal - Hyp | MeVal - Ide | MeVal - Ile | MeVal - Iva |
| Mpt - Hse | Mpt - Hyl | Mpt - Hyp | Mpt - Ide | Mpt - Ile | Mpt - Iva |
| Nap - Hse | Nap - Hyl | Nap - Hyp | Nap - Ide | Nap - Ile | Nap - Iva |
| Nle - Hse | Nle - Hyl | Nle - Hyp | Nle - Ide | Nle - Ile | Nle - Iva |
| Nva - Hse | Nva - Hyl | Nva - Hyp | Nva - Ide | Nva - Ile | Nva - Iva |
| Oic - Hse | Oic - Hyl | Oic - Hyp | Oic - Ide | Oic - Ile | Oic - Iva |
| Opt - Hse | Opt - Hyl | Opt - Hyp | Opt - Ide | Opt - Ile | Opt - Iva |
| Orn - Hse | Orn - Hyl | Orn - Hyp | Orn - Ide | Orn - Ile | Orn - Iva |
| Pen - Hse | Pen - Hyl | Pen - Hyp | Pen - Ide | Pen - Ile | Pen - Iva |
| Phe - Hse | Phe - Hyl | Phe - Hyp | Phe - Ide | Phe - Ile | Phe - Iva |
| Phg - Hse | Phg - Hyl | Phg - Hyp | Phg - Ide | Phg - Ile | Phg - Iva |
| Pip - Hse | Pip - Hyl | Pip - Hyp | Pip - Ide | Pip - Ile | Pip - Iva |
| Pmp - Hse | Pmp - Hyl | Pmp - Hyp | Pmp - Ide | Pmp - Ile | Pmp - Iva |
| Pro - Hse | Pro - Hyl | Pro - Hyp | Pro - Ide | Pro - Ile | Pro - Iva |
| Qal - Hse | Qal - Hyl | Qal - Hyp | Qal - Ide | Qal - Ile | Qal - Iva |
| Qua - Hse | Qua - Hyl | Qua - Hyp | Qua - Ide | Qua - Ile | Qua - Iva |
| Sar - Hse | Sar - Hyl | Sar - Hyp | Sar - Ide | Sar - Ile | Sar - Iva |
| Ser - Hse | Ser - Hyl | Ser - Hyp | Ser - Ide | Ser - Ile | Ser - Iva |
| Thi - Hse | Thi - Hyl | Thi - Hyp | Thi - Ide | Thi - Ile | Thi - Iva |
| Thr - Hse | Thr - Hyl | Thr - Hyp | Thr - Ide | Thr - Ile | Thr - Iva |
| Tic - Hse | Tic - Hyl | Tic - Hyp | Tic - Ide | Tic - Ile | Tic - Iva |
| Trp - Hse | Trp - Hyl | Trp - Hyp | Trp - Ide | Trp - Ile | Trp - Iva |
| Tyr - Hse | Tyr - Hyl | Tyr - Hyp | Tyr - Ide | Tyr - Ile | Tyr - Iva |
| Val - Hse | Val - Hyl | Val - Hyp | Val - Ide | Val - Ile | Val - Iva |
| βAla - Hse | βAla - Hyl | βAla - Hyp | βAla - Ide | βAla - Ile | βAla - Iva |
| D-TIC - Leu | D-TIC - Lys | D-TIC - MeGly | D-TIC - MeIle | D-TIC - MeLys | D-TIC - Met |
| GABA - Leu | GABA - Lys | GABA - MeGly | GABA - MeIle | GABA - MeLys | GABA - Met |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| EACA - Leu | EACA - Lys | EACA - MeGly | EACA - MeIle | EACA - MeLys | EACA - Met |
| K[TFA] - Leu | K[TFA] - Lys | K[TFA] - MeGly | K[TFA] - MeIle | K[TFA] - MeLys | K[TFA] - Met |
| 1-Nal - Leu | 1-Nal - Lys | 1-Nal - MeGly | 1-Nal - MeIle | 1-Nal - MeLys | 1-Nal - Met |
| 2-Nal - Leu | 2-Nal - Lys | 2-Nal - MeGly | 2-Nal - MeIle | 2-Nal - MeLys | 2-Nal - Met |
| 3Hyp - Leu | 3Hyp - Lys | 3Hyp - MeGly | 3Hyp - MeIle | 3Hyp - MeLys | 3Hyp - Met |
| 3-Pal - Leu | 3-Pal - Lys | 3-Pal - MeGly | 3-Pal - MeIle | 3-Pal - MeLys | 3-Pal - Met |
| 4Abu - Leu | 4Abu - Lys | 4Abu - MeGly | 4Abu - MeIle | 4Abu - MeLys | 4Abu - Met |
| 4Hyp - Leu | 4Hyp - Lys | 4Hyp - MeGly | 4Hyp - MeIle | 4Hyp - MeLys | 4Hyp - Met |
| A2bu - Leu | A2bu - Lys | A2bu - MeGly | A2bu - MeIle | A2bu - MeLys | A2bu - Met |
| A2pr - Leu | A2pr - Lys | A2pr - MeGly | A2pr - MeIle | A2pr - MeLys | A2pr - Met |
| Aad - Leu | Aad - Lys | Aad - MeGly | Aad - MeIle | Aad - MeLys | Aad - Met |
| aAhx - Leu | aAhx - Lys | aAhx - MeGly | aAhx - MeIle | aAhx - MeLys | aAhx - Met |
| Abo - Leu | Abo - Lys | Abo - MeGly | Abo - MeIle | Abo - MeLys | Abo - Met |
| Abu - Leu | Abu - Lys | Abu - MeGly | Abu - MeIle | Abu - MeLys | Abu - Met |
| ACCA - Leu | ACCA - Lys | ACCA - MeGly | ACCA - MeIle | ACCA - MeLys | ACCA - Met |
| Acp - Leu | Acp - Lys | Acp - MeGly | Acp - MeIle | Acp - MeLys | Acp - Met |
| Ahe - Leu | Ahe - Lys | Ahe - MeGly | Ahe - MeIle | Ahe - MeLys | Ahe - Met |
| Ahx - Leu | Ahx - Lys | Ahx - MeGly | Ahx - MeIle | Ahx - MeLys | Ahx - Met |
| aHyl - Leu | aHyl - Lys | aHyl - MeGly | aHyl - MeIle | aHyl - MeLys | aHyl - Met |
| Aib - Leu | Aib - Lys | Aib - MeGly | Aib - MeIle | Aib - MeLys | Aib - Met |
| Aib - Leu | Aib - Lys | Aib - MeGly | Aib - MeIle | Aib - MeLys | Aib - Met |
| Aic - Leu | Aic - Lys | Aic - MeGly | Aic - MeIle | Aic - MeLys | Aic - Met |
| aIle - Leu | aIle - Lys | aIle - MeGly | aIle - MeIle | aIle - MeLys | aIle - Met |
| Ala - Leu | Ala - Lys | Ala - MeGly | Ala - MeIle | Ala - MeLys | Ala - Met |
| Apm - Leu | Apm - Lys | Apm - MeGly | Apm - MeIle | Apm - MeLys | Apm - Met |
| Arg - Leu | Arg - Lys | Arg - MeGly | Arg - MeIle | Arg - MeLys | Arg - Met |
| Asn - Leu | Asn - Lys | Asn - MeGly | Asn - MeIle | Asn - MeLys | Asn - Met |
| Asp - Leu | Asp - Lys | Asp - MeGly | Asp - MeIle | Asp - MeLys | Asp - Met |
| Atc - Leu | Atc - Lys | Atc - MeGly | Atc - MeIle | Atc - MeLys | Atc - Met |
| Ava - Leu | Ava - Lys | Ava - MeGly | Ava - MeIle | Ava - MeLys | Ava - Met |
| Aze - Leu | Aze - Lys | Aze - MeGly | Aze - MeIle | Aze - MeLys | Aze - Met |
| bAad - Leu | bAad - Lys | bAad - MeGly | bAad - MeIle | bAad - MeLys | bAad - Met |
| bAib - Leu | bAib - Lys | bAib - MeGly | bAib - MeIle | bAib - MeLys | bAib - Met |
| bAla - Leu | bAla - Lys | bAla - MeGly | bAla - MeIle | bAla - MeLys | bAla - Met |
| Cha - Leu | Cha - Lys | Cha - MeGly | Cha - MeIle | Cha - MeLys | Cha - Met |
| Cpg - Leu | Cpg - Lys | Cpg - MeGly | Cpg - MeIle | Cpg - MeLys | Cpg - Met |
| Cpp - Leu | Cpp - Lys | Cpp - MeGly | Cpp - MeIle | Cpp - MeLys | Cpp - Met |
| cPzACAla - Leu | cPzACAla - Lys | cPzACAla - MeGly | cPzACAla - MeIle | cPzACAla - MeLys | cPzACAla - Met |
| Cys - Leu | Cys - Lys | Cys - MeGly | Cys - MeIle | Cys - MeLys | Cys - Met |
| Dap - Leu | Dap - Lys | Dap - MeGly | Dap - MeIle | Dap - MeLys | Dap - Met |
| Dbf - Leu | Dbf - Lys | Dbf - MeGly | Dbf - MeIle | Dbf - MeLys | Dbf - Met |
| Dbu - Leu | Dbu - Lys | Dbu - MeGly | Dbu - MeIle | Dbu - MeLys | Dbu - Met |
| Des - Leu | Des - Lys | Des - MeGly | Des - MeIle | Des - MeLys | Des - Met |
| Dip - Leu | Dip - Lys | Dip - MeGly | Dip - MeIle | Dip - MeLys | Dip - Met |
| Dph - Leu | Dph - Lys | Dph - MeGly | Dph - MeIle | Dph - MeLys | Dph - Met |
| Dpm - Leu | Dpm - Lys | Dpm - MeGly | Dpm - MeIle | Dpm - MeLys | Dpm - Met |
| Dpr - Leu | Dpr - Lys | Dpr - MeGly | Dpr - MeIle | Dpr - MeLys | Dpr - Met |
| EtAsn - Leu | EtAsn - Lys | EtAsn - MeGly | EtAsn - MeIle | EtAsn - MeLys | EtAsn - Met |
| EtGly - Leu | EtGly - Lys | EtGly - MeGly | EtGly - MeIle | EtGly - MeLys | EtGly - Met |
| gAbu - Leu | gAbu - Lys | gAbu - MeGly | gAbu - MeIle | gAbu - MeLys | gAbu - Met |
| Gln - Leu | Gln - Lys | Gln - MeGly | Gln - MeIle | Gln - MeLys | Gln - Met |
| Glu - Leu | Glu - Lys | Glu - MeGly | Glu - MeIle | Glu - MeLys | Glu - Met |
| Gly - Leu | Gly - Lys | Gly - MeGly | Gly - MeIle | Gly - MeLys | Gly - Met |
| Gly(Ph) - Leu | Gly(Ph) - Lys | Gly(Ph) - MeGly | Gly(Ph) - MeIle | Gly(Ph) - MeLys | Gly(Ph) - Met |
| Har - Leu | Har - Lys | Har - MeGly | Har - MeIle | Har - MeLys | Har - Met |
| Hcy - Leu | Hcy - Lys | Hcy - MeGly | Hcy - MeIle | Hcy - MeLys | Hcy - Met |
| Hib - Leu | Hib - Lys | Hib - MeGly | Hib - MeIle | Hib - MeLys | Hib - Met |
| His - Leu | His - Lys | His - MeGly | His - MeIle | His - MeLys | His - Met |
| Hse - Leu | Hse - Lys | Hse - MeGly | Hse - MeIle | Hse - MeLys | Hse - Met |
| Hyl - Leu | Hyl - Lys | Hyl - MeGly | Hyl - MeIle | Hyl - MeLys | Hyl - Met |
| Hyp - Leu | Hyp - Lys | Hyp - MeGly | Hyp - MeIle | Hyp - MeLys | Hyp - Met |
| Ide - Leu | Ide - Lys | Ide - MeGly | Ide - MeIle | Ide - MeLys | Ide - Met |
| Ile - Leu | Ile - Lys | Ile - MeGly | Ile - MeIle | Ile - MeLys | Ile - Met |
| Iva - Leu | Iva - Lys | Iva - MeGly | Iva - MeIle | Iva - MeLys | Iva - Met |
| Leu - Leu | Leu - Lys | Leu - MeGly | Leu - MeIle | Leu - MeLys | Leu - Met |
| Lys - Leu | Lys - Lys | Lys - MeGly | Lys - MeIle | Lys - MeLys | Lys - Met |
| MeGly - Leu | MeGly - Lys | MeGly - MeGly | MeGly - MeIle | MeGly - MeLys | MeGly - Met |
| MeIle - Leu | MeIle - Lys | MeIle - MeGly | MeIle - MeIle | MeIle - MeLys | MeIle - Met |
| MeLys - Leu | MeLys - Lys | MeLys - MeGly | MeLys - MeIle | MeLys - MeLys | MeLys - Met |
| Met - Leu | Met - Lys | Met - MeGly | Met - MeIle | Met - MeLys | Met - Met |
| Met (O) - Leu | Met (O) - Lys | Met (O) - MeGly | Met (O) - MeIle | Met (O) - MeLys | Met (O) - Met |
| Met (S—Me) - Leu | Met (S—Me) - Lys | Met (S—Me) - MeGly | Met (S—Me) - MeIle | Met (S—Me) - MeLys | Met (S—Me) - Met |
| MeVal - Leu | MeVal - Lys | MeVal - MeGly | MeVal - MeIle | MeVal - MeLys | MeVal - Met |
| Mpt - Leu | Mpt - Lys | Mpt - MeGly | Mpt - MeIle | Mpt - MeLys | Mpt - Met |
| Nap - Leu | Nap - Lys | Nap - MeGly | Nap - MeIle | Nap - MeLys | Nap - Met |

TABLE 5-continued

Illustrative combinations for $X^2 - X^3$ and/or $X^3 - X^4$.

| I-P | P-D | P-F | F-H | V-A | A-G |
|---|---|---|---|---|---|
| Nle - Leu | Nle - Lys | Nle - MeGly | Nle - MeIle | Nle - MeLys | Nle - Met |
| Nva - Leu | Nva - Lys | Nva - MeGly | Nva - MeIle | Nva - MeLys | Nva - Met |
| Oic - Leu | Oic - Lys | Oic - MeGly | Oic - MeIle | Oic - MeLys | Oic - Met |
| Opt - Leu | Opt - Lys | Opt - MeGly | Opt - MeIle | Opt - MeLys | Opt - Met |
| Orn - Leu | Orn - Lys | Orn - MeGly | Orn - MeIle | Orn - MeLys | Orn - Met |
| Pen - Leu | Pen - Lys | Pen - MeGly | Pen - MeIle | Pen - MeLys | Pen - Met |
| Phe - Leu | Phe - Lys | Phe - MeGly | Phe - MeIle | Phe - MeLys | Phe - Met |
| Phg - Leu | Phg - Lys | Phg - MeGly | Phg - MeIle | Phg - MeLys | Phg - Met |
| Pip - Leu | Pip - Lys | Pip - MeGly | Pip - MeIle | Pip - MeLys | Pip - Met |
| Pmp - Leu | Pmp - Lys | Pmp - MeGly | Pmp - MeIle | Pmp - MeLys | Pmp - Met |
| Pro - Leu | Pro - Lys | Pro - MeGly | Pro - MeIle | Pro - MeLys | Pro - Met |
| Qal - Leu | Qal - Lys | Qal - MeGly | Qal - MeIle | Qal - MeLys | Qal - Met |
| Qua - Leu | Qua - Lys | Qua - MeGly | Qua - MeIle | Qua - MeLys | Qua - Met |
| Sar - Leu | Sar - Lys | Sar - MeGly | Sar - MeIle | Sar - MeLys | Sar - Met |
| Ser - Leu | Ser - Lys | Ser - MeGly | Ser - MeIle | Ser - MeLys | Ser - Met |
| Thi - Leu | Thi - Lys | Thi - MeGly | Thi - MeIle | Thi - MeLys | Thi - Met |
| Thr - Leu | Thr - Lys | Thr - MeGly | Thr - MeIle | Thr - MeLys | Thr - Met |
| Tic - Leu | Tic - Lys | Tic - MeGly | Tic - MeIle | Tic - MeLys | Tic - Met |
| Trp - Leu | Trp - Lys | Trp - MeGly | Trp - MeIle | Trp - MeLys | Trp - Met |
| Tyr - Leu | Tyr - Lys | Tyr - MeGly | Tyr - MeIle | Tyr - MeLys | Tyr - Met |
| Val - Leu | Val - Lys | Val - MeGly | Val - MeIle | Val - MeLys | Val - Met |
| βAla - Leu | βAla - Lys | βAla - MeGly | βAla - MeIle | βAla - MeLys | βAla - Met |
| D-TIC - Met (O) | D-TIC - Met (S—Me) | D-TIC - MeVal | D-TIC - Mpt | D-TIC - Nap | D-TIC - Nle |
| GABA - Met (O) | GABA - Met (S—Me) | GABA - MeVal | GABA - Mpt | GABA - Nap | GABA - Nle |
| EACA - Met (O) | EACA - Met (S—Me) | EACA - MeVal | EACA - Mpt | EACA - Nap | EACA - Nle |
| K[TFA] - Met (O) | K[TFA] - Met (S—Me) | K[TFA] - MeVal | K[TFA] - Mpt | K[TFA] - Nap | K[TFA] - Nle |
| 1-Nal - Met(O) | 1-Nal - Met (S—Me) | 1-Nal - MeVal | 1-Nal - Mpt | 1-Nal - Nap | 1-Nal - Nle |
| 2-Nal - Met (O) | 2-Nal - Met (S—Me) | 2-Nal - MeVal | 2-Nal - Mpt | 2-Nal - Nap | 2-Nal - Nle |
| 3Hyp - Met (O) | 3Hyp - Met (S—Me) | 3Hyp - MeVal | 3Hyp - Mpt | 3Hyp - Nap | 3Hyp - Nle |
| 3-Pal - Met (O) | 3-Pal - Met (S—Me) | 3-Pal - MeVal | 3-Pal - Mpt | 3-Pal - Nap | 3-Pal - Nle |
| 4Abu - Met (O) | 4Abu - Met (S—Me) | 4Abu - MeVal | 4Abu - Mpt | 4Abu - Nap | 4Abu - Nle |
| 4Hyp - Met (O) | 4Hyp - Met (S—Me) | 4Hyp - MeVal | 4Hyp - Mpt | 4Hyp - Nap | 4Hyp - Nle |
| A2bu - Met (O) | A2bu - Met (S—Me) | A2bu - MeVal | A2bu - Mpt | A2bu - Nap | A2bu - Nle |
| A2pr - Met (O) | A2pr - Met (S—Me) | A2pr - MeVal | A2pr - Mpt | A2pr - Nap | A2pr - Nle |
| Aad - Met (O) | Aad - Met (S—Me) | Aad - MeVal | Aad - Mpt | Aad - Nap | Aad - Nle |
| aAhx - Met (O) | aAhx - Met (S—Me) | aAhx - MeVal | aAhx - Mpt | aAhx - Nap | aAhx - Nle |
| Abo - Met (O) | Abo - Met (S—Me) | Abo - MeVal | Abo - Mpt | Abo - Nap | Abo - Nle |
| Abu - Met (O) | Abu - Met (S—Me) | Abu - MeVal | Abu - Mpt | Abu - Nap | Abu - Nle |
| ACCA - Met (O) | ACCA - Met (S—Me) | ACCA - MeVal | ACCA - Mpt | ACCA - Nap | ACCA - Nle |
| Acp - Met (O) | Acp - Met (S—Me) | Acp - MeVal | Acp - Mpt | Acp - Nap | Acp - Nle |
| Ahe - Met (O) | Ahe - Met (S—Me) | Ahe - MeVal | Ahe - Mpt | Ahe - Nap | Ahe - Nle |
| Ahx - Met (O) | Ahx - Met (S—Me) | Ahx - MeVal | Ahx - Mpt | Ahx - Nap | Ahx - Nle |
| aHyl - Met (O) | aHyl - Met (S—Me) | aHyl - MeVal | aHyl - Mpt | aHyl - Nap | aHyl - Nle |
| Aib - Met (O) | Aib - Met (S—Me) | Aib - MeVal | Aib - Mpt | Aib - Nap | Aib - Nle |
| Aib - Met (O) | Aib - Met (S—Me) | Aib - MeVal | Aib - Mpt | Aib - Nap | Aib - Nle |
| Aic - Met (O) | Aic - Met (S—Me) | Aic - MeVal | Aic - Mpt | Aic - Nap | Aic - Nle |
| aIle - Met (O) | aIle - Met (S—Me) | aIle - MeVal | aIle - Mpt | aIle - Nap | aIle - Nle |
| Ala - Met (O) | Ala - Met (S—Me) | Ala - MeVal | Ala - Mpt | Ala - Nap | Ala - Nle |
| Apm - Met (O) | Apm - Met (S—Me) | Apm - MeVal | Apm - Mpt | Apm - Nap | Apm - Nle |
| Arg - Met (O) | Arg - Met (S—Me) | Arg - MeVal | Arg - Mpt | Arg - Nap | Arg - Nle |
| Asn - Met (O) | Asn - Met (S—Me) | Asn - MeVal | Asn - Mpt | Asn - Nap | Asn - Nle |
| Asp - Met (O) | Asp - Met (S—Me) | Asp - MeVal | Asp - Mpt | Asp - Nap | Asp - Nle |
| Atc - Met (O) | Atc - Met (S—Me) | Atc - MeVal | Atc - Mpt | Atc - Nap | Atc - Nle |
| Ava - Met (O) | Ava - Met (S—Me) | Ava - MeVal | Ava - Mpt | Ava - Nap | Ava - Nle |
| Aze - Met (O) | Aze - Met (S—Me) | Aze - MeVal | Aze - Mpt | Aze - Nap | Aze - Nle |
| bAad - Met (O) | bAad - Met (S—Me) | bAad - MeVal | bAad - Mpt | bAad - Nap | bAad - Nle |
| bAib - Met (O) | bAib - Met (S—Me) | bAib - MeVal | bAib - Mpt | bAib - Nap | bAib - Nle |
| bAla - Met (O) | bAla - Met (S—Me) | bAla - MeVal | bAla - Mpt | bAla - Nap | bAla - Nle |
| Cha - Met (O) | Cha - Met (S—Me) | Cha - MeVal | Cha - Mpt | Cha - Nap | Cha - Nle |
| Cpg - Met (O) | Cpg - Met (S—Me) | Cpg - MeVal | Cpg - Mpt | Cpg - Nap | Cpg - Nle |
| Cpp - Met (O) | Cpp - Met (S—Me) | Cpp - MeVal | Cpp - Mpt | Cpp - Nap | Cpp - Nle |
| cPzACAla - Met (O) | cPzACAla - Met (S—Me) | cPzACAla - MeVal | cPzACAla - Mpt | cPzACAla - Nap | cPzACAla - Nle |
| Cys - Met (O) | Cys - Met (S—Me) | Cys - MeVal | Cys - Mpt | Cys - Nap | Cys - Nle |
| Dap - Met (O) | Dap - Met (S—Me) | Dap - MeVal | Dap - Mpt | Dap - Nap | Dap - Nle |
| Dbf - Met(O) | Dbf - Met (S—Me) | Dbf - MeVal | Dbf - Mpt | Dbf - Nap | Dbf - Nle |
| Dbu - Met (O) | Dbu - Met (S—Me) | Dbu - MeVal | Dbu - Mpt | Dbu - Nap | Dbu - Nle |
| Des - Met (O) | Des - Met (S—Me) | Des - MeVal | Des - Mpt | Des - Nap | Des - Nle |
| Dip - Met (O) | Dip - Met (S—Me) | Dip - MeVal | Dip - Mpt | Dip - Nap | Dip - Nle |
| Dph - Met (O) | Dph - Met (S—Me) | Dph - MeVal | Dph - Mpt | Dph - Nap | Dph - Nle |
| Dpm - Met (O) | Dpm - Met (S—Me) | Dpm - MeVal | Dpm - Mpt | Dpm - Nap | Dpm - Nle |
| Dpr - Met (O) | Dpr - Met (S—Me) | Dpr - MeVal | Dpr - Mpt | Dpr - Nap | Dpr - Nle |
| EtAsn - Met (O) | EtAsn - Met (S—Me) | EtAsn - MeVal | EtAsn - Mpt | EtAsn - Nap | EtAsn - Nle |
| EtGly - Met (O) | EtGly - Met (S—Me) | EtGly - MeVal | EtGly - Mpt | EtGly - Nap | EtGly - Nle |
| gAbu - Met (O) | gAbu - Met (S—Me) | gAbu - MeVal | gAbu - Mpt | gAbu - Nap | gAbu - Nle |
| Gln - Met (O) | Gln - Met (S—Me) | Gln - MeVal | Gln - Mpt | Gln - Nap | Gln - Nle |
| Glu - Met (O) | Glu - Met (S—Me) | Glu - MeVal | Glu - Mpt | Glu - Nap | Glu - Nle |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| Gly - Met (O) | Gly - Met (S—Me) | Gly - MeVal | Gly - Mpt | Gly - Nap | Gly - Nle |
| Gly(Ph) - Met (O) | Gly(Ph) - Met (S—Me) | Gly(Ph) - MeVal | Gly(Ph) - Mpt | Gly(Ph) - Nap | Gly(Ph) - Nle |
| Har - Met (O) | Har - Met (S—Me) | Har - MeVal | Har - Mpt | Har - Nap | Har - Nle |
| Hcy - Met (O) | Hcy - Met (S—Me) | Hcy - MeVal | Hcy - Mpt | Hcy - Nap | Hcy - Nle |
| Hib - Met (O) | Hib - Met (S—Me) | Hib - MeVal | Hib - Mpt | Hib - Nap | Hib - Nle |
| His - Met (O) | His - Met (S—Me) | His - MeVal | His - Mpt | His - Nap | His - Nle |
| Hse - Met (O) | Hse - Met (S—Me) | Hse - MeVal | Hse - Mpt | Hse - Nap | Hse - Nle |
| Hyl - Met (O) | Hyl - Met (S—Me) | Hyl - MeVal | Hyl - Mpt | Hyl - Nap | Hyl - Nle |
| Hyp - Met (O) | Hyp - Met (S—Me) | Hyp - MeVal | Hyp - Mpt | Hyp - Nap | Hyp - Nle |
| Ide - Met (O) | Ide - Met (S—Me) | Ide - MeVal | Ide - Mpt | Ide - Nap | Ide - Nle |
| Ile - Met (O) | Ile - Met (S—Me) | Ile - MeVal | Ile - Mpt | Ile - Nap | Ile - Nle |
| Iva - Met (O) | Iva - Met (S—Me) | Iva - MeVal | Iva - Mpt | Iva - Nap | Iva - Nle |
| Leu - Met (O) | Leu - Met (S—Me) | Leu - MeVal | Leu - Mpt | Leu - Nap | Leu - Nle |
| Lys - Met (O) | Lys - Met (S—Me) | Lys - MeVal | Lys - Mpt | Lys - Nap | Lys - Nle |
| MeGly - Met (O) | MeGly - Met (S—Me) | MeGly - MeVal | MeGly - Mpt | MeGly - Nap | MeGly - Nle |
| MeIle - Met (O) | MeIle - Met (S—Me) | MeIle - MeVal | MeIle - Mpt | MeIle - Nap | MeIle - Nle |
| MeLys - Met (O) | MeLys - Met (S—Me) | MeLys - MeVal | MeLys - Mpt | MeLys - Nap | MeLys - Nle |
| Met - Met (O) | Met - Met (S—Me) | Met - MeVal | Met - Mpt | Met - Nap | Met - Nle |
| Met (O) - Met (O) | Met (O) - Met (S—Me) | Met (O) - MeVal | Met (O) - Mpt | Met (O) - Nap | Met (O) - Nle |
| Met (S—Me) - Met (O) | Met (S—Me) - Met (S—Me) | Met (S—Me) - MeVal | Met (S—Me) - Mpt | Met (S—Me) - Nap | Met (S—Me) - Nle |
| MeVal - Met (O) | MeVal - Met (S—Me) | MeVal - MeVal | MeVal - Mpt | MeVal - Nap | MeVal - Nle |
| Mpt - Met (O) | Mpt - Met (S—Me) | Mpt - MeVal | Mpt - Mpt | Mpt - Nap | Mpt - Nle |
| Nap - Met (O) | Nap - Met (S—Me) | Nap - MeVal | Nap - Mpt | Nap - Nap | Nap - Nle |
| Nle - Met (O) | Nle - Met (S—Me) | Nle - MeVal | Nle - Mpt | Nle - Nap | Nle - Nle |
| Nva - Met (O) | Nva - Met (S—Me) | Nva - MeVal | Nva - Mpt | Nva - Nap | Nva - Nle |
| Oic - Met (O) | Oic - Met (S—Me) | Oic - MeVal | Oic - Mpt | Oic - Nap | Oic - Nle |
| Opt - Met (O) | Opt - Met (S—Me) | Opt - MeVal | Opt - Mpt | Opt - Nap | Opt - Nle |
| Orn - Met (O) | Orn - Met (S—Me) | Orn - MeVal | Orn - Mpt | Orn - Nap | Orn - Nle |
| Pen - Met (O) | Pen - Met (S—Me) | Pen - MeVal | Pen - Mpt | Pen - Nap | Pen - Nle |
| Phe - Met (O) | Phe - Met (S—Me) | Phe - MeVal | Phe - Mpt | Phe - Nap | Phe - Nle |
| Phg - Met (O) | Phg - Met (S—Me) | Phg - MeVal | Phg - Mpt | Phg - Nap | Phg - Nle |
| Pip - Met (O) | Pip - Met (S—Me) | Pip - MeVal | Pip - Mpt | Pip - Nap | Pip - Nle |
| Pmp - Met (O) | Pmp - Met (S—Me) | Pmp - MeVal | Pmp - Mpt | Pmp - Nap | Pmp - Nle |
| Pro - Met (O) | Pro - Met (S—Me) | Pro - MeVal | Pro - Mpt | Pro - Nap | Pro - Nle |
| Qal - Met (O) | Qal - Met (S—Me) | Qal - MeVal | Qal - Mpt | Qal - Nap | Qal - Nle |
| Qua - Met (O) | Qua - Met (S—Me) | Qua - MeVal | Qua - Mpt | Qua - Nap | Qua - Nle |
| Sar - Met (O) | Sar - Met (S—Me) | Sar - MeVal | Sar - Mpt | Sar - Nap | Sar - Nle |
| Ser - Met (O) | Ser - Met (S—Me) | Ser - MeVal | Ser - Mpt | Ser - Nap | Ser - Nle |
| Thi - Met (O) | Thi - Met (S—Me) | Thi - MeVal | Thi - Mpt | Thi - Nap | Thi - Nle |
| Thr - Met (O) | Thr - Met (S—Me) | Thr - MeVal | Thr - Mpt | Thr - Nap | Thr - Nle |
| Tic - Met (O) | Tic - Met (S—Me) | Tic - MeVal | Tic - Mpt | Tic - Nap | Tic - Nle |
| Trp - Met (O) | Trp - Met (S—Me) | Trp - MeVal | Trp - Mpt | Trp - Nap | Trp - Nle |
| Tyr - Met (O) | Tyr - Met (S—Me) | Tyr - MeVal | Tyr - Mpt | Tyr - Nap | Tyr - Nle |
| Val - Met (O) | Val - Met (S—Me) | Val - MeVal | Val - Mpt | Val - Nap | Val - Nle |
| βAla - Met (O) | βAla - Met (S—Me) | βAla - MeVal | βAla - Mpt | βAla - Nap | βAla - Nle |
| D-TIC - Nva | D-TIC - Oic | D-TIC - Opt | D-TIC - Orn | D-TIC - Pen | D-TIC - Phe |
| GABA - Nva | GABA - Oic | GABA - Opt | GABA - Orn | GABA - Pen | GABA - Phe |
| EACA - Nva | EACA - Oic | EACA - Opt | EACA - Orn | EACA - Pen | EACA - Phe |
| K[TFA] - Nva | K[TFA] - Oic | K[TFA] - Opt | K[TFA] - Orn | K[TFA] - Pen | K[TFA] - Phe |
| 1-Nal - Nva | 1-Nal - Oic | 1-Nal - Opt | 1-Nal - Orn | 1-Nal - Pen | 1-Nal - Phe |
| 2-Nal - Nva | 2-Nal - Oic | 2-Nal - Opt | 2-Nal - Orn | 2-Nal - Pen | 2-Nal - Phe |
| 3Hyp - Nva | 3Hyp - Oic | 3Hyp - Opt | 3Hyp - Orn | 3Hyp - Pen | 3Hyp - Phe |
| 3-Pal - Nva | 3-Pal - Oic | 3-Pal - Opt | 3-Pal - Orn | 3-Pal - Pen | 3-Pal - Phe |
| 4Abu - Nva | 4Abu - Oic | 4Abu - Opt | 4Abu - Orn | 4Abu - Pen | 4Abu - Phe |
| 4Hyp - Nva | 4Hyp - Oic | 4Hyp - Opt | 4Hyp - Orn | 4Hyp - Pen | 4Hyp - Phe |
| A2bu - Nva | A2bu - Oic | A2bu - Opt | A2bu - Orn | A2bu - Pen | A2bu - Phe |
| A2pr - Nva | A2pr - Oic | A2pr - Opt | A2pr - Orn | A2pr - Pen | A2pr - Phe |
| Aad - Nva | Aad - Oic | Aad - Opt | Aad - Orn | Aad - Pen | Aad - Phe |
| aAhx - Nva | aAhx - Oic | aAhx - Opt | aAhx - Orn | aAhx - Pen | aAhx - Phe |
| Abo - Nva | Abo - Oic | Abo - Opt | Abo - Orn | Abo - Pen | Abo - Phe |
| Abu - Nva | Abu - Oic | Abu - Opt | Abu - Orn | Abu - Pen | Abu - Phe |
| ACCA - Nva | ACCA - Oic | ACCA - Opt | ACCA - Orn | ACCA - Pen | ACCA - Phe |
| Acp - Nva | Acp - Oic | Acp - Opt | Acp - Orn | Acp - Pen | Acp - Phe |
| Ahe - Nva | Ahe - Oic | Ahe - Opt | Ahe - Orn | Ahe - Pen | Ahe - Phe |
| Ahx - Nva | Ahx - Oic | Ahx - Opt | Ahx - Orn | Ahx - Pen | Ahx - Phe |
| aHyl - Nva | aHyl - Oic | aHyl - Opt | aHyl - Orn | aHyl - Pen | aHyl - Phe |
| Aib - Nva | Aib - Oic | Aib - Opt | Aib - Orn | Aib - Pen | Aib - Phe |
| Aib - Nva | Aib - Oic | Aib - Opt | Aib - Orn | Aib - Pen | Aib - Phe |
| Aic - Nva | Aic - Oic | Aic - Opt | Aic - Orn | Aic - Pen | Aic - Phe |
| aIle - Nva | aIle - Oic | aIle - Opt | aIle - Orn | aIle - Pen | aIle - Phe |
| Ala - Nva | Ala - Oic | Ala - Opt | Ala - Orn | Ala - Pen | Ala - Phe |
| Apm - Nva | Apm - Oic | Apm - Opt | Apm - Orn | Apm - Pen | Apm - Phe |
| Arg - Nva | Arg - Oic | Arg - Opt | Arg - Orn | Arg - Pen | Arg - Phe |
| Asn - Nva | Asn - Oic | Asn - Opt | Asn - Orn | Asn - Pen | Asn - Phe |
| Asp - Nva | Asp - Oic | Asp - Opt | Asp - Orn | Asp - Pen | Asp - Phe |

TABLE 5-continued

Illustrative combinations for $X^2 - X^3$ and/or $X^3 - X^4$.

| I-P | P-D | P-F | F-H | V-A | A-G |
|---|---|---|---|---|---|
| Atc - Nva | Atc - Oic | Atc - Opt | Atc - Orn | Atc - Pen | Atc - Phe |
| Ava - Nva | Ava - Oic | Ava - Opt | Ava - Orn | Ava - Pen | Ava - Phe |
| Aze - Nva | Aze - Oic | Aze - Opt | Aze - Orn | Aze - Pen | Aze - Phe |
| bAad - Nva | bAad - Oic | bAad - Opt | bAad - Orn | bAad - Pen | bAad - Phe |
| bAib - Nva | bAib - Oic | bAib - Opt | bAib - Orn | bAib - Pen | bAib - Phe |
| bAla - Nva | bAla - Oic | bAla - Opt | bAla - Orn | bAla - Pen | bAla - Phe |
| Cha - Nva | Cha - Oic | Cha - Opt | Cha - Orn | Cha - Pen | Cha - Phe |
| Cpg - Nva | Cpg - Oic | Cpg - Opt | Cpg - Orn | Cpg - Pen | Cpg - Phe |
| Cpp - Nva | Cpp - Oic | Cpp - Opt | Cpp - Orn | Cpp - Pen | Cpp - Phe |
| cPzACAla - Nva | cPzACAla - Oic | cPzACAla - Opt | cPzACAla - Orn | cPzACAla - Pen | cPzACAla - Phe |
| Cys - Nva | Cys - Oic | Cys - Opt | Cys - Orn | Cys - Pen | Cys - Phe |
| Dap - Nva | Dap - Oic | Dap - Opt | Dap - Orn | Dap - Pen | Dap - Phe |
| Dbf - Nva | Dbf - Oic | Dbf - Opt | Dbf - Orn | Dbf - Pen | Dbf - Phe |
| Dbu - Nva | Dbu - Oic | Dbu - Opt | Dbu - Orn | Dbu - Pen | Dbu - Phe |
| Des - Nva | Des - Oic | Des - Opt | Des - Orn | Des - Pen | Des - Phe |
| Dip - Nva | Dip - Oic | Dip - Opt | Dip - Orn | Dip - Pen | Dip - Phe |
| Dph - Nva | Dph - Oic | Dph - Opt | Dph - Orn | Dph - Pen | Dph - Phe |
| Dpm - Nva | Dpm - Oic | Dpm - Opt | Dpm - Orn | Dpm - Pen | Dpm - Phe |
| Dpr - Nva | Dpr - Oic | Dpr - Opt | Dpr - Orn | Dpr - Pen | Dpr - Phe |
| EtAsn - Nva | EtAsn - Oic | EtAsn - Opt | EtAsn - Orn | EtAsn - Pen | EtAsn - Phe |
| EtGly - Nva | EtGly - Oic | EtGly - Opt | EtGly - Orn | EtGly - Pen | EtGly - Phe |
| gAbu - Nva | gAbu - Oic | gAbu - Opt | gAbu - Orn | gAbu - Pen | gAbu - Phe |
| Gln - Nva | Gln - Oic | Gln - Opt | Gln - Orn | Gln - Pen | Gln - Phe |
| Glu - Nva | Glu - Oic | Glu - Opt | Glu - Orn | Glu - Pen | Glu - Phe |
| Gly - Nva | Gly - Oic | Gly - Opt | Gly - Orn | Gly - Pen | Gly - Phe |
| Gly(Ph) - Nva | Gly(Ph) - Oic | Gly(Ph) - Opt | Gly(Ph) - Orn | Gly(Ph) - Pen | Gly(Ph) - Phe |
| Har - Nva | Har - Oic | Har - Opt | Har - Orn | Har - Pen | Har - Phe |
| Hcy - Nva | Hcy - Oic | Hcy - Opt | Hcy - Orn | Hcy - Pen | Hcy - Phe |
| Hib - Nva | Hib - Oic | Hib - Opt | Hib - Orn | Hib - Pen | Hib - Phe |
| His - Nva | His - Oic | His - Opt | His - Orn | His - Pen | His - Phe |
| Hse - Nva | Hse - Oic | Hse - Opt | Hse - Orn | Hse - Pen | Hse - Phe |
| Hyl - Nva | Hyl - Oic | Hyl - Opt | Hyl - Orn | Hyl - Pen | Hyl - Phe |
| Hyp - Nva | Hyp - Oic | Hyp - Opt | Hyp - Orn | Hyp - Pen | Hyp - Phe |
| Ide - Nva | Ide - Oic | Ide - Opt | Ide - Orn | Ide - Pen | Ide - Phe |
| Ile - Nva | Ile - Oic | Ile - Opt | Ile - Orn | Ile - Pen | Ile - Phe |
| Iva - Nva | Iva - Oic | Iva - Opt | Iva - Orn | Iva - Pen | Iva - Phe |
| Leu - Nva | Leu - Oic | Leu - Opt | Leu - Orn | Leu - Pen | Leu - Phe |
| Lys - Nva | Lys - Oic | Lys - Opt | Lys - Orn | Lys - Pen | Lys - Phe |
| MeGly - Nva | MeGly - Oic | MeGly - Opt | MeGly - Orn | MeGly - Pen | MeGly - Phe |
| MeIle - Nva | MeIle - Oic | MeIle - Opt | MeIle - Orn | MeIle - Pen | MeIle - Phe |
| MeLys - Nva | MeLys - Oic | MeLys - Opt | MeLys - Orn | MeLys - Pen | MeLys - Phe |
| Met - Nva | Met - Oic | Met - Opt | Met - Orn | Met - Pen | Met - Phe |
| Met (O) - Nva | Met (O) - Oic | Met (O) - Opt | Met (O) - Orn | Met (O) - Pen | Met (O) - Phe |
| Met (S—Me) - Nva | Met (S—Me) - Oic | Met (S—Me) - Opt | Met (S—Me) - Orn | Met (S—Me) - Pen | Met (S—Me) - Phe |
| MeVal - Nva | MeVal - Oic | MeVal - Opt | MeVal - Orn | MeVal - Pen | MeVal - Phe |
| Mpt - Nva | Mpt - Oic | Mpt - Opt | Mpt - Orn | Mpt - Pen | Mpt - Phe |
| Nap - Nva | Nap - Oic | Nap - Opt | Nap - Orn | Nap - Pen | Nap - Phe |
| Nle - Nva | Nle - Oic | Nle - Opt | Nle - Orn | Nle - Pen | Nle - Phe |
| Nva - Nva | Nva - Oic | Nva - Opt | Nva - Orn | Nva - Pen | Nva - Phe |
| Oic - Nva | Oic - Oic | Oic - Opt | Oic - Orn | Oic - Pen | Oic - Phe |
| Opt - Nva | Opt - Oic | Opt - Opt | Opt - Orn | Opt - Pen | Opt - Phe |
| Orn - Nva | Orn - Oic | Orn - Opt | Orn - Orn | Orn - Pen | Orn - Phe |
| Pen - Nva | Pen - Oic | Pen - Opt | Pen - Orn | Pen - Pen | Pen - Phe |
| Phe - Nva | Phe - Oic | Phe - Opt | Phe - Orn | Phe - Pen | Phe - Phe |
| Phg - Nva | Phg - Oic | Phg - Opt | Phg - Orn | Phg - Pen | Phg - Phe |
| Pip - Nva | Pip - Oic | Pip - Opt | Pip - Orn | Pip - Pen | Pip - Phe |
| Pmp - Nva | Pmp - Oic | Pmp - Opt | Pmp - Orn | Pmp - Pen | Pmp - Phe |
| Pro - Nva | Pro - Oic | Pro - Opt | Pro - Orn | Pro - Pen | Pro - Phe |
| Qal - Nva | Qal - Oic | Qal - Opt | Qal - Orn | Qal - Pen | Qal - Phe |
| Qua - Nva | Qua - Oic | Qua - Opt | Qua - Orn | Qua - Pen | Qua - Phe |
| Sar - Nva | Sar - Oic | Sar - Opt | Sar - Orn | Sar - Pen | Sar - Phe |
| Ser - Nva | Ser - Oic | Ser - Opt | Ser - Orn | Ser - Pen | Ser - Phe |
| Thi - Nva | Thi - Oic | Thi - Opt | Thi - Orn | Thi - Pen | Thi - Phe |
| Thr - Nva | Thr - Oic | Thr - Opt | Thr - Orn | Thr - Pen | Thr - Phe |
| Tic - Nva | Tic - Oic | Tic - Opt | Tic - Orn | Tic - Pen | Tic - Phe |
| Trp - Nva | Trp - Oic | Trp - Opt | Trp - Orn | Trp - Pen | Trp - Phe |
| Tyr - Nva | Tyr - Oic | Tyr - Opt | Tyr - Orn | Tyr - Pen | Tyr - Phe |
| Val - Nva | Val - Oic | Val - Opt | Val - Orn | Val - Pen | Val - Phe |
| βAla - Nva | βAla - Oic | βAla - Opt | βAla - Orn | βAla - Pen | βAla - Phe |
| D-TIC - Phg | D-TIC - Pmp | D-TIC - Pro | D-TIC - Pmp | D-TIC - Qal | D-TIC - Qua |
| GABA - Phg | GABA - Pip | GABA - Pmp | GABA - Pro | GABA - Qal | GABA - Qua |
| EACA - Phg | EACA - Pip | EACA - Pmp | EACA - Pro | EACA - Qal | EACA - Qua |
| K[TFA] - Phg | K[TFA] - Pip | K[TFA] - Pmp | K[TFA] - Pro | K[TFA] - Qal | K[TFA] - Qua |
| 1-Nal - Phg | 1-Nal - Pip | 1-Nal - Pmp | 1-Nal - Pro | 1-Nal - Qal | 1-Nal - Qua |
| 2-Nal - Phg | 2-Nal - Pip | 2-Nal - Pmp | 2-Nal - Pro | 2-Nal - Qal | 2-Nal - Qua |

TABLE 5-continued

Illustrative combinations for $X^2 - X^3$ and/or $X^3 - X^4$.

| I-P | P-D | P-F | F-H | V-A | A-G |
|---|---|---|---|---|---|
| 3Hyp - Phg | 3Hyp - Pip | 3Hyp - Pmp | 3Hyp - Pro | 3Hyp - Qal | 3Hyp - Qua |
| 3-Pal - Phg | 3-Pal - Pip | 3-Pal - Pmp | 3-Pal - Pro | 3-Pal - Qal | 3-Pal - Qua |
| 4Abu - Phg | 4Abu - Pip | 4Abu - Pmp | 4Abu - Pro | 4Abu - Qal | 4Abu - Qua |
| 4Hyp - Phg | 4Hyp - Pip | 4Hyp - Pmp | 4Hyp - Pro | 4Hyp - Qal | 4Hyp - Qua |
| A2bu - Phg | A2bu - Pip | A2bu - Pmp | A2bu - Pro | A2bu - Qal | A2bu - Qua |
| A2pr - Phg | A2pr - Pip | A2pr - Pmp | A2pr - Pro | A2pr - Qal | A2pr - Qua |
| Aad - Phg | Aad - Pip | Aad - Pmp | Aad - Pro | Aad - Qal | Aad - Qua |
| aAhx - Phg | aAhx - Pip | aAhx - Pmp | aAhx - Pro | aAhx - Qal | aAhx - Qua |
| Abo - Phg | Abo - Pip | Abo - Pmp | Abo - Pro | Abo - Qal | Abo - Qua |
| Abu - Phg | Abu - Pip | Abu - Pmp | Abu - Pro | Abu - Qal | Abu - Qua |
| ACCA - Phg | ACCA - Pip | ACCA - Pmp | ACCA - Pro | ACCA - Qal | ACCA - Qua |
| Acp - Phg | Acp - Pip | Acp - Pmp | Acp - Pro | Acp - Qal | Acp - Qua |
| Ahe - Phg | Ahe - Pip | Ahe - Pmp | Ahe - Pro | Ahe - Qal | Ahe - Qua |
| Ahx - Phg | Ahx - Pip | Ahx - Pmp | Ahx - Pro | Ahx - Qal | Ahx - Qua |
| aHyl - Phg | aHyl - Pip | aHyl - Pmp | aHyl - Pro | aHyl - Qal | aHyl - Qua |
| Aib - Phg | Aib - Pip | Aib - Pmp | Aib - Pro | Aib - Qal | Aib - Qua |
| Aib - Phg | Aib - Pip | Aib - Pmp | Aib - Pro | Aib - Qal | Aib - Qua |
| Aic - Phg | Aic - Pip | Aic - Pmp | Aic - Pro | Aic - Qal | Aic - Qua |
| aIle - Phg | aIle - Pip | aIle - Pmp | aIle - Pro | aIle - Qal | aIle - Qua |
| Ala - Phg | Ala - Pip | Ala - Pmp | Ala - Pro | Ala - Qal | Ala - Qua |
| Apm - Phg | Apm - Pip | Apm - Pmp | Apm - Pro | Apm - Qal | Apm - Qua |
| Arg - Phg | Arg - Pip | Arg - Pmp | Arg - Pro | Arg - Qal | Arg - Qua |
| Asn - Phg | Asn - Pip | Asn - Pmp | Asn - Pro | Asn - Qal | Asn - Qua |
| Asp - Phg | Asp - Pip | Asp - Pmp | Asp - Pro | Asp - Qal | Asp - Qua |
| Atc - Phg | Atc - Pip | Atc - Pmp | Atc - Pro | Atc - Qal | Atc - Qua |
| Ava - Phg | Ava - Pip | Ava - Pmp | Ava - Pro | Ava - Qal | Ava - Qua |
| Aze - Phg | Aze - Pip | Aze - Pmp | Aze - Pro | Aze - Qal | Aze - Qua |
| bAad - Phg | bAad - Pip | bAad - Pmp | bAad - Pro | bAad - Qal | bAad - Qua |
| bAib - Phg | bAib - Pip | bAib - Pmp | bAib - Pro | bAib - Qal | bAib - Qua |
| bAla - Phg | bAla - Pip | bAla - Pmp | bAla - Pro | bAla - Qal | bAla - Qua |
| Cha - Phg | Cha - Pip | Cha - Pmp | Cha - Pro | Cha - Qal | Cha - Qua |
| Cpg - Phg | Cpg - Pip | Cpg - Pmp | Cpg - Pro | Cpg - Qal | Cpg - Qua |
| Cpp - Phg | Cpp - Pip | Cpp - Pmp | Cpp - Pro | Cpp - Qal | Cpp - Qua |
| cPzACAla - Phg | cPzACAla - Pip | cPzACAla - Pmp | cPzACAla - Pro | cPzACAla - Qal | cPzACAla - Qua |
| Cys - Phg | Cys - Pip | Cys - Pmp | Cys - Pro | Cys - Qal | Cys - Qua |
| Dap - Phg | Dap - Pip | Dap - Pmp | Dap - Pro | Dap - Qal | Dap - Qua |
| Dbf - Phg | Dbf - Pip | Dbf - Pmp | Dbf - Pro | Dbf - Qal | Dbf - Qua |
| Dbu - Phg | Dbu - Pip | Dbu - Pmp | Dbu - Pro | Dbu - Qal | Dbu - Qua |
| Des - Phg | Des - Pip | Des - Pmp | Des - Pro | Des - Qal | Des - Qua |
| Dip - Phg | Dip - Pip | Dip - Pmp | Dip - Pro | Dip - Qal | Dip - Qua |
| Dph - Phg | Dph - Pip | Dph - Pmp | Dph - Pro | Dph - Qal | Dph - Qua |
| Dpm - Phg | Dpm - Pip | Dpm - Pmp | Dpm - Pro | Dpm - Qal | Dpm - Qua |
| Dpr - Phg | Dpr - Pip | Dpr - Pmp | Dpr - Pro | Dpr - Qal | Dpr - Qua |
| EtAsn - Phg | EtAsn - Pip | EtAsn - Pmp | EtAsn - Pro | EtAsn - Qal | EtAsn - Qua |
| EtGly - Phg | EtGly - Pip | EtGly - Pmp | EtGly - Pro | EtGly - Qal | EtGly - Qua |
| gAbu - Phg | gAbu - Pip | gAbu - Pmp | gAbu - Pro | gAbu - Qal | gAbu - Qua |
| Gln - Phg | Gln - Pip | Gln - Pmp | Gln - Pro | Gln - Qal | Gln - Qua |
| Glu - Phg | Glu - Pip | Glu - Pmp | Glu - Pro | Glu - Qal | Glu - Qua |
| Gly - Phg | Gly - Pip | Gly - Pmp | Gly - Pro | Gly - Qal | Gly - Qua |
| Gly(Ph) - Phg | Gly(Ph) - Pip | Gly(Ph) - Pmp | Gly(Ph) - Pro | Gly(Ph) - Qal | Gly(Ph) - Qua |
| Har - Phg | Har - Pip | Har - Pmp | Har - Pro | Har - Qal | Har - Qua |
| Hcy - Phg | Hcy - Pip | Hcy - Pmp | Hcy - Pro | Hcy - Qal | Hcy - Qua |
| Hib - Phg | Hib - Pip | Hib - Pmp | Hib - Pro | Hib - Qal | Hib - Qua |
| His - Phg | His - Pip | His - Pmp | His - Pro | His - Qal | His - Qua |
| Hse - Phg | Hse - Pip | Hse - Pmp | Hse - Pro | Hse - Qal | Hse - Qua |
| Hyl - Phg | Hyl - Pip | Hyl - Pmp | Hyl - Pro | Hyl - Qal | Hyl - Qua |
| Hyp - Phg | Hyp - Pip | Hyp - Pmp | Hyp - Pro | Hyp - Qal | Hyp - Qua |
| Ide - Phg | Ide - Pip | Ide - Pmp | Ide - Pro | Ide - Qal | Ide - Qua |
| Ile - Phg | Ile - Pip | Ile - Pmp | Ile - Pro | Ile - Qal | Ile - Qua |
| Iva - Phg | Iva - Pip | Iva - Pmp | Iva - Pro | Iva - Qal | Iva - Qua |
| Leu - Phg | Leu - Pip | Leu - Pmp | Leu - Pro | Leu - Qal | Leu - Qua |
| Lys - Phg | Lys - Pip | Lys - Pmp | Lys - Pro | Lys - Qal | Lys - Qua |
| MeGly - Phg | MeGly - Pip | MeGly - Pmp | MeGly - Pro | MeGly - Qal | MeGly - Qua |
| MeIle - Phg | MeIle - Pip | MeIle - Pmp | MeIle - Pro | MeIle - Qal | MeIle - Qua |
| MeLys - Phg | MeLys - Pip | MeLys - Pmp | MeLys - Pro | MeLys - Qal | MeLys - Qua |
| Met - Phg | Met - Pip | Met - Pmp | Met - Pro | Met - Qal | Met - Qua |
| Met (O) - Phg | Met (O) - Pip | Met (O) - Pmp | Met (O) - Pro | Met (O) - Qal | Met (O) - Qua |
| Met (S—Me) - Phg | Met (S—Me) - Pip | Met (S—Me) - Pmp | Met (S—Me) - Pro | Met (S—Me) - Qal | Met (S—Me) - Qua |
| MeVal - Phg | MeVal - Pip | MeVal - Pmp | MeVal - Pro | MeVal - Qal | MeVal - Qua |
| Mpt - Phg | Mpt - Pip | Mpt - Pmp | Mpt - Pro | Mpt - Qal | Mpt - Qua |
| Nap - Phg | Nap - Pip | Nap - Pmp | Nap - Pro | Nap - Qal | Nap - Qua |
| Nle - Phg | Nle - Pip | Nle - Pmp | Nle - Pro | Nle - Qal | Nle - Qua |
| Nva - Phg | Nva - Pip | Nva - Pmp | Nva - Pro | Nva - Qal | Nva - Qua |
| Oic - Phg | Oic - Pip | Oic - Pmp | Oic - Pro | Oic - Qal | Oic - Qua |
| Opt - Phg | Opt - Pip | Opt - Pmp | Opt - Pro | Opt - Qal | Opt - Qua |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| Orn - Phg | Orn - Pip | Orn - Pmp | Orn - Pro | Orn - Qal | Orn - Qua |
| Pen - Phg | Pen - Pip | Pen - Pmp | Pen - Pro | Pen - Qal | Pen - Qua |
| Phe - Phg | Phe - Pip | Phe - Pmp | Phe - Pro | Phe - Qal | Phe - Qua |
| Phg - Phg | Phg - Pip | Phg - Pmp | Phg - Pro | Phg - Qal | Phg - Qua |
| Pip - Phg | Pip - Pip | Pip - Pmp | Pip - Pro | Pip - Qal | Pip - Qua |
| Pmp - Phg | Pmp - Pip | Pmp - Pmp | Pmp - Pro | Pmp - Qal | Pmp - Qua |
| Pro - Phg | Pro - Pip | Pro - Pmp | Pro - Pro | Pro - Qal | Pro - Qua |
| Qal - Phg | Qal - Pip | Qal - Pmp | Qal - Pro | Qal - Qal | Qal - Qua |
| Qua - Phg | Qua - Pip | Qua - Pmp | Qua - Pro | Qua - Qal | Qua - Qua |
| Sar - Phg | Sar - Pip | Sar - Pmp | Sar - Pro | Sar - Qal | Sar - Qua |
| Ser - Phg | Ser - Pip | Ser - Pmp | Ser - Pro | Ser - Qal | Ser - Qua |
| Thi - Phg | Thi - Pip | Thi - Pmp | Thi - Pro | Thi - Qal | Thi - Qua |
| Thr - Phg | Thr - Pip | Thr - Pmp | Thr - Pro | Thr - Qal | Thr - Qua |
| Tic - Phg | Tic - Pip | Tic - Pmp | Tic - Pro | Tic - Qal | Tic - Qua |
| Trp - Phg | Trp - Pip | Trp - Pmp | Trp - Pro | Trp - Qal | Trp - Qua |
| Tyr - Phg | Tyr - Pip | Tyr - Pmp | Tyr - Pro | Tyr - Qal | Tyr - Qua |
| Val - Phg | Val - Pip | Val - Pmp | Val - Pro | Val - Qal | Val - Qua |
| βAla - Phg | βAla - Pip | βAla - Pmp | βAla - Pro | βAla - Qal | βAla - Qua |
| D-TIC - Sar | D-TIC - Ser | D-TIC - Thi | D-TIC - Thr | D-TIC - Tic | D-TIC - Trp |
| GABA - Sar | GABA - Ser | GABA - Thi | GABA - Thr | GABA - Tic | GABA - Trp |
| EACA - Sar | EACA - Ser | EACA - Thi | EACA - Thr | EACA - Tic | EACA - Trp |
| K[TFA] - Sar | K[TFA] - Ser | K[TFA] - Thi | K[TFA] - Thr | K[TFA] - Tic | K[TFA] - Trp |
| 1-Nal - Sar | 1-Nal - Ser | 1-Nal - Thi | 1-Nal - Thr | 1-Nal - Tic | 1-Nal - Trp |
| 2-Nal - Sar | 2-Nal - Ser | 2-Nal - Thi | 2-Nal - Thr | 2-Nal - Tic | 2-Nal - Trp |
| 3Hyp - Sar | 3Hyp - Ser | 3Hyp - Thi | 3Hyp - Thr | 3Hyp - Tic | 3Hyp - Trp |
| 3-Pal - Sar | 3-Pal - Ser | 3-Pal - Thi | 3-Pal - Thr | 3-Pal - Tic | 3-Pal - Trp |
| 4Abu - Sar | 4Abu - Ser | 4Abu - Thi | 4Abu - Thr | 4Abu - Tic | 4Abu - Trp |
| 4Hyp - Sar | 4Hyp - Ser | 4Hyp - Thi | 4Hyp - Thr | 4Hyp - Tic | 4Hyp - Trp |
| A2bu - Sar | A2bu - Ser | A2bu - Thi | A2bu - Thr | A2bu - Tic | A2bu - Trp |
| A2pr - Sar | A2pr - Ser | A2pr - Thi | A2pr - Thr | A2pr - Tic | A2pr - Trp |
| Aad - Sar | Aad - Ser | Aad - Thi | Aad - Thr | Aad - Tic | Aad - Trp |
| aAhx - Sar | aAhx - Ser | aAhx - Thi | aAhx - Thr | aAhx - Tic | aAhx - Trp |
| Abo - Sar | Abo - Ser | Abo - Thi | Abo - Thr | Abo - Tic | Abo - Trp |
| Abu - Sar | Abu - Ser | Abu - Thi | Abu - Thr | Abu - Tic | Abu - Trp |
| ACCA - Sar | ACCA - Ser | ACCA - Thi | ACCA - Thr | ACCA - Tic | ACCA - Trp |
| Acp - Sar | Acp - Ser | Acp - Thi | Acp - Thr | Acp - Tic | Acp - Trp |
| Ahe - Sar | Ahe - Ser | Ahe - Thi | Ahe - Thr | Ahe - Tic | Ahe - Trp |
| Ahx - Sar | Ahx - Ser | Ahx - Thi | Ahx - Thr | Ahx - Tic | Ahx - Trp |
| aHyl - Sar | aHyl - Ser | aHyl - Thi | aHyl - Thr | aHyl - Tic | aHyl - Trp |
| Aib - Sar | Aib - Ser | Aib - Thi | Aib - Thr | Aib - Tic | Aib - Trp |
| Aib - Sar | Aib - Ser | Aib - Thi | Aib - Thr | Aib - Tic | Aib - Trp |
| Aic - Sar | Aic - Ser | Aic - Thi | Aic - Thr | Aic - Tic | Aic - Trp |
| aIle - Sar | aIle - Ser | aIle - Thi | aIle - Thr | aIle - Tic | aIle - Trp |
| Ala - Sar | Ala - Ser | Ala - Thi | Ala - Thr | Ala - Tic | Ala - Trp |
| Apm - Sar | Apm - Ser | Apm - Thi | Apm - Thr | Apm - Tic | Apm - Trp |
| Arg - Sar | Arg - Ser | Arg - Thi | Arg - Thr | Arg - Tic | Arg - Trp |
| Asn - Sar | Asn - Ser | Asn - Thi | Asn - Thr | Asn - Tic | Asn - Trp |
| Asp - Sar | Asp - Ser | Asp - Thi | Asp - Thr | Asp - Tic | Asp - Trp |
| Atc - Sar | Atc - Ser | Atc - Thi | Atc - Thr | Atc - Tic | Atc - Trp |
| Ava - Sar | Ava - Ser | Ava - Thi | Ava - Thr | Ava - Tic | Ava - Trp |
| Aze - Sar | Aze - Ser | Aze - Thi | Aze - Thr | Aze - Tic | Aze - Trp |
| bAad - Sar | bAad - Ser | bAad - Thi | bAad - Thr | bAad - Tic | bAad - Trp |
| bAib - Sar | bAib - Ser | bAib - Thi | bAib - Thr | bAib - Tic | bAib - Trp |
| bAla - Sar | bAla - Ser | bAla - Thi | bAla - Thr | bAla - Tic | bAla - Trp |
| Cha - Sar | Cha - Ser | Cha - Thi | Cha - Thr | Cha - Tic | Cha - Trp |
| Cpg - Sar | Cpg - Ser | Cpg - Thi | Cpg - Thr | Cpg - Tic | Cpg - Trp |
| Cpp - Sar | Cpp - Ser | Cpp - Thi | Cpp - Thr | Cpp - Tic | Cpp - Trp |
| cPzACAla - Sar | cPzACAla - Ser | cPzACAla - Thi | cPzACAla - Thr | cPzACAla - Tic | cPzACAla - Trp |
| Cys - Sar | Cys - Ser | Cys - Thi | Cys - Thr | Cys - Tic | Cys - Trp |
| Dap - Sar | Dap - Ser | Dap - Thi | Dap - Thr | Dap - Tic | Dap - Trp |
| Dbf - Sar | Dbf - Ser | Dbf - Thi | Dbf - Thr | Dbf - Tic | Dbf - Trp |
| Dbu - Sar | Dbu - Ser | Dbu - Thi | Dbu - Thr | Dbu - Tic | Dbu - Trp |
| Des - Sar | Des - Ser | Des - Thi | Des - Thr | Des - Tic | Des - Trp |
| Dip - Sar | Dip - Ser | Dip - Thi | Dip - Thr | Dip - Tic | Dip - Trp |
| Dph - Sar | Dph - Ser | Dph - Thi | Dph - Thr | Dph - Tic | Dph - Trp |
| Dpm - Sar | Dpm - Ser | Dpm - Thi | Dpm - Thr | Dpm - Tic | Dpm - Trp |
| Dpr - Sar | Dpr - Ser | Dpr - Thi | Dpr - Thr | Dpr - Tic | Dpr - Trp |
| EtAsn - Sar | EtAsn - Ser | EtAsn - Thi | EtAsn - Thr | EtAsn - Tic | EtAsn - Trp |
| EtGly - Sar | EtGly - Ser | EtGly - Thi | EtGly - Thr | EtGly - Tic | EtGly - Trp |
| gAbu - Sar | gAbu - Ser | gAbu - Thi | gAbu - Thr | gAbu - Tic | gAbu - Trp |
| Gln - Sar | Gln - Ser | Gln - Thi | Gln - Thr | Gln - Tic | Gln - Trp |
| Glu - Sar | Glu - Ser | Glu - Thi | Glu - Thr | Glu - Tic | Glu - Trp |
| Gly - Sar | Gly - Ser | Gly - Thi | Gly - Thr | Gly - Tic | Gly - Trp |
| Gly(Ph) - Sar | Gly(Ph) - Ser | Gly(Ph) - Thi | Gly(Ph) - Thr | Gly(Ph) - Tic | Gly(Ph) - Trp |
| Har - Sar | Har - Ser | Har - Thi | Har - Thr | Har - Tic | Har - Trp |
| Hcy - Sar | Hcy - Ser | Hcy - Thi | Hcy - Thr | Hcy - Tic | Hcy - Trp |

TABLE 5-continued

Illustrative combinations for $X^2$ - $X^3$ and/or $X^3$ - $X^4$.

| I-P | P-D | P-F | F-H | V-A | A-G |
|---|---|---|---|---|---|
| Hib - Sar | Hib - Ser | Hib - Thi | Hib - Thr | Hib - Tic | Hib - Trp |
| His - Sar | His - Ser | His - Thi | His - Thr | His - Tic | His - Trp |
| Hse - Sar | Hse - Ser | Hse - Thi | Hse - Thr | Hse - Tic | Hse - Trp |
| Hyl - Sar | Hyl - Ser | Hyl - Thi | Hyl - Thr | Hyl - Tic | Hyl - Trp |
| Hyp - Sar | Hyp - Ser | Hyp - Thi | Hyp - Thr | Hyp - Tic | Hyp - Trp |
| Ide - Sar | Ide - Ser | Ide - Thi | Ide - Thr | Ide - Tic | Ide - Trp |
| Ile - Sar | Ile - Ser | Ile - Thi | Ile - Thr | Ile - Tic | Ile - Trp |
| Iva - Sar | Iva - Ser | Iva - Thi | Iva - Thr | Iva - Tic | Iva - Trp |
| Leu - Sar | Leu - Ser | Leu - Thi | Leu - Thr | Leu - Tic | Leu - Trp |
| Lys - Sar | Lys - Ser | Lys - Thi | Lys - Thr | Lys - Tic | Lys - Trp |
| MeGly - Sar | MeGly - Ser | MeGly - Thi | MeGly - Thr | MeGly - Tic | MeGly - Trp |
| MeIle - Sar | MeIle - Ser | MeIle - Thi | MeIle - Thr | MeIle - Tic | MeIle - Trp |
| MeLys - Sar | MeLys - Ser | MeLys - Thi | MeLys - Thr | MeLys - Tic | MeLys - Trp |
| Met - Sar | Met - Ser | Met - Thi | Met - Thr | Met - Tic | Met - Trp |
| Met (O) - Sar | Met (O) - Ser | Met (O) - Thi | Met (O) - Thr | Met (O) - Tic | Met (O) - Trp |
| Met (S—Me) - Sar | Met (S—Me) - Ser | Met (S—Me) - Thi | Met (S—Me) - Thr | Met (S—Me) - Tic | Met (S—Me) - Trp |
| MeVal - Sar | MeVal - Ser | MeVal - Thi | MeVal - Thr | MeVal - Tic | MeVal - Trp |
| Mpt - Sar | Mpt - Ser | Mpt - Thi | Mpt - Thr | Mpt - Tic | Mpt - Trp |
| Nap - Sar | Nap - Ser | Nap - Thi | Nap - Thr | Nap - Tic | Nap - Trp |
| Nle - Sar | Nle - Ser | Nle - Thi | Nle - Thr | Nle - Tic | Nle - Trp |
| Nva - Sar | Nva - Ser | Nva - Thi | Nva - Thr | Nva - Tic | Nva - Trp |
| Oic - Sar | Oic - Ser | Oic - Thi | Oic - Thr | Oic - Tic | Oic - Trp |
| Opt - Sar | Opt - Ser | Opt - Thi | Opt - Thr | Opt - Tic | Opt - Trp |
| Orn - Sar | Orn - Ser | Orn - Thi | Orn - Thr | Orn - Tic | Orn - Trp |
| Pen - Sar | Pen - Ser | Pen - Thi | Pen - Thr | Pen - Tic | Pen - Trp |
| Phe - Sar | Phe - Ser | Phe - Thi | Phe - Thr | Phe - Tic | Phe - Trp |
| Phg - Sar | Phg - Ser | Phg - Thi | Phg - Thr | Phg - Tic | Phg - Trp |
| Pip - Sar | Pip - Ser | Pip - Thi | Pip - Thr | Pip - Tic | Pip - Trp |
| Pmp - Sar | Pmp - Ser | Pmp - Thi | Pmp - Thr | Pmp - Tic | Pmp - Trp |
| Pro - Sar | Pro - Ser | Pro - Thi | Pro - Thr | Pro - Tic | Pro - Trp |
| Qal - Sar | Qal - Ser | Qal - Thi | Qal - Thr | Qal - Tic | Qal - Trp |
| Qua - Sar | Qua - Ser | Qua - Thi | Qua - Thr | Qua - Tic | Qua - Trp |
| Sar - Sar | Sar - Ser | Sar - Thi | Sar - Thr | Sar - Tic | Sar - Trp |
| Ser - Sar | Ser - Ser | Ser - Thi | Ser - Thr | Ser - Tic | Ser - Trp |
| Thi - Sar | Thi - Ser | Thi - Thi | Thi - Thr | Thi - Tic | Thi - Trp |
| Thr - Sar | Thr - Ser | Thr - Thi | Thr - Thr | Thr - Tic | Thr - Trp |
| Tic - Sar | Tic - Ser | Tic - Thi | Tic - Thr | Tic - Tic | Tic - Trp |
| Trp - Sar | Trp - Ser | Trp - Thi | Trp - Thr | Trp - Tic | Trp - Trp |
| Tyr - Sar | Tyr - Ser | Tyr - Thi | Tyr - Thr | Tyr - Tic | Tyr - Trp |
| Val - Sar | Val - Ser | Val - Thi | Val - Thr | Val - Tic | Val - Trp |
| βAla - Sar | βAla - Ser | βAla - Thi | βAla - Thr | βAla - Tic | βAla - Trp |
| D-TIC - Tyr | D-TIC - Val | D-TIC - βAla | D-TIC - βAla | Phe - Tyr | Phe - Val |
| GABA - Tyr | GABA - Val | GABA - βAla | GABA - βAla | Phg - Tyr | Phg - Val |
| EACA - Tyr | EACA - Val | EACA - βAla | EACA - βAla | Pip - Tyr | Pip - Val |
| K[TFA] - Tyr | K[TFA] - Val | K[TFA] - βAla | K[TFA] - βAla | Pmp - Tyr | Pmp - Val |
| 1-Nal - Tyr | 1-Nal - Val | 1-Nal - βAla | 1-Nal - βAla | Pro - Tyr | Pro - Val |
| 2-Nal - Tyr | 2-Nal - Val | 2-Nal - βAla | 2-Nal - βAla | Qal - Tyr | Qal - Val |
| 3Hyp - Tyr | 3Hyp - Val | 3Hyp - βAla | 3Hyp - βAla | Qua - Tyr | Qua - Val |
| 3-Pal - Tyr | 3-Pal - Val | 3-Pal - βAla | 3-Pal - βAla | Sar - Tyr | Sar - Val |
| 4Abu - Tyr | 4Abu - Val | 4Abu - βAla | 4Abu - βAla | Ser - Tyr | Ser - Val |
| 4Hyp - Tyr | 4Hyp - Val | 4Hyp - βAla | 4Hyp - βAla | Thi - Tyr | Thi - Val |
| A2bu - Tyr | A2bu - Val | A2bu - βAla | A2bu - βAla | Thr - Tyr | Thr - Val |
| A2pr - Tyr | A2pr - Val | A2pr - βAla | A2pr - βAla | Tic - Tyr | Tic - Val |
| Aad - Tyr | Aad - Val | Aad - βAla | Aad - βAla | Trp - Tyr | Trp - Val |
| aAhx - Tyr | aAhx - Val | aAhx - βAla | aAhx - βAla | Tyr - Tyr | Tyr - Val |
| Abo - Tyr | Abo - Val | Abo - βAla | Abo - βAla | Val - Tyr | Val - Val |
| Abu - Tyr | Abu - Val | Abu - βAla | Abu - βAla | βAla - Tyr | βAla - Val |
| ACCA - Tyr | ACCA - Val | ACCA - βAla | ACCA - βAla | Phe - βAla | Phe - βAla |
| Acp - Tyr | Acp - Val | Acp - βAla | Acp - βAla | Phg - βAla | Phg - βAla |
| Ahe - Tyr | Ahe - Val | Ahe - βAla | Ahe - βAla | Pip - βAla | Pip - βAla |
| Ahx - Tyr | Ahx - Val | Ahx - βAla | Ahx - βAla | Pmp - βAla | Pmp - βAla |
| aHyl - Tyr | aHyl - Val | aHyl - βAla | aHyl - βAla | Pro - βAla | Pro - βAla |
| Aib - Tyr | Aib - Val | Aib - βAla | Aib - βAla | Qal - βAla | Qal - βAla |
| Aib - Tyr | Aib - Val | Aib - βAla | Aib - βAla | Qua - βAla | Qua - βAla |
| Aic - Tyr | Aic - Val | Aic - βAla | Aic - βAla | Sar - βAla | Sar - βAla |
| aIle - Tyr | aIle - Val | aIle - βAla | aIle - βAla | Ser - βAla | Ser - βAla |
| Ala - Tyr | Ala - Val | Ala - βAla | Ala - βAla | Thi - βAla | Thi - βAla |
| Apm - Tyr | Apm - Val | Apm - βAla | Apm - βAla | Thr - βAla | Thr - βAla |
| Arg - Tyr | Arg - Val | Arg - βAla | Arg - βAla | Tic - βAla | Tic - βAla |
| Asn - Tyr | Asn - Val | Asn - βAla | Asn - βAla | Trp - βAla | Trp - βAla |
| Asp - Tyr | Asp - Val | Asp - βAla | Asp - βAla | Tyr - βAla | Tyr - βAla |
| Atc - Tyr | Atc - Val | Atc - βAla | Atc - βAla | Val - βAla | Val - βAla |
| Ava - Tyr | Ava - Val | Ava - βAla | Ava - βAla | βAla - βAla | βAla - βAla |
| Aze - Tyr | Aze - Val | Aze - βAla | Aze - βAla | Leu - Tyr | Leu - Val |
| bAad - Tyr | bAad - Val | bAad - βAla | bAad - βAla | Lys - Tyr | Lys - Val |

TABLE 5-continued

Illustrative combinations for $X^2 - X^3$ and/or $X^3 - X^4$.

| I-P | P-D | P-F | F-H | V-A | A-G |
|---|---|---|---|---|---|
| bAib - Tyr | bAib - Val | bAib - βAla | bAib - βAla | MeGly - Tyr | MeGly - Val |
| bAla - Tyr | bAla - Val | bAla - βAla | bAla - βAla | MeIle - Tyr | MeIle - Val |
| Cha - Tyr | Cha - Val | Cha - βAla | Cha - βAla | MeLys - Tyr | MeLys - Val |
| Cpg - Tyr | Cpg - Val | Cpg - βAla | Cpg - βAla | Met - Tyr | Met - Val |
| Cpp - Tyr | Cpp - Val | Cpp - βAla | Cpp - βAla | Met (O) - Tyr | Met (O) - Val |
| cPzACAla - Tyr | cPzACAla - Val | cPzACAla - βAla | cPzACAla - βAla | Met (((S—Me))) - Tyr | Met (((S—Me))) - Val |
| Cys - Tyr | Cys - Val | Cys - βAla | Cys - βAla | MeVal - Tyr | MeVal - Val |
| Dap - Tyr | Dap - Val | Dap - βAla | Dap - βAla | Mpt - Tyr | Mpt - Val |
| Dbf - Tyr | Dbf - Val | Dbf - βAla | Dbf - βAla | Nap - Tyr | Nap - Val |
| Dbu - Tyr | Dbu - Val | Dbu - βAla | Dbu - βAla | Nle - Tyr | Nle - Val |
| Des - Tyr | Des - Val | Des - βAla | Des - βAla | Nva - Tyr | Nva - Val |
| Dip - Tyr | Dip - Val | Dip - βAla | Dip - βAla | Oic - Tyr | Oic - Val |
| Dph - Tyr | Dph - Val | Dph - βAla | Dph - βAla | Opt - Tyr | Opt - Val |
| Dpm - Tyr | Dpm - Val | Dpm - βAla | Dpm - βAla | Orn - Tyr | Orn - Val |
| Dpr - Tyr | Dpr - Val | Dpr - βAla | Dpr - βAla | Pen - Tyr | Pen - Val |
| EtAsn - Tyr | EtAsn - Val | EtAsn - βAla | EtAsn - βAla | Leu - βAla | Leu - βAla |
| EtGly - Tyr | EtGly - Val | EtGly - βAla | EtGly - βAla | Lys - βAla | Lys - βAla |
| gAbu - Tyr | gAbu - Val | gAbu - βAla | gAbu - βAla | MeGly - βAla | MeGly - βAla |
| Gln - Tyr | Gln - Val | Gln - βAla | Gln - βAla | MeIle - βAla | MeIle - βAla |
| Glu - Tyr | Glu - Val | Glu - βAla | Glu - βAla | MeLys - βAla | MeLys - βAla |
| Gly - Tyr | Gly - Val | Gly - βAla | Gly - βAla | Met - βAla | Met - βAla |
| Gly(Ph) - Tyr | Gly(Ph) - Val | Gly(Ph) - βAla | Gly(Ph) - βAla | Met (O) - βAla | Met (O) - βAla |
| Har - Tyr | Har - Val | Har - βAla | Har - βAla | Met (((S—Me))) - βAla | Met (((S—Me))) - βAla |
| Hcy - Tyr | Hcy - Val | Hcy - βAla | Hcy - βAla | MeVal - βAla | MeVal - βAla |
| Hib - Tyr | Hib - Val | Hib - βAla | Hib - βAla | Mpt - βAla | Mpt - βAla |
| His - Tyr | His - Val | His - βAla | His - βAla | Nap - βAla | Nap - βAla |
| Hse - Tyr | Hse - Val | Hse - βAla | Hse - βAla | Nle - βAla | Nle - βAla |
| Hyl - Tyr | Hyl - Val | Hyl - βAla | Hyl - βAla | Nva - βAla | Nva - βAla |
| Hyp - Tyr | Hyp - Val | Hyp - βAla | Hyp - βAla | Oic - βAla | Oic - βAla |
| Ide - Tyr | Ide - Val | Ide - βAla | Ide - βAla | Opt - βAla | Opt - βAla |
| Ile - Tyr | Ile - Val | Ile - βAla | Ile - βAla | Orn - βAla | Orn - βAla |
| Iva - Tyr | Iva - Val | Iva - βAla | Iva - βAla | Pen - βAla | Pen - βAla |

As indicated above, the "loop peptides" described above can form a component t of a larger peptide, preferably a larger peptide that is not naturally occurring (e.g., not netrin-1). In various embodiments the larger peptide can comprise a multitude of the same loop peptide or can comprise different loop peptides.

In certain embodiments loop peptide concatamers are contemplated. The concatamers comprise a plurality of loop peptides that can be the same or different loop peptides. In certain embodiments the loop peptides are joined directly together while in other peptides the loop peptides are joined by linker regions. In certain embodiments the loop peptides are chemically conjugated while in other embodiments they are joined by peptide linkers to form a single fusion peptide.

In certain embodiments, the loop peptide(s) are attached to another molecule to provide cell- or tissue-preferential targeting and/or to facilitate passage across the blood-brain barrier. For example, moieties that can selectively penetrate the blood-brain barrier (BBB) include, but are not limited to moieties that comprise a receptor binding domain from ApoB, ApoE, aprotinin, lipoprotein lipase, PAI-1, pseudomonas exotoxin A, transferrin, α2-macroglobulin, insulin-like growth factor, insulin, or a functional fragment thereof (see, e.g., U.S. Patent Publications 2005/0100986 and 2006/0198833).

For example, as described in US Patent Publication 2006/0198833, ApoB and the ApoB polypeptide fragments described therein bind to the BBB-receptors megalin and low-density lipoprotein receptor (LDLR). ApoE and the ApoE polypeptide fragments described therein bind to megalin, apolipoprotein E receptor 2, low-density lipoprotein related receptor (LRP), very-low density lipoprotein receptor (VLDL-R) and LDLR. Aprotinin, lipoprotein lipase, α2-macroglobulin (α2M), PAI-I and pseudomonas exotoxin A and their respective polypeptide fragments described therein bind to LDLR. A specific example of an ApoB fragment constituting a BBB-receptor binding domain is the amino acid sequence PSSVIDALQYKLEGT-TRLTRKRGLKLATALSLSNKFVEGSPS (SEQ ID NO:4). A specific example of an ApoE fragment constituting a BBB-receptor binding domain is the amino acid sequence VDRVRLASHLRKLRKRLLR (SEQ ID NO:5). Both of these BBB-receptor binding domains selectively bind, for example, LDLR. A specific example of an aprotinin fragment constituting a BBB-receptor binding domain is the amino acid sequence RRPDFCLEPPYTGPCKARIIRYFYN AKAGLCQTFVYGGCRA KRNNFKSAEDCMRTCGG A (SEQ ID NO:6), which binds the megalin receptor. Accordingly, functional fragments of BBB-receptor binding polypeptides or domains also can be used as a targeting moiety for the CNS targeting.

Other polypeptides recognized by a BBB-receptor that can be used as a targeting component of a chimeric CNS targeted loop peptide include, for example, transferrin, angiotensin II, arginine vasopressin, atrial natriuretc peptide, brakykinin, brain natriuretic peptide, endothelin, insulin like growth factors, insulin, neuropeptide Y, oxytocin, pancreatic polupeptide, prolactin, somatostatin, substance P and vasoactive intestinal polypeptide as well as those amino acid sequences and their corresponding parent polypeptides listed in FIG. 1 of US Patent Publication 2006/0198833 which are incorporated herein by reference. Additionally, the BBB-receptor binding domain of these polypeptides also can be removed from the parent polypeptide framework and employed as a CNS targeting moieties. A description of the receptor binding activity of the above described polypeptides can be found described in, for example, Moos and Morgan (2000) *Cell. & Mol. Neurobiol.,* 20: 77-95; Nielsen et al. (1996) *J. Biol. Chem.,* 271: 12909-12912; Kounnas et al. (1992) *J. Biol. Chem.,* 267: 12420-12423; Moestrup et al. (1995) *J. Clin. Invest.,* 96: 1404-1413; Norris et al. (1990) *Biol. Chem. Hoppe Seyler,* 371 Suppl:37-42; and Ermisch et al. (1993) *Phys. Revs.* 73: 480-527.

Polypeptides, or their functional fragments, that are known to cross the BBB can similarly be employed as a targeting component for directing loop peptide(s) described herein to the brain. Translocation of such polypeptides across the BBB indicates the existence of a cognate receptor binding partner to the translocated ligand. Accordingly, these polypeptides or their BBB-receptor binding domains, as well as other polypeptides known in the art which can cross the BBB, can be employed as a BBB-receptor binding domain (targeting moiety) in chimeric moieties comprising one or more loop peptides described herein even in the absence of an identified cognate receptor. Specific examples of such BBB-translocating polypeptides include a MSH, adrenocorticotropin analogues, β casomorphin, β endorphin and analogues, bovine adrenal medulla dodecapeptide, corticotropin releasing hormone, cyclo Leu Gly (diketopiperazine), D Ala peptide T amide, delta sleep inducing peptide, encaphalins and analogues, FMRF, gastrin releasing peptide, glucagon, growth hormone releasing hormone, insulin, luteinizing hormone releasing hormone (GnRH), oxytocin, Pro Leu Gly (MIF 1 MSH release inhibiting factor), prolactin, somatostatin and analogues, substance P, thyrotropin releasing hormone (TRH), Tyr MIF 1. A description of the BBB translocation activity of these polypeptides can be found for example, in Banks and Kastin "Bidirectional passage of peptides across the blood brain barrier." In Circumventricular Organs and Brain Fluid Environment; A. Ermisch, R. Landgraf & H J. Ruhle, Eds. *Prog. Brain Res.* 91:139-148 (1992), and Begley, D. J., "Peptides and the blood brain barrier." In Handbook of Experimental Pharmacology: Physiology and Pharmacology of the Blood Brain Barrier. M. W. B. Bradbury, Ed. Vol. 103:151-203. Springer, Berlin, (1992).

Those skilled in the art will know, or can determine, which amino acid residues of a BBB-receptor binding polypeptide constitute a functional fragment sufficient to selectively bind a BBB-receptor. For example, it is routine to make and test successively smaller polypeptide fragments, either recombinantly or chemically, and test them for binding activity. Therefore, any of the BBB-receptor binding polypeptides described above, or portions thereof corresponding to a BBB-receptor binding domain, can be used as a CNS targeting component in a chimeric loop peptide/targeting moiety construct.

In certain embodiments, the loop peptide(s) are chemically conjugated to the BBB targeting moiety. In other embodiments, the loop peptides are expressed as a fusion protein either directly attached to the targeting moiety or through a peptide linker (e.g., $(Gly_4Ser)_3$, $Gly_{6-15}$, etc.)

Peptide Production.

The peptides (e.g., loop peptides) described herein or peptide analogs thereof can be prepared using virtually any technique known to one of ordinary skill in the art for the preparation of peptides. For example, in certain embodiments, the loop peptides can be prepared using step-wise solution or solid phase peptide syntheses, or recombinant DNA techniques, or the equivalents thereof.

Chemical Synthesis

The loop peptides described herein having either the D- or L-configuration (or combinations of D and L amino acids) can be readily synthesized by automated solid phase procedures well known in the art. Suitable syntheses can be performed, for example, by utilizing "T-boc" or "F-moc" procedures. Techniques and procedures for solid phase synthesis are described in Solid Phase *Peptide Synthesis*: A Practical Approach, by E. Atherton and R. C. Sheppard, published by IRL, Oxford University Press, 1989. See also, Stewart et al., Solid-Phase *Peptide Synthesis*, W.H. Freeman Co., San Francisco, Calif. (1969); Merrifield (1963) *J. Am. Chem. Soc.,* 85: 2149-2154, and the like. In vitro protein synthesis may be performed using manual techniques or by automation. Automated synthesis may be accomplished, for instance, using an Applied Biosystems Peptide Synthesizer (Foster City, Calif.) using manufacturer's instructions. In addition custom peptides are available from a number of custom peptide synthesis services (see, e.g., Neo Bioscience, Cambridge, Mass.: GenScript, Piscataway, N.J.; Thermo Scientific, Inc., Huntsville, Ala.; California Peptide Research, Inc., Napa, Calif.; Celtek Peptides, Nashville Tenn.; and the like).

Recombinant Synthesis

In certain embodiments the loop peptides can be synthesized using conventional recombinant genetic engineering techniques. For recombinant production, a polynucleotide sequence encoding the loop peptide(s) is inserted into an appropriate expression vehicle. Typical expression vehicles comprise a vector that contains the necessary elements for the transcription and translation of the inserted coding sequence, or in the case of an RNA viral vector, the necessary elements for replication and translation. The expression vehicle is then transfected into a suitable target cell which expresses the desired peptide(s). Depending on the expression system used, the expressed peptide is then isolated by procedures well-established in the art. Methods for recombinant protein and peptide production are well known in the art (see, e.g., Sambrook et al. (ed.), Molecular Cloning: A Laboratory Manual, 2.sup. nd ed., vol. 1-3, Cold Spring Harbor Laboratory Press, Cold Spring Harbor, N.Y., 1989, Ch. 17 and Ausubel et al. Short Protocols in Molecular Biology, 4.sup. th ed., John Wiley & Sons, Inc., 1999).

A variety of host-expression vector systems can be utilized to express the peptides described herein. These include, but are not limited to, microorganisms such as bacteria transformed with recombinant bacteriophage DNA or plasmid (cosmid, etc.) DNA expression vectors containing an appropriate coding sequence; yeast or filamentous fungi transformed with recombinant yeast or fungi expression vectors containing an appropriate coding sequence; insect cell systems infected with recombinant virus expression vectors (e.g., baculovirus) containing an appropriate coding sequence; plant cell systems infected with recombinant virus expression vectors (e.g., cauliflower mosaic virus (CaMV) or tobacco mosaic virus (TMV)) or transformed with recombinant plasmid expression vectors (e.g., Ti plasmid) containing an appropriate coding sequence; or animal cell systems.

The expression elements of the expression systems vary in their strength and specificities. Depending on the host/vector system utilized, any of a number of suitable transcription and translation elements, including constitutive and inducible promoters, can be used in the expression vector. For example, when cloning in bacterial systems, inducible promoters such as pL of bacteriophage lamda, plac, ptrp, ptac (ptrp-lac hybrid promoter) and the like can be used. When cloning in insect cell systems, promoters such as the baculovirus polyhedron promoter can be used. When cloning in plant cell systems, promoters derived from the genome of plant cells (e.g., heat shock promoters, the promoter for the small subunit of RUBISCO, the promoter for the chlorophyll a/b binding protein) or from plant viruses (e.g., the 35S RNA promoter of CaMV, the coat protein promoter of TMV) can be used. When cloning in mammalian cell systems, promoters derived from the genome of mammalian cells (e.g., metallothionein promoter) or from mammalian viruses (e.g., the adenovirus late promoter, the vaccinia virus 7.5 K promoter) can be used.

Purification

In certain embodiments the loop peptides described herein (or concatamers thereof) can be purified by many techniques well known in the art, such as reverse phase chromatography, high performance liquid chromatography, ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art.

Peptide Cyclization.

In various embodiments, the peptides described herein can be cyclized (cyclopeptides). Cyclopeptides, as contemplated herein, include head/tail, head/side chain, tail/side chain, and side chain/side chain cyclized peptides. In addition, peptides contemplated herein include homodet, containing only peptide bonds, and heterodet containing in addition disulfide, ester, thioester-bonds, or other bonds.

In various embodiments cyclization can be achieved via direct coupling of the N- and C-terminus to form a peptide (or other) bond, but can also occur via the amino acid side chains. Furthermore it can be based on the use of other functional groups, including but not limited to amino, hydroxy, sulfhydryl, halogen, sulfonyl, carboxy, and thiocarboxy. These groups can be located at the amino acid side chains or be attached to their N- or C-terminus.

Cyclic peptides and depsipeptides (heterodetic peptides that include ester (depside) bonds as part of their backbone) have been well characterized and show a wide spectrum of biological activity. The reduction in conformational freedom brought about by cyclization often results in higher receptor-binding affinities. Frequently in these cyclic compounds, extra conformational restrictions are also built in, such as the use of D- and N-alkylated-amino acids, α,β-dehydro amino acids or α,α-disubstituted amino acid residues.

Methods of forming disulfide linkages in peptides are well known to those of skill in the art (see, e.g., Eichler and Houghten (1997) Protein Pept. Lett. 4: 157-164).

Reference may also be made to Marlowe (1993) *Biorg. Med. Chem. Lett.* 3: 437-44 who describes peptide cyclization on TFA resin using trimethylsilyl (TMSE) ester as an orthogonal protecting group; Pallin and Tam (1995) *J. Chem. Soc. Chem. Comm.* 2021-2022) who describe the cyclization of unprotected peptides in aqueous solution by oxime formation; Algin et al. (1994) *Tetrahedron Lett.* 35: 9633-9636 who disclose solid-phase synthesis of head-to-tail cyclic peptides via lysine side-chain anchoring; Kates et al. (1993) *Tetrahedron Lett.* 34: 1549-1552 who describe the production of head-to-tail cyclic peptides by three-dimensional solid phase strategy; Tumelty et al. (1994) *J. Chem. Soc. Chem. Comm.* 1067-1068, who describe the synthesis of cyclic peptides from an immobilized activated intermediate, where activation of the immobilized peptide is carried out with N-protecting group intact and subsequent removal leading to cyclization; McMurray et al. (1994) *Peptide Res.* 7: 195-206) who disclose head-to-tail cyclization of peptides attached to insoluble supports by means of the side chains of aspartic and glutamic acid; Hruby et al. (1994) *Reactive Polymers* 22: 231-241) who teach an alternate method for cyclizing peptides via solid supports; and Schmidt and Langer (1997) *J. Peptide Res.* 49: 67-73, who disclose a method for synthesizing cyclotetrapeptides and cyclopentapeptides.

These methods of peptide cyclization are illustrative and non-limiting. Using the teaching provide herein, other cyclization methods will be available to one of skill in the art.

Protecting Groups.

While the various peptides (e.g., loop peptides) described herein may be shown with no protecting groups, in certain embodiments they can bear one, two, three, four, or more protecting groups. In various embodiments, the protecting groups can be coupled to the C- and/or N-terminus of the peptide(s) and/or to one or more internal residues comprising the peptide(s) (e.g., one or more R-groups on the constituent amino acids can be blocked). Thus, for example, in certain embodiments, any of the peptides described herein can bear, e.g., an acetyl group protecting the amino terminus and/or an amide group protecting the carboxyl terminus. One example of such a protected peptide is shown by Formulas I or II in the peptide bears an N-terminal dansyl group. Of course, this protecting group can be can be eliminated and/or substituted with another protecting group as described herein.

Without being bound by a particular theory, it was a discovery of this invention that addition of a protecting group, particularly to the carboxyl and in certain embodiments the amino terminus can improve the stability and efficacy of the peptide.

A wide number of protecting groups are suitable for this purpose. Such groups include, but are not limited to acetyl, amide, and alkyl groups with acetyl and alkyl groups being particularly preferred for N-terminal protection and amide groups being preferred for carboxyl terminal protection. In certain particularly preferred embodiments, the protecting groups include, but are not limited to alkyl chains as in fatty acids, propeonyl, formyl, and others. Particularly preferred carboxyl protecting groups include amides, esters, and ether-forming protecting groups. In one preferred embodiment, an acetyl group is used to protect the amino terminus and an amide group is used to protect the carboxyl terminus. These blocking groups enhance the helix-forming tendencies of the peptides. Certain particularly preferred blocking groups include alkyl groups of various lengths, e.g., groups having the formula: $CH_3-(CH_2)_n-CO-$ where n ranges from about 1 to about 20, preferably from about 1 to about 16 or 18, more preferably from about 3 to about 13, and most preferably from about 3 to about 10.

In certain embodiments, the protecting groups include, but are not limited to alkyl chains as in fatty acids, propeonyl, formyl, and others. Particularly preferred carboxyl protecting groups include amides, esters, and ether-forming protecting groups. In one embodiment, an acetyl group is used to protect the amino terminus and/or an amino group is used to protect the carboxyl terminus (i.e., amidated carboxyl terminus). In certain embodiments blocking groups include alkyl groups of various lengths, e.g., groups having the formula: $CH_3-(CH_2)_n-CO-$ where n ranges from about 3 to about 20, preferably from about 3 to about 16, more preferably from about 3 to about 13, and most preferably from about 3 to about 10.

Other protecting groups include, but are not limited to Fmoc, t-butoxycarbonyl (t-BOC), 9-fluoreneacetyl group, 1-fluorenecarboxylic group, 9-florenecarboxylic group, 9-fluorenone-1-carboxylic group, benzyloxycarbonyl, Xanthyl (Xan), Trityl (Trt), 4-methyltrityl (Mtt), 4-methoxytrityl (Mmt), 4-methoxy-2,3,6-trimethyl-benzenesulphonyl (Mtr), Mesitylene-2-sulphonyl (Mts), 4,4-dimethoxybenzhydryl (Mbh), Tosyl (Tos), 2,2,5,7,8-pentamethyl chroman-6-sulphonyl (Pmc), 4-methylbenzyl (MeBzl), 4-methoxybenzyl (MeOBzl), Benzyloxy (BzlO), Benzyl (Bzl), Benzoyl (Bz), 3-nitro-2-pyridinesulphenyl (Npys), 1-(4,4-dimentyl-2,6-diaxocyclohexylidene)ethyl (Dde), 2,6-dichlorobenzyl (2,6-DiCl-Bzl), 2-chlorobenzyloxycarbonyl (2-Cl—Z), 2-bromobenzyloxycarbonyl (2-Br—Z), Benzyloxymethyl (Bom), cyclohexyloxy (cHxO), t-butoxymethyl (Bum), t-butoxy (tBuO), t-Butyl (tBu), Acetyl (Ac), and Trifluoroacetyl (TFA).

Protecting/blocking groups are well known to those of skill as are methods of coupling such groups to the appropriate residue(s) comprising the peptides of this invention (see, e.g., Greene et al., (1991) *Protective Groups in Organic Synthesis,* 2nd ed., John Wiley & Sons, Inc. Somerset, N.J.). In illustrative embodiment, for example, acetylation is accomplished during the synthesis when the peptide is on the resin using acetic anhydride. Amide protection can be achieved by the selection of a proper resin for the synthesis. For example, a rink amide resin can be used. After the completion of the synthesis, the semipermanent protecting groups on acidic bifunctional amino acids such as Asp and Glu and basic amino acid Lys, hydroxyl of Tyr are all simultaneously removed. The peptides released from such a resin using acidic treatment comes out with the n-terminal protected as acetyl and the carboxyl protected as $NH_2$ and with the simultaneous removal of all of the other protecting groups.

Where amino acid sequences are disclosed herein, amino acid sequences comprising, one or more protecting groups, e.g., as described above (or any other commercially available protecting groups for amino acids used, e.g., in boc or fmoc peptide synthesis) are also contemplated.

Screening for Peptide Activity.

Various peptides described herein can alters APP signaling by modulating ERK phosphorylation and/or switch APP processing from aberrant to normal.

Methods of assaying agents for their effect on ERK phosphorylation are well known to those of skill in the art (see, e.g., Yau and Zahradka (1997) *Mol Cell Biochem* 172: 59-66; Gorenne et al. (1998) *Am J Physiol Heart Circ Physiol* 275: H131-H138; and the like). Such assays include, for example, Western Blots and various antibody-based assays using for example anti-active ERK antibodies. One commercially available ERK phosphorylation assay is the p-ERK SUREFIRE® assy from TR BioSciences. This assay measures the phosphorylation of endogenous cellular ERK1/2 at Thr202/Tyr204 by MEK1/2. This assay is a homogenous assay providing short assay times and is well suited for high throughput screening. In one illustrative embodiment, the SUREFIRE® system is used to measure ERK phosphorylation in H4-APP cells exposed to the agent(s) of interest.

In certain illustrative embodiments, the sAPPα level can be measured using the AlphaLisa assay using the PerkinElmer (PE) AlphaLisa assay (cat#AL203C for sAPPα). The affect of the peptides on Aβ can be measured using the PerkinElmer (PE) AlphaLisa assay (Cat#AL202C for $A\beta_{42}$) and the PerkinElmer Enspire AlphaLisa reader.

Similarly, assays for the effect of an agent (e.g., a loop peptide) on APP screening are also know to those of skill in the art. For example, in one embodiment the effect of the peptide(s) or chimeric constructs described herein on APP processing can be evaluated in hAPP transgenic mice that model of Alzheimer's disease (von Rotz et al. (2004) *Cell Sci.,* 117: 4435-4448). The assay is also illustrated in PCT Publication WO 2007/120912. Whole brain slice cultures from PDAPP transgenic and non-transgenic littermates are treated with vehicle or with peptide to be tested and evaluated, e.g., by ELISA assay for the production of Aβ1-40 and/or Aβ1-42. In this regard, it is noted that assay kits for the detection and/or quantitation of Aβ1-40 and Aβ1-42 are commercially available. Thus, for example, an ALPHALISA® Human Amyloid β1-42 and Human Amyloid β1-40 research immunoassay kits are available from Perkin Elmer (Waltham, Mass.).

All of these assays are amendable to high-throughput methodologies permitting the testing/screening of thousands of peptides or chimeric constructs in a relatively short time.

Pharmaceutical Formulations and Administration.

Pharmaceutical Formulations.

In certain embodiments, the loop peptides and/or the chimeric constructs (e.g., targeting moieties attached to loop peptide(s), loop peptides attached to detectable label(s), etc.) are administered to a mammal in need thereof, to a cell, to a tissue, to a composition (e.g., a food, etc.). In various embodiments, the composition can be administered to alter APP signaling and/or to switch APP processing from aberrant to normal. In various embodiments the compositions can be administered as a prophylactic and/or therapeutic to mitigate one or more symptoms or to inhibit the onset, progression or severity of a pathology characterized by amyloid plaque formation (e.g., MCI, Alzheimer's disease, etc.).

These active agents (loop peptides and/or chimeric moieties) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry: Reactions, Mechanisms and Structure,* 4th Ed. N.Y. Wiley-Interscience.

Methods of formulating such derivatives are known to those of skill in the art. For example, the disulfide salts of a number of delivery agents are described in PCT Publication WO 2000/059863. Similarly, acid salts of therapeutic peptides, peptoids, or other mimetics, and can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. In certain embodiments basic salts include alkali metal salts, e.g., the sodium salt, and copper salts.

In various embodiments preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein are useful for parenteral, topical, oral, nasal (or otherwise inhaled), rectal, or local administration, such as by aerosol or transdermally, for detection and/or quantification, and or localization, and/or prophylactic and/or therapeutic treatment of infection (e.g., microbial infection). The compositions can be administered in a variety of unit dosage forms depending upon the method of administration. Suitable unit dosage forms, include, but are not limited to powders, tablets, pills, capsules, lozenges, suppositories, patches, nasal sprays, injectables, implantable sustained-release formulations, lipid complexes, etc.

The active agents (e.g., t loop peptides and/or chimeric constructs) described herein can also be combined with a pharmaceutically acceptable carrier (excipient) to form a pharmacological composition. In certain embodiments, pharmaceutically acceptable carriers include those approved by a regulatory agency of the Federal or a state government or listed in the U.S. Pharmacopeia or other generally recognized pharmacopeia for use in/on animals, and more particularly in/on humans. A "carrier" refers to, for example, a diluent, adjuvant, excipient, auxiliary agent or vehicle with which an active agent of the present invention is administered.

Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disintegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethylcellulose, polyvinylpyrrolidone, hydroxypropylcellulose, cyclodextrin, etc.), and an optional lubricant (e.g., talc, magnesium stearate, polyethylene glycol 6000, etc.), for instance, are added to the active component or components (e.g., active) and the resulting composition is compressed. Where necessary the compressed product is coated, e.g., known methods for masking the taste or for enteric dissolution or sustained release. Suitable coating materials include, but are not limited to ethyl-cellulose, hydroxymethylcellulose, polyoxyethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

Administration.

In certain therapeutic applications, the compositions described herein are administered, e.g., parenterally administered or administered to the oral or nasal cavity, to a patient suffering from or at risk for a pathology characterized by amyloid plaque formation in an amount sufficient to prevent and/or cure and/or at least partially prevent or arrest the disease and/or its complications. An amount adequate to accomplish this is defined as a "therapeutically effective dose." Amounts effective for this use will depend upon the severity of the disease and the general state of the patient's health. Single or multiple administrations of the compositions may be administered depending on the dosage and frequency as required and tolerated by the patient. In any event, the composition should provide a sufficient quantity of the active agents of the formulations of this invention to effectively treat (ameliorate one or more symptoms in) the patient or to prevent or slow the onset or progression of the disease.

Thus, a therapeutically or prophylactically effective amount refers to an amount of such a molecule required to effect a beneficial change in a clinical symptom, physiological state or biochemical activity targeted by a loop polypeptide or chimeric construct described herein. For example, in certain embodiments an effective is an amount sufficient to decrease the extent, amount or rate of progression of plaque formation associated with Aβ peptide accumulation. The dosage of a loop peptide or chimeric construct that is therapeutically effective will depend, for example, on the severity of the symptoms to be treated, the route and form of administration, the potency and bio-active half-life of the molecule being administered, the weight and condition of the subject, and previous or concurrent therapies.

The appropriate amount considered to be an effective dose for a particular application of the method can be determined by those skilled in the art, using the teachings and guidance provided herein. For example, the amount can be extrapolated from in vitro or in vivo assays or results from clinical trials employing related or different therapeutic molecules or treatment regimes. The required dosage will vary with the particular treatment and with the duration of desired treatment; however, it is anticipated that dosages between about 1 or 10 micrograms and about 1, or 10, or 50, or 100 milligram per kilogram of body weight per day will be used for therapeutic treatment. It may be particularly advantageous to administer such a substance in depot or long-lasting form as discussed herein. In certain embodiments a therapeutically effective amount is typically an amount of a substance that, when administered in a physiologically acceptable composition, is sufficient to achieve a plasma concentration of from about 0.1 pg/ml to about 100 pg/ml, preferably from about 1.0 pg/ml to about 50 pg/ml, more preferably at least about 2 pg/ml and usually 5 to 10 pg/ml.

The substances useful for practicing the methods of the invention can be formulated and administered by those skilled in the art in a manner and in an amount appropriate for the condition to be treated; the rate or amount of inflammation; the weight, gender, age and health of the individual; the biochemical nature, bioactivity, bioavailability and side effects of the particular compound; and in a manner compatible with concurrent treatment regimens. An appropriate amount and formulation for decreasing the severity of a neurodegenerative condition associated with beta amyloid peptide production and amyloid plaque formation in humans can be extrapolated from credible animal models known in the art of the particular disorder. It is understood, that the dosage of a therapeutic substance has to be adjusted based on the binding affinity of the substance, such that a lower dose of a substance exhibiting significantly higher binding affinity can be administered compared to the dosage necessary for a substance with lower binding affinity.

The total amount of a substance can be administered as a single dose or by infusion over a relatively short period of time, or can be administered in multiple doses administered over a more prolonged period of time. Such considerations will depend on a variety of case-specific factors such as, for example, whether the disease category is characterized by acute episodes or gradual or chronic deterioration. For an individual affected with chronic deterioration, for example, as associated with neuroinflammatory disorder such as MS, the substance can be administered in a slow-release matrice, which can be implanted for systemic delivery or at the site of the target tissue. Contemplated matrices useful for controlled release of therapeutic compounds are well known in the art, and include materials such as DEPOFOAM™, biopolymers, micropumps, and the like.

The loop peptides and chimeric moieties described herein can be administered to a subject by any number of routes known in the art including, for example, systemically, such as intravenously or intraarterially. A therapeutic substance can be provided in the form of isolated and substantially purified polypetides and/or chimeric moieties in pharmaceutically acceptable formulations using formulation methods known to those of ordinary skill in the art.

In view of the fact that beta-amyloid plaques form in the Central Nervous System (CNS), it is understood that formulations capable of crossing the blood-brain barrier are particularly preferred embodiments for administration of a loop peptide or chimeric moiety described herein. In one illustrative embodiment, the blood-brain barrier is temporarily disrupted and the loop peptide(s) and/or chimeric construct(s) are administered in conjunction with the disruption.

Treatments to selectively increase the permeability of the blood brain barrier include, but are not limited to, the administration of about 1 to about 1000 μg/kg body weight, preferably about 10 to about 100 μg/kg bodyweight, of IGF-I as a bolus injection to a patient about 0.5 to 10 hours, preferably about 1 hour, before administration of the loop peptide(s) and/or chimeric constructs. While not being bound to any specific theory, this treatment can enhance selective endocytosis of large molecules (see, e.g., Carro et al. (2002) *Nature Med.*, 8: 1390-1397).

In addition, polypeptides called receptor mediated permeabilizers (WNW) can be used to increase the permeability of the blood-brain barrier to molecules such as therapeutic or diagnostic substances as described in U.S. Pat. Nos. 5,268, 164; 5,506,206; and 5,686,416. These receptor mediated permeabilizers can be intravenously co-administered to a host with molecules whose desired destination is the cerebrospinal fluid compartment of the brain, for example, in the treatment of a neurodegenerative condition. The permeabilizer polypeptides or conformational analogues thereof allow therapeutic substances to penetrate the blood brain barrier and arrive at their target destination.

Also, even without selective permeabilization with a drug such as IGF-I, the blood brain barrier may be compromised in Alzhemier's disease so that compounds that normally do not enter the brain, or have a saturated uptake, may access the brain more readily.

In certain embodiments, to facilitate crossing the blood-brain barrier, formulations that increase the lipophilicity of the compound are particularly desirable. For example, the neutralizing agent can be incorporated into liposomes (see, e.g., Gregoriadis, Liposome Technology, Vols. I to III, 2nd ed. (CRC Press, Boca Raton Fla. (1993)). Liposomes, that consist of phospholipids or other lipids, are nontoxic, physiologically acceptable and metabolizable carriers that are relatively simple to make and administer.

Therapeutic and/or prophylactic substance(s) substance administered in the methods described herein can also be prepared as nanoparticles. Adsorbing peptide compounds onto the surface of nanoparticles has proven effective in delivering peptide drugs to the CNS (see e.g., Kreuter et al. (1995) *Brain Res.*, 674: 171-174). Illustrative nanoparticles include, but are not limited to colloidal polymer particles of poly-butylcyanoacrylate with a therapeutic substance adsorbed onto the surface and then coated with polysorbate 80.

Image-guided ultrasound delivery of loop peptide and/or chimeric constructs as described herein to selected locations in the brain can be utilized as described in U.S. Pat. No. 5,752,515. Briefly, to deliver a therapeutic substance past the blood-brain barrier a selected location in the brain is targeted and ultrasound used to induce a change detectable by imaging in the central nervous system (CNS) tissues and/or fluids at that location. At least a portion of the brain in the vicinity of the selected location is imaged, for example, via magnetic resonance imaging (MRI), to confirm the location of the change. A therapeutic substance administered into the patient's bloodstream can be delivered to the confirmed location by applying ultrasound to effect opening of the blood-brain barrier at that location and, thereby, to induce uptake of the substance.

In certain embodiments direct delivery of loop peptides to the brain can be achieved using a pump with a catheter that allows for intraceberalventricular (ICV) or intraparenchymal delivery.

In embodiments where the loop peptide(s) are conjugated to a second polypeptide, the second peptide or protein can be therapeutic or can be a peptide capable of absorptive-mediated or receptor-mediated transcytosis through the subject's blood brain barrier (e.g., as described above). In another embodiment, the loop peptide(s) and/or chimeric constructs are administered through an artificial LDL particle comprising an outer phospholipid monolayer and a solid lipid core, wherein the outer phospholipid monolayer comprises one or more apolipoproteins and the solid lipid core contains the loop peptide(s) and/or chimeric construct(s). In a further embodiment, the loop peptide and/or chimeric construct is bound to a nanoparticle comprising a hydrophilic protein to which apolipoprotein E is coupled or bound. or co-administered with an antiglucortoid drug in a sufficient amount to increase permeability of the subject's blood brain barrier.

In other embodiments, the loop peptide(s) and/or chimeric construct(s) are chemically modified for enhanced transmembrane transport, for example, by covalent linking of a fatty acid to the peptide or construct polypeptide or glycosylation of the peptide or construct.

In current treatment regimes for Alzheimer's Disease, more than one compound is often administered to an individual for management of the same or different aspects of the disease. Similarly, a loop peptide and/or chimeric construct described herein can advantageously be formulated with a second therapeutic compound such as an anti-inflammatory compound, immunosuppressive compound or any other compound that manages the same or different aspects of the disease. Such compounds include, for example, cholinesterase inhibitors such as RAZADYNE® (formerly known as REMINYL®) (galantamine), EXELON® (rivastigmine), ARICEPT® (donepezil), and COGNEX® (tacrine), N-methyl D-aspartate (NMDA) antagonists such as NAMENDA® (memantine); β- or γ-secretase inhibitors; tau phosphorylation inhibitors; Dimebon and those medicines that are administered to control behavioral symptoms of AD such as sleeplessness, agitation, wandering, anxiety, and depression.

Additional medicines can be coadministered with a loop peptide and/or chimeric construct described herein, treat mild cognitive impairment (MCI) associated with early stages of Alzheimer's disease, for example, donepezil (Aricept). The skilled practitioner will be able to select further candidates for coadministration with a loop peptide and/or chimeric construct described herein from the numerous medicines and compounds known in the art as useful in the clinical management of AD and its symptoms including, for example, vitamins E and C; nonsteroidal anti-inflammatory drugs (NSAIDs); antioxidants, *Ginkgo biloba* and estrogen. Contemplated methods also include administering loop peptide(s) and/or chimeric construct(s), in combination with, or in sequence with, such other compounds. Alternatively, combination therapies can consist of fusion proteins, where the therapeutic loop peptide is linked to a heterologous protein. In embodiments where the loop peptide is conjugated to a second polypeptide, the second peptide or protein can be therapeutic or can be a peptide capable of absorptive-mediated or receptor-mediated transcytosis through the subject's blood brain barrier. In certain embodiments chimeric constructs comprising a one or more loop peptides, a second therapeutic moiety, and a BBB targeting moiety are contemplated.

In certain embodiments a loop peptide and/or chimeric construct described herein which effectively reduces or inhibits Aβ peptide production or amyloid plaque formation can also be used to enhance memory function, especially the elderly. A subject can be administered such agents and assayed for improved memory capability While the loop peptide(s) and/or chimeric construct(s) are described with respect to use in humans, they are also suitable for animal, e.g., veterinary use. Thus certain preferred organisms include, but are not limited to humans, non-human primates, canines, equines, felines, porcines, ungulates, largomorphs, and the like.

Combined Treatment Methods and Combined Formulations

In certain instances, one or more of the active agents described above (e.g., netrin loop peptides) are administered in conjunction with one or more additional active agent(s) that are known, or believed, to have utility in the treatment of neurodegenerative diseases including, but not limited to Alzheimer's disease, age-related cognitive impairment, MCI, and the like. The two (or more) agents (e.g., netrin loop peptide(s) and additional agent) can be administered simultaneously or sequentially. When administered sequentially the two agents are typically administered so that both achieve a physiologically relevant concentration and/or effect over a similar time period (e.g., so that both agents are active at some common time).

In certain instances, one or more of the netrin loop peptides described above are administered before the one or more additional active agents or they are administered after the one or more additional active agents. In certain embodiments one or more of the netrin loop peptide(s) are administered simultaneously with one or more additional active agents and in such instances may be formulated as a compound formulation.

Suitable additional active agents include, but are not limited to, Donepezil (e.g., Aricept), Rivastigmine (e.g., EXELON®), Galantamine (e.g., RAZADINE®), Tacrine (e.g., COGNEX®), Memantine (e.g., NAMENDA®), Solanezumab, Bapineuzmab, Alzemed, Flurizan, ELND005, Valproate, Semagacestat, Rosiglitazone, Phenserine, Cernezumab, Dimebon, EGCg, Gammagard, PBT2, PF04360365, NIC5-15, Bryostatin-1, AL-108, Nicotinamide, EHT-0202, BMS708163, NP12, Lithium, ACC001, AN1792, ABT089, NGF, CAD106, AZD3480, SB742457, AD02, Huperzine-A, EVP6124, PRX03140, PUFA, HF02, MEM3454, TTP448, PF-04447943, Ent., GSK933776, MABT5102A, Talsaclidine, UB311, Begacestat, R1450, PF3084014, V950, E2609, MK0752, CTS21166, AZD-3839, LY2886721, CHF5074, anti-inflammatories (e.g., Flurizan (Myriad Genetics), Dapsone, anti-TNF antibodies (e.g., etanercept (Amgen/Pfizer)), and the like), statins (e.g., atorvastatin (LIPITOR®), simvastatin (ZOCOR®, etc.), and the like. In certain embodiments, treatment methods comprising administration of one or more netrin loop peptide(s) described herein in conjunction with any one of the foregoing additional active agents is contemplated. In certain embodiments, treatment methods comprising administration of one or more netrin loop peptide(s) described herein in conjunction with any one or more of the foregoing additional active agents is contemplated.

In certain embodiments, combination formulations comprising one or more netrin loop peptide(s) described herein in combination with any one of the foregoing additional active agents is contemplated. In certain embodiments, combination formulations comprising one or netrin loop peptide(s) described herein in combination with any one or more of the foregoing additional active agents is contemplated.

In certain embodiments, treatment methods comprising administration of one or more netrin loop peptides described herein in conjunction with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the treatment method comprises administration of tropisetron in conjunction with of one or more netrin loop peptides, and the like described herein.

In certain embodiments, treatment methods comprising administration of one or more netrin loop peptides described herein in conjunction with additional therapeutic agents such as tropinol esters and related agents, e.g., as described in PCT Application No: PCT/US2012/049223, filed on Aug. 1, 2012) which is incorporated herein by reference for the compounds described therein) are contemplated.

In certain embodiments, combination formulations comprising administration of one or more netrin loop peptide(s) described herein in combination with additional therapeutic agents such as disulfiram and/or analogues thereof, honokiol and/or analogues thereof, tropisetron and/or analogues thereof, nimetazepam and/or analogues thereof (e.g., as described in U.S. Ser. No. 13/213,960 (U.S. Patent Publication No: US-2012-0071468-A1), and PCT/US2011/048472 (PCT Publication No: WO 2012/024616) which are incorporated herein by reference for the compounds described therein) are contemplated. In certain embodiments the combination formulation comprises tropisetron in combination with of one or more netrin loop peptide(s) described herein Assay Systems to Evaluate APP Processing Without being bound to a particular theory, it is believed that, in certain embodiments, the netrin loop peptide(s) described herein promote processing of APP by the non-amyloidogenic pathway and/or reduce or inhibit processing of APP by the amyloidogenic pathway. In the nonamyloidogeic pathway, APP is first cleaved by α-secretase within the Aβ sequence, releasing the APPsα ectodomain ("sAPPα"). In contrast, the amyloidogenic pathway is initiated when β-secretase cleaves APP at the amino terminus of the Aβ, thereby releasing the APPsβ ectodomain ("sAPPβ"). APP processing by the nonamyloidogenic and amyloidogenic pathways is known in the art and reviewed, e.g., by Xu (2009) *J. Alzheimer's Dis.*, 16(2):211-224 and De Strooper et al., (2010) *Nat Rev Neurol.*, 6(2): 99-107.

One method to evaluate the efficacy of various netrin loop peptide(s) described herein is to determine whether or not the compound(s) in question produce a reduction or elimination in the level of APP processing by the amyloidogenic pathway, e.g., a reduction or elimination in the level of APP processing by β-secretase cleavage. Assays for determining the extent of APP cleavage at the β-secretase cleavage site are well known in the art. Illustrative assays, are described, for example, in U.S. Pat. Nos. 5,744,346 and 5,942,400. Kits for determining the presence and levels in a biological sample of sAPPα and sAPPβ, as well as APPneo and Aβ commercially available, e.g., from PerkinElmer.

Cell Free Assays

Illustrative assays that can be used to evaluate the inhibitory activity of netrin loop peptide(s) described herein are described, for example, in PCT Publication Nos: WO 2000/017369, and WO 2000/003819, and in U.S. Pat. Nos. 5,942,400 and 5,744,346. In certain embodiments, such assays can be performed in cell-free incubations or in cellular incubations using cells expressing an alpha-secretase and/or beta-secretase and an APP substrate having an alpha-secretase and beta-secretase cleavage sites.

One illustrative assay, test the compound(s) of interest utilizing an APP substrate containing alpha-secretase and beta-secretase cleavage sites of APP, for example, a complete APP or variant, an APP fragment, or a recombinant or synthetic APP substrate containing the amino acid sequence: KM-DA or NL-DA, which is incubated in the presence of an α-secretase and/or β-secretase enzyme, a fragment thereof, or a synthetic or recombinant polypeptide variant having alpha-secretase or beta-secretase activity and effective to cleave the alpha-secretase or beta-secretase cleavage sites of APP, under incubation conditions suitable for the cleavage activity of the enzyme. Suitable substrates optionally include derivatives that may be fusion proteins or peptides that contain the substrate peptide and a modification useful to facilitate the purification or detection of the peptide or its α-secretase and/or β-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example, approximately 200 nanomolar to 10 micromolar substrate, approximately 10 to 200 picomolar enzyme, and approximately 0.1 nanomolar to 10 micromolar, 50 micromolar, or 100 micromolar netrin loop peptide(s), in aqueous solution, at an approximate pH of 4-7, at approximately 37° C., for a time period of approximately 10 minutes to 3 hours. These incubation conditions are illustrative only, and can be varied as required for the particular assay components and/or desired measurement system. Optimization of the incubation conditions for the particular assay components can account for the specific alpha-secretase and/or beta-secretase enzyme used and its pH optimum, any additional enzymes and/or markers that might be used in the assay, and the like. Such optimization is routine and does not require undue experimentation.

One useful assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of alpha-secretase and/or beta-secretase results in cleavage of the substrate at the alpha-secretase and/or beta-secretase cleavage sites, respectively. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assays

Numerous cell-based assays can be used to evaluate the effect of the netrin loop peptide(s) described herein on the ratio of relative alpha-secretase activity to beta-secretase activity and/or on the processing of APP to release amyloidogenic versus non-amyloidogenic Aβ oligomers. Contact of an APP substrate with an alpha-secretase and/or beta-secretase enzyme within the cell and in the presence or absence of compound(s) in question can be used to demonstrate α-secretase and/or β-secretase inhibitory activity of the compound(s). Preferably, the assay in the presence of compound(s) provides at least about 30%, most preferably at least about 50% inhibition of the enzymatic activity, as compared with a non-inhibited control.

In one illustrative embodiment, cells that naturally express alpha-secretase and/or beta-secretase are used. Alternatively, cells can be modified to express a recombinant α-secretase and/or β-secretase or synthetic variant enzymes, as discussed above. In certain embodiments, the APP substrate can be added to the culture medium and in certain embodiments; the substrate is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the α-secretase and/or β-secretase APP cleavage sites can be used, provided that the expressed APP is permitted to contact the enzyme and enzymatic cleavage activity can be analyzed.

Human cell lines that normally process Aβ from APP provide a useful means to assay inhibitory activities of the compound(s) described herein. Production and release of Aβ and/or other cleavage products into the culture medium can be measured, for example by immunoassay, such as Western blot or enzyme-linked immunoassay (EIA) such as by ELISA.

In certain embodiments, cells expressing an APP substrate and an active α-secretase and/or β-secretase can be incubated in the presence of the compound(s) being tested to demonstrate the effect of the compound(s) on relative enzymatic activity of the α-secretase and/or β-secretase as compared with a control. Relative activity of the alpha-secretase to the beta-secretase can be measured by analysis of one or more cleavage products of the APP substrate. For example, inhibition of α-secretase activity against the substrate APP would be expected to decrease release of specific α-secretase induced APP cleavage products such as Aβ, sAPPβ and APPneo. Promotion or enhancement of β-secretase activity against the substrate APP would be expected to increase release of specific alpha-secretase induced APP cleavage products such as sAPPα and p3 peptide.

Although both neural and non-neural cells process and release Aβ, levels of endogenous beta-secretase activity are low and often difficult to detect by EIA. The use of cell types known to have enhanced beta-secretase activity, enhanced processing of APP to Aβ, and/or enhanced production of Aβ are therefore preferred. For example, transfection of cells with the Swedish Mutant form of APP (APP-SW); with APP-KK (APP containing an ER retention signal (-KKQN-, (SEQ ID NO:7)) appended to the C terminus of APP), or with APP-SW-KK provides cells having enhanced beta-secretase activity and producing amounts of Aβ that can be readily measured.

In such assays, for example, the cells expressing APP, alpha-secretase and/or beta-secretase are incubated in a culture medium under conditions suitable for α-secretase and/or β-secretase enzymatic activity at its cleavage site on the APP substrate. On exposure of the cells to one or more netrin loop peptide(s), the amount of Aβ released into the medium and/or the amount of CTF99 fragments of APP in the cell lysates is reduced as compared with the control. The cleavage products of APP can be analyzed, for example, by immune reactions with specific antibodies, as discussed above.

In certain embodiments, preferred cells for analysis of α-secretase and/or β-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze the effect of a netrin loop peptide described herein on the relative alpha-secretase and/or beta-secretase activity and/or processing of APP to release Aβ. For example, transgenic animals expressing APP substrate, alpha-secretase and/or beta-secretase enzyme can be used to demonstrate inhibitory activity of the netrin loop peptide(s). Certain transgenic animal models have been described, for example, in U.S. Pat. Nos. 5,877,399; 5,612,486; 5,387,742; 5,720,936; 5,850,003; 5,877,015, and 5,811,633, and in Games et al., (1995) *Nature* 373: 523-527. Preferred are animals that exhibit characteristics associated with the pathophysiology of AD. Administration of netrin loop peptide(s) to the transgenic mice described herein provides an alternative method for demonstrating the inhibitory activity of the compound(s) in question. In certain embodiments, administration of netrin loop peptide(s) in a pharmaceutically effective carrier and via an administrative route that reaches the target tissue in an appropriate therapeutic amount is preferred.

Inhibition of beta-secretase mediated cleavage of APP at the beta-secretase cleavage site and of Aβ release can be analyzed in these animals by measure of cleavage fragments in the animal's body fluids such as cerebral fluid or tissues. Likewise, promotion or enhancement of alpha-secretase mediated cleavage of APP at the alpha-secretase cleavage site and of release of sAPPα can be analyzed in these animals by measure of cleavage fragments in the animal's body fluids such as cerebral fluid or tissues. In certain embodiments, analysis of brain tissues for Aβ deposits or plaques is preferred.

In certain illustrative assays, an APP substrate is contacted with an alpha-secretase and/or beta-secretase enzyme in the presence of the netrin loop peptide(s) under conditions sufficient to permit enzymatic mediated cleavage of APP and/or release of Aβ from the substrate. The netrin loop peptide(s) are deemed effective when they reduce beta-secretase-mediated cleavage of APP at the beta-secretase cleavage site and/or reduces released amounts of Aβ. The netrin loop peptide(s) are also deemed effective if they enhance α-secretase-mediated cleavage of APP at the α-secretase cleavage site and to increase released amounts of sAPPα and/or to reduce Aβ deposition in brain tissues of the animal, and to reduce the number and/or size of beta amyloid plaques.

Methods of Monitoring Clinical Efficacy

In certain embodiments, clinical efficacy can be monitored using any method known in the art. Measurable biomarkers to monitor efficacy include, but are not limited to, monitoring blood, plasma, serum, mucous or cerebrospinal fluid (CSF) levels of sAPPα, sAPPβ, Aβ42, Aβ40, APPneo and p3 (e.g., Aβ17-42 or Aβ17-40). Detection of increased levels of sAPPα and/or p3 and decreased levels of sAPPβ and APPneo are indicators that the treatment or prevention regime is efficacious. Conversely, detection of decreased levels of sAPPα and/or p3, Aβ42 and increased levels of sAPPβ and APPneo are indicators that the treatment or prevention regime is not efficacious. Other biomarkers include Tau and phospho-Tau (pTau). Detection of decreased levels of Tau and pTau are indicators that the treatment or prevention regime is efficacious.

Efficacy can also be determined by measuring amyloid plaque load in the brain. The treatment or prevention regime is considered efficacious when the amyloid plaque load in the brain does not increase or is reduced. Conversely, the treatment or prevention regime is considered inefficacious when the amyloid plaque load in the brain increases. Amyloid plaque load can be determined using any method known in the art, e.g., including magnetic resonance imaging (MRI).

Efficacy can also be determined by measuring the cognitive abilities of the subject. Cognitive abilities can be measured using any method known in the art. One test is the clinical dementia rating (CDR) described above, while another is the mini mental state examination (MMSE) (Folstein, et al., *Journal of Psychiatric Research* 12 (3): 189-98). In certain embodiments, subjects who maintain the same score or who achieve a higher score on a CDR and/or on an MMSE indicate that the treatment or prevention regime is efficacious. Conversely, subjects who score lower on a CDR and/or on an MMSE indicate that the treatment or prevention regime has not been efficacious.

In certain embodiments, the monitoring methods can entail determining a baseline value of a measurable biomarker or parameter (e.g., amyloid plaque load or cognitive ability) in a subject before administering a dosage of netrin-loop peptide(s), and comparing this with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment, but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and a decision not to resume treatment can be considered/evaluated. In all of these cases, a significant difference relative to the control level (e.g., more than a standard deviation) is an indicator that resumption of the subject should be considered.

In certain embodiments, the tissue sample for analysis is typically blood, plasma, serum, mucous or cerebrospinal fluid from the subject.

Articles of Manufacture

In certain embodiments articles of manufacture that encompass finished, packaged and labeled pharmaceutical products are contemplated. The articles of manufacture include the appropriate unit dosage form of the netrin loop peptide(s) in an appropriate vessel or container such as, for example, a glass vial or other container that is hermetically sealed. In the case of dosage forms suitable for parenteral administration, the active ingredient, e.g. one or more netrin loop peptides, is preferably sterile and suitable for administration as a particulate-free solution. In other words, the invention encompasses both parenteral solutions and lyophilized powders, in certain embodiments each being sterile, and the latter being suitable for reconstitution prior to injection. Alternatively, the unit dosage form may be a solid suitable for oral, transdermal, topical or mucosal delivery.

In some embodiments, the unit dosage form is suitable for intravenous, intramuscular, topical or subcutaneous delivery. Thus, the invention encompasses solutions, which are preferably sterile and suitable for each route of delivery. The concentration of agents and amounts delivered are included as described herein.

As with any pharmaceutical product, the packaging material and container are designed to protect the stability of the product during storage and shipment. In addition, the articles of manufacture can include instructions for use or other information material that can advise the user such as, for example, a physician, technician or patient, regarding how to properly administer the composition as prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. The informational material should indicate that anaphylaxis can be fatal and may occur when any foreign protein is introduced into the body. The informational material should indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In some embodiments, the articles of manufacture can comprise one or more packaging materials such as, for example, a box, bottle, tube, vial, container, sprayer, insufflator, intravenous (I.V.) bag, envelope, and the like; and at least one unit dosage form of an agent comprising one or more loop peptide(s) and/or mimetics thereof and a packaging material. In some embodiments, the articles of manufacture may also include instructions for using the composition as a diagnostic, prophylactic, therapeutic, or ameliorative treatment for the disease of concern.

In some embodiments, the articles of manufacture can comprise one or more packaging materials such as, for example, a box, bottle, tube, vial, container, sprayer, insufflator, intravenous (I.V.) bag, envelope, and the like; and a first composition comprising at least one unit dosage form of an agent comprising one or more loop peptide(s) and/or mimetics thereof within the packaging material, along with a second composition comprising a second agent such as, for example, an agent used in the treatment and/or prophylaxis of Alzheimer's disease (e.g., as described herein), or any prodrugs, codrugs, metabolites, analogs, homologues, congeners, derivatives, salts and combinations thereof. In some embodiments, the articles of manufacture may also include instructions for using the composition as a prophylactic, therapeutic, or ameliorative treatment for the disease of concern.

EXAMPLES

The following examples are offered to illustrate, but not to limit the claimed invention.

Example 1

Netrin Loop Peptides that Alter APP Signaling and/or Switch APP Processing from Aberrant to Normal We have found that netrin-1 functions as a ligand for APP, that it modulates APP signaling, and that it regulates Aβ peptide production in Alzheimer model transgenic mice. Furthermore, we have found that netrin-1 ameliorates the AD phenotype when delivered intracerebroventricularly. Accordingly, netrin-1, peptides derived from netrin-1, and peptidomimetics based on netrin-1, as well as netrin-1 secretagogues, all become important potential therapeutics for AD, MCI, and pre-AD conditions.

Netrin-1 is a soluble molecule initially described by M. Tessier-Lavigne and colleagues as the first chemotropic cue involved in axon guidance (Serafini et al. (1994) *Cell* 78: 409-424). Netrin-1 plays a critical role during nervous system development by mediating chemo-attraction and chemorepulsion of axons and neurons through its interaction with DCC (deleted in colorectal cancer) and UNC5H1-4 (uncoordinated gene-5 homologues 1-4) (Keino-Masu et al. (1996) *Cell* 87: 175-185; Leonardo et al. (1997) *Nature* 386: 833-838; Serafini et al. (1994) *Cell* 78: 409-424; Serafini et al. (1996) *Cell* 87: 1001-1014). However, netrin-1 has also been described as a survival factor, involved in, among other effects, the regulation of tumorigenesis (Mazelin et al. (2004) *Nature* 431: 80-84). Such dual effects on nervous system development and tumorigenesis are characteristic of so-called dependence receptors, of which DCC and UNC5H's represent two examples (Llambi et al. (2001) *EMBO J.*, 20: 2715-2722; Mehlen et al. (1997) *Cell Death Differ.*, 6(3): 227-233).

Netrin Model and Design of Cyclic Peptides

Figure 1B:
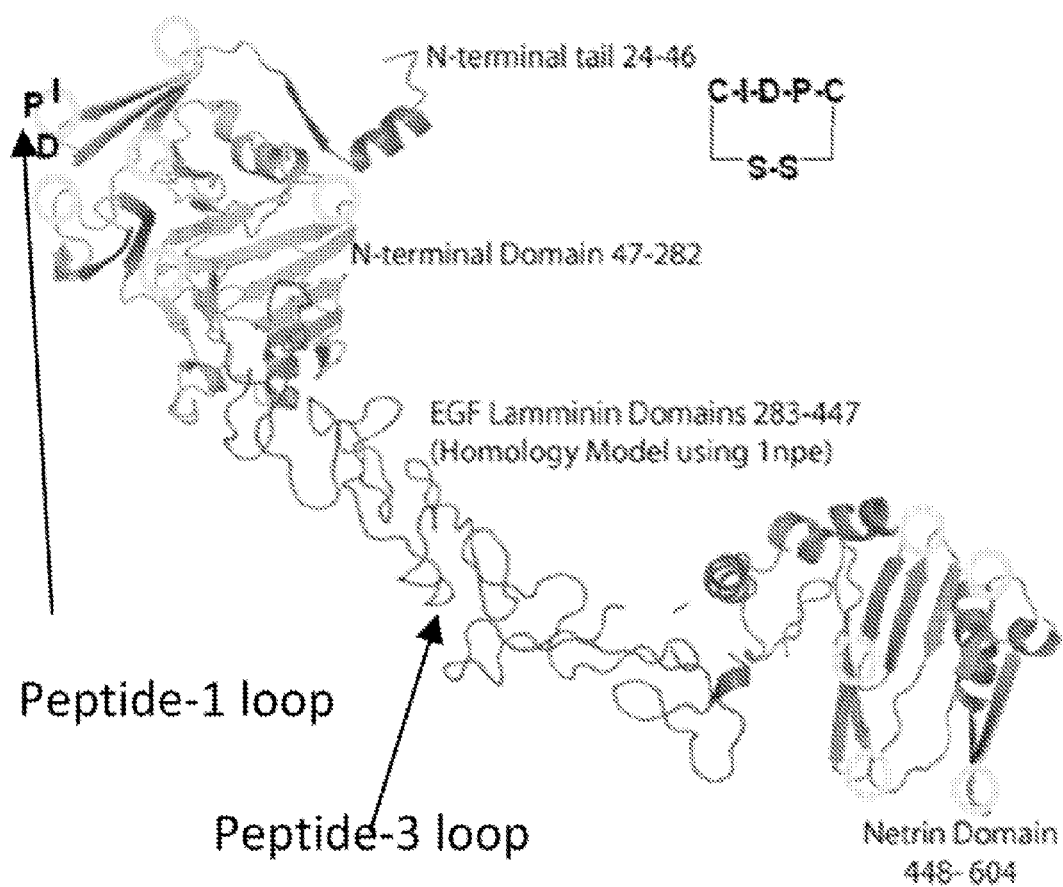
FIG. 1B illustrates netrin-1 based loop peptides. All models are from HMMSTR-ROSETTA.

We have used a computational program called COOT to generate a Rosetta model of the human netrin-1 (FIG. 1A). We then identified loops on the N-terminal, C-terminal and laminin domain of netrin-1 to identify interaction loops (see FIG. 1B). We then prepared these loops which had two cysteines at the N and C-terminus. The cycle was formed through an intra-molecular disulfide bond.

The synthesis of the cyclic peptides was done using solid phase Fmoc-synthesis using the standard Wang resin. The linear peptide synthesis was terminated with a Dansyl N-terminal group. After removal of the peptide from the resin it was cyclised. The disulfide bond was formed by oxidation using the Fenton chemistry and monitored using Elman reagent. The cyclic peptide was then purified using standard reverse phase HPLC to obtain the cylic peptides in >95% purity Extracellular Signal-Regulated Kinase (ERK)—1 and 2

Figure 2:
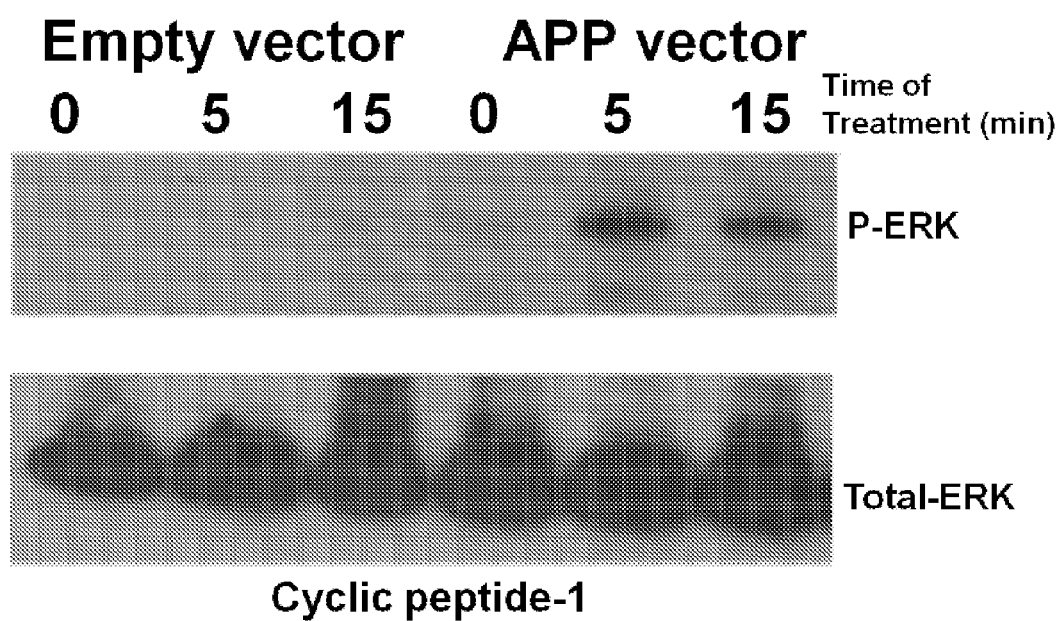
FIG. 2 shows results from a Western Blot analysis showing ERK phosphorylation associated with APP based cell signaling using cyclic peptide-1 (21 uM). This effect is not seen with cyclic peptide-2 or cyclic peptide-3. Netrin-1 induces ERK phosphorylation both in APP cells and in cells without APP such as having DCC. Cyclic peptide-1 is APP specific

ERK phosphorylation is associated with cell signaling. In B103 cells co-transfected with APP and treated with micromolar concentrations of the cyclic peptide we get activation of ERK phosphorylation suggesting that they induce a signaling event (see FIG. 2). This assay was based on a western blot analysis.

sAPPα Levels

The cyclic peptides also appear to be able to switch the processing of APP from the aberrant (Abeta generating) to the normal pathway resulting in an increase in the serum APPα (sAPPα) levels. These experiments were done in APP stably transfected B103 cells. We have setup an AlphaLisa assay to help measure this effect. The C-I-D-P-C peptide (SEQ ID NO:1, Formula 1) was active in increasing sAPPα levels as measured by ALPHALISA assay using the PerkinElmer Enspire AlphaLisa reader (see FIG. 3).

sAPPα/Aβ$_{42}$ Ratios

Figure 4:
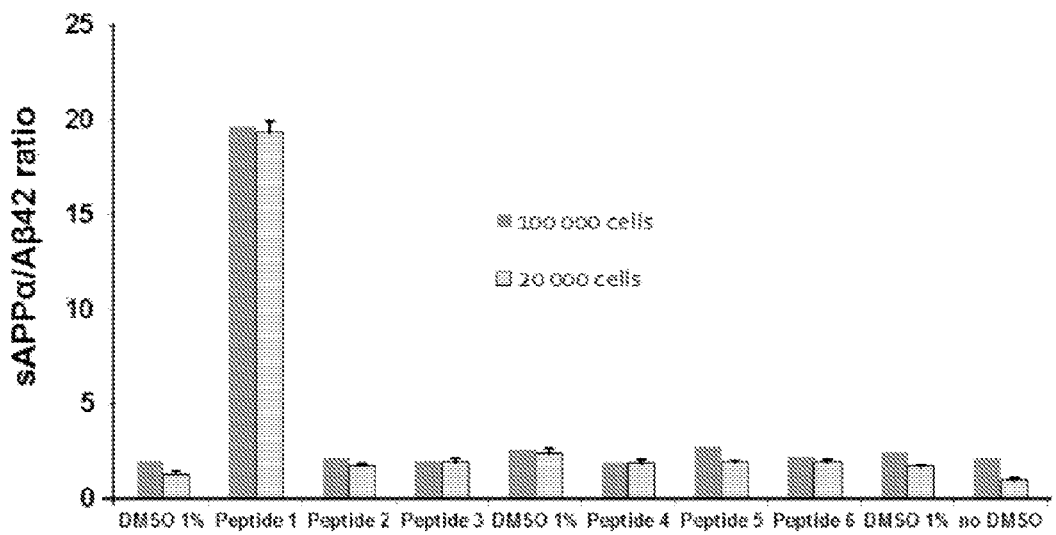
FIG. 4 illustrates the specific increase in the sAPPalpha/Abeta42 ratio with cyclic peptide-1, but not by the other cyclic peptides at similar concentrations. Peptide testing was done at 100 μM in APP CHO cells.
Figure 5:
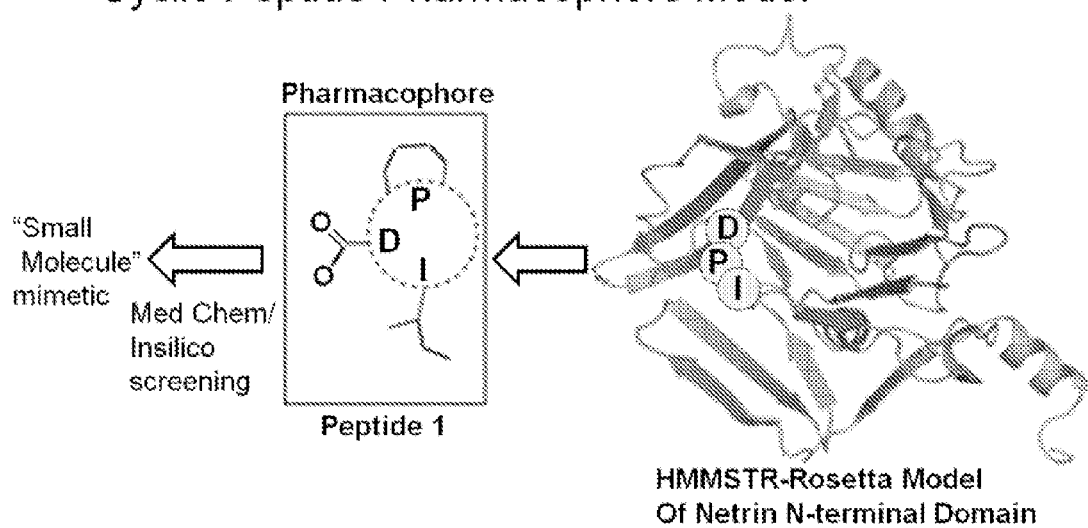
FIG. 5 illustrates a pharmacophore model developed based on the cyclic peptide-1 which is based on a loop sequence from the Netrin N-terminal domain. The model was developed using HMMSTR-ROSETTA.

Using the AlphLisa assay we can also measure the ratio of the levels of sAPPα to the level of Aβ42 produced by the stably transfected APP in B103 cells. The cells when treated with the cyclic peptides show an increase in the sAPPα/Aβ42 ratio over untreated controls. FIG. 4 illustrates the specific increase in the sAPPalpha/Abeta42 ratio with cyclic peptide-1. FIG. 5 illustrates a pharmacophore model developed based on the cyclic peptide-1 which is based on a loop sequence from the Netrin N-terminal domain. The model was developed using HMMSTR-ROSETTA.

Figure 6:
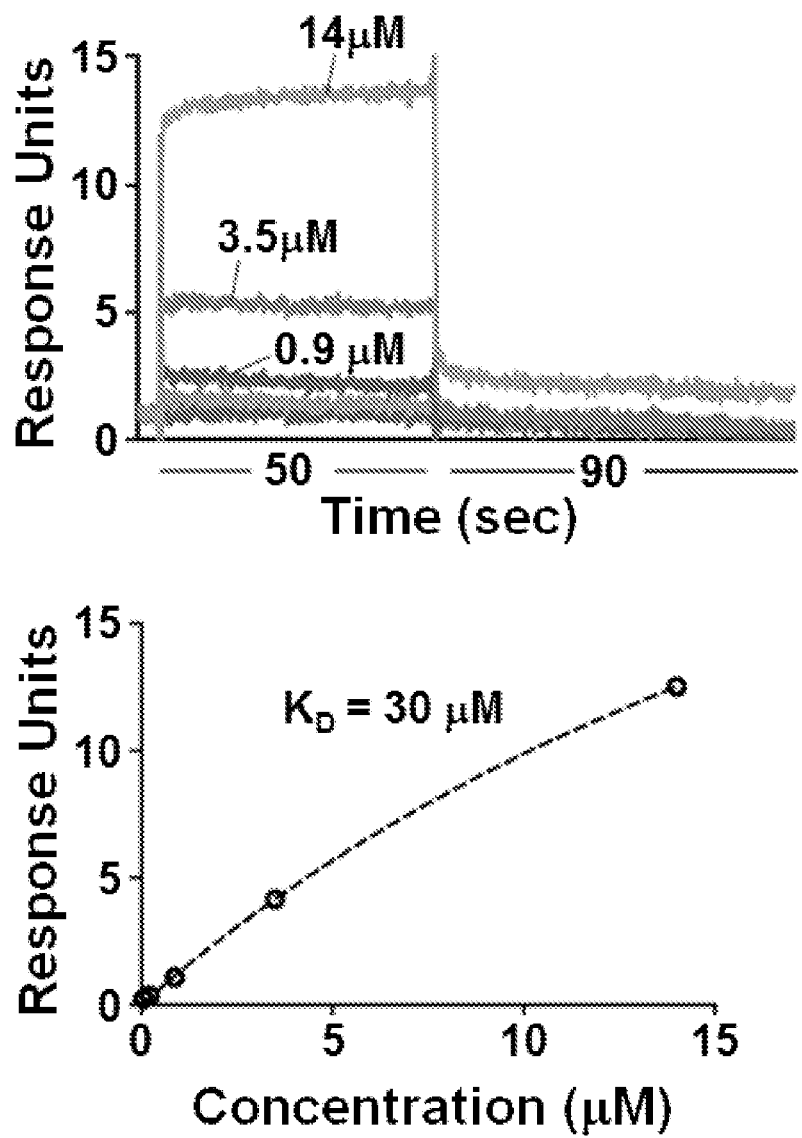
FIG. 6 shows that that cyclic-peptide-1 binds eAPP fragments by surface plasmon resonance (SPR). Data are shown for peptide 1 binding to eAPP$_{575-624}$.

FIG. 6 shows that that cyclic-peptide-1 binds eAPP fragments by surface plasmon resonance (SPR).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A cyclic peptide, wherein said peptide is a pentapeptide comprising the formula:

$C^1$-$X^2$-$X^3$-$X^4$-$C^5$ wherein:
- $C^1$ and $C^5$ are independently selected cysteine or homocysteine, and $C^1$ and $C^5$ are attached to each other by a linkage that does not comprise $X^2$, $X^3$, and $X^4$;
- $X^2$-$X^3$-$X^4$ is selected from the group consisting of I-D-P, P-H-F, and V-A-G; and
- said peptide, when administered to a cell alters APP signaling and/or switches APP processing from aberrant to normal.

2. The peptide of claim 1, wherein $X^2$-$X^3$-$X^4$ is I-D-P.

3. The peptide of claim 1, wherein $X^2$-$X^3$-$X^4$ is P-H-F.

4. The peptide of claim 1, wherein $X^2$-$X^3$-$X^4$ is V-A-G.

5. The peptide of claim 1, wherein $C^1$ and $C^5$ are both cysteine.

6. The peptide of claim 1, wherein said linkage comprises a disulfide bond or a polyethylene glycol.

7. The peptide of claim 1, wherein said peptide is attached to a moiety that targets or facilitates transport across the blood brain barrier.

* * * * *